US012643885B2

(12) United States Patent
Kawai

(10) Patent No.: US 12,643,885 B2
(45) Date of Patent: Jun. 2, 2026

(54) KRAS G12D PROTEIN INHIBITORS

(71) Applicant: TAIHO PHARMACEUTICAL CO., LTD., Tokyo (JP)

(72) Inventor: Yuichi Kawai, Tsukuba (JP)

(73) Assignee: TAIHO PHARMACEUTICAL CO., LTD., Tokyo (JP)

( * ) Notice: Subject to any disclaimer, the term of this patent is extended or adjusted under 35 U.S.C. 154(b) by 807 days.

(21) Appl. No.: 17/920,866

(22) PCT Filed: Apr. 23, 2021

(86) PCT No.: PCT/JP2021/017316
§ 371 (c)(1),
(2) Date: Oct. 24, 2022

(87) PCT Pub. No.: WO2021/215544
PCT Pub. Date: Oct. 28, 2021

(65) Prior Publication Data

US 2023/0174518 A1 Jun. 8, 2023

Related U.S. Application Data

(60) Provisional application No. 63/015,132, filed on Apr. 24, 2020.

(51) Int. Cl.
*C07D 403/14* (2006.01)
*A61K 45/06* (2006.01)
*C07D 403/12* (2006.01)

(52) U.S. Cl.
CPC ............ *C07D 403/14* (2013.01); *A61K 45/06* (2013.01); *C07D 403/12* (2013.01)

(58) Field of Classification Search
None
See application file for complete search history.

(56) References Cited

U.S. PATENT DOCUMENTS 4,034,075 A 7/1977 Bays et al.
7,084,155 B2 * 8/2006 Bridger ................ C07D 493/04 546/171
9,840,516 B2 12/2017 Li et al.
10,125,134 B2 11/2018 Blake et al.
10,144,724 B2 12/2018 Li et al.
10,556,906 B2 2/2020 Kuramoto et al.
10,662,204 B2 5/2020 Planken et al.
10,988,485 B2 4/2021 Minatti et al.
11,045,484 B2 6/2021 Wurz et al.
11,090,304 B2 8/2021 Allen et al.
11,096,939 B2 8/2021 Booker et al.
11,299,491 B2 4/2022 Parsons et al.
11,453,683 B1 9/2022 Wang et al.
11,459,327 B1 10/2022 Lv et al.
11,530,218 B2 12/2022 Zhao et al.
11,697,657 B2 7/2023 Bharathan et al.
11,932,633 B2 3/2024 Marx et al.
12,065,430 B2 * 8/2024 Sakamoto ............... A61P 35/00
12,208,099 B2 1/2025 Aranda et al.
2006/0135532 A1 6/2006 Bryant et al.
2010/0331305 A1 12/2010 Bergeron et al.
2014/0275070 A1 9/2014 Grembecka et al.
2014/0288045 A1 9/2014 Ren et al.
2014/0371203 A1 12/2014 Madge et al.
2015/0176010 A1 6/2015 Wersinger
2015/0239900 A1 8/2015 Li et al.
2015/0246934 A1 9/2015 Bensen et al.
2016/0046647 A1 2/2016 Grembecka et al.
2016/0108019 A1 4/2016 Li et al.
2016/0137665 A1 5/2016 Grembecka et al.
2016/0152634 A1 6/2016 Madge et al.
2016/0159738 A1 6/2016 Ren et al.
2016/0297774 A1 10/2016 Li et al.
2016/0318866 A1 11/2016 Becker-Pelster et al.
2017/0131278 A1 5/2017 Patricelli et al.
2017/0197945 A1 7/2017 Li et al.
2017/0253611 A1 9/2017 Grembecka et al.
2018/0072723 A1 3/2018 Blake et al.
2018/0118757 A1 5/2018 Li et al.
2018/0127396 A1 5/2018 Li et al.
2018/0141927 A1 5/2018 Li et al.
2018/0162812 A1 6/2018 Ren et al.
2018/0177767 A1 6/2018 Lanman et al.
2018/0334454 A1 11/2018 Lanman et al.
2019/0062313 A1 2/2019 Li et al.
2019/0062330 A1 2/2019 Blake et al.
(Continued)

FOREIGN PATENT DOCUMENTS

CN 104011054 A 8/2014
CN 107556289 A 1/2018
(Continued)

OTHER PUBLICATIONS

El-Meligie, Salwa E. M. et al., "New synthetic approaches to thieno[3,2-d]pyrimidine and thieno[3, 4-b]pyridine derivatives", Chemical Papers, vol. 74, pp. 2501-2514 (2020).
El-Kashef, H et al., "Pyridine-Based Heterocycles. Synthesis of New Pyrido[4',3':4,5]thieno[2,3-d]pyrimidines and Related Heterocycles", Molecules, vol. 15, pp. 2651-2666 (2010).
Szanto, Get al., "New P2X3 receptor antagonists. Part 2: Identification and SAR of quinazolinones," Bioorganic and Medicinal Chemistry Letters, vol. 26, No. 16, pp. 3905-3912, abstract (2016).
Sanad, SMH et al., "Efficient Synthesis and Characterization of Novel Pyrido[3',2':4,5]thieno[3,2-d]pyrimidines and Their Fused [1,2,4]triazole Derivatives", Journal of Heterocyclic Chemistry, vol. 55, No. 12, pp. 2823-2833, abstract (2018).
(Continued)

*Primary Examiner* — Clinton A Brooks
*Assistant Examiner* — Nicola Maria Bauer
(74) *Attorney, Agent, or Firm* — Venable LLP

(57) ABSTRACT

Compounds and pharmaceutically acceptable salts thereof inhibit the G12D mutant of KRAS protein and are expected to have utility as therapeutic agents, for example, for the treatment of cancer.

26 Claims, No Drawings

Specification includes a Sequence Listing.

(56) References Cited

U.S. PATENT DOCUMENTS

| | | | |
|---|---|---|---|
| 2019/0127336 A1 | 5/2019 | Li et al. | |
| 2019/0144444 A1 | 5/2019 | Blake et al. | |
| 2019/0233440 A1 | 8/2019 | Planken et al. | |
| 2019/0248767 A1 | 8/2019 | Planken et al. | |
| 2019/0270743 A1 | 9/2019 | Marx et al. | |
| 2019/0276432 A1 | 9/2019 | Beaumont et al. | |
| 2019/0284144 A1 | 9/2019 | Li et al. | |
| 2019/0292182 A1 | 9/2019 | Kuramoto et al. | |
| 2019/0343838 A1 | 11/2019 | Allen et al. | |
| 2019/0374542 A1 | 12/2019 | Allen et al. | |
| 2019/0375749 A1 | 12/2019 | Chen et al. | |
| 2020/0055845 A1 | 2/2020 | Lanman et al. | |
| 2020/0069657 A1 | 3/2020 | Lanman et al. | |
| 2020/0115363 A1 | 4/2020 | Li et al. | |
| 2020/0115375 A1 | 4/2020 | Barda et al. | |
| 2020/0140437 A1 | 5/2020 | Kuramoto et al. | |
| 2020/0165231 A1 | 5/2020 | Shin et al. | |
| 2020/0181118 A1 | 6/2020 | Malhotra et al. | |
| 2020/0237771 A1 | 7/2020 | Hallur et al. | |
| 2020/0262837 A1 | 8/2020 | Marx et al. | |
| 2020/0289503 A1 | 9/2020 | Huang | |
| 2020/0331911 A1 | 10/2020 | Marx et al. | |
| 2021/0009577 A1 | 1/2021 | Lanman et al. | |
| 2021/0024501 A1 | 1/2021 | Li et al. | |
| 2021/0040089 A1 | 2/2021 | Gao et al. | |
| 2021/0047297 A1 | 2/2021 | Schulze et al. | |
| 2021/0122764 A1 | 4/2021 | Bharathan et al. | |
| 2021/0395234 A1 | 12/2021 | Sakamoto et al. | |
| 2022/0064141 A1 | 3/2022 | Fang et al. | |
| 2022/0298174 A1 | 9/2022 | Guo et al. | |
| 2022/0315597 A1 | 10/2022 | Su et al. | |
| 2022/0315598 A1 | 10/2022 | Xu et al. | |
| 2022/0370416 A1 | 11/2022 | Chu et al. | |
| 2022/0389029 A1 | 12/2022 | Guo et al. | |
| 2022/0402916 A1 | 12/2022 | Hoover et al. | |
| 2023/0023023 A1 | 1/2023 | Shibata et al. | |
| 2023/0049402 A1 | 2/2023 | Sakamoto et al. | |
| 2023/0181536 A1* | 6/2023 | Abe | A61K 31/5365<br>514/210.18 |
| 2023/0348495 A1 | 11/2023 | Kawai et al. | |
| 2023/0416266 A1 | 12/2023 | Han et al. | |
| 2024/0043448 A1 | 2/2024 | Bharathan et al. | |
| 2024/0083913 A1 | 3/2024 | Bharathan et al. | |
| 2024/0124478 A1 | 4/2024 | Han et al. | |
| 2024/0174691 A1 | 5/2024 | Jiang et al. | |
| 2024/0239788 A1 | 7/2024 | Sloman et al. | |
| 2024/0246968 A1 | 7/2024 | Shibata et al. | |
| 2024/0262842 A1 | 8/2024 | Shibata et al. | |
| 2024/0317759 A1 | 9/2024 | Kobayakawa et al. | |
| 2024/0376123 A1 | 11/2024 | Zhou et al. | |
| 2024/0417408 A1 | 12/2024 | Shibata et al. | |
| 2025/0136615 A1 | 5/2025 | Kawamura et al. | |

FOREIGN PATENT DOCUMENTS

| | | | | |
|---|---|---|---|---|
| CN | 109843856 | A | 6/2019 | |
| CN | 112390788 | A1 | 2/2021 | |
| CN | 112430234 | A | 3/2021 | |
| CN | 114615981 | A | 6/2022 | |
| EP | 3871673 | A1 | 9/2021 | |
| EP | 4053120 | A1 | 9/2022 | |
| EP | 4397664 | A1 | 10/2024 | |
| JP | 2016-519072 | A | 6/2016 | |
| JP | 2016-532656 | A | 10/2016 | |
| JP | 2017-528498 | A | 9/2017 | |
| WO | 03/037898 | A1 | 5/2003 | |
| WO | 2005/019177 | A1 | 3/2005 | |
| WO | 2009/114575 | A1 | 9/2009 | |
| WO | 2010/064705 | A1 | 6/2010 | |
| WO | 2013/072694 | A1 | 5/2013 | |
| WO | 2014/043272 | A1 | 3/2014 | |
| WO | 2014/143659 | A1 | 9/2014 | |
| WO | WO-2014152588 | A1 * | 9/2014 | C07D 285/16 |
| WO | 2014/164543 | A1 | 10/2014 | |
| WO | 2015/054572 | A1 | 4/2015 | |
| WO | 2015/091415 | A1 | 6/2015 | |
| WO | 2015/131005 | A1 | 9/2015 | |
| WO | 2016/029454 | A1 | 3/2016 | |
| WO | 2016/044772 | A1 | 3/2016 | |
| WO | 2016/049524 | A1 | 3/2016 | |
| WO | 2016/049565 | A1 | 3/2016 | |
| WO | 2016/049568 | A1 | 3/2016 | |
| WO | 2016/164675 | A1 | 10/2016 | |
| WO | 2016/168540 | A1 | 10/2016 | |
| WO | 2017/015562 | A1 | 1/2017 | |
| WO | 2017/058728 | A1 | 4/2017 | |
| WO | 2017/058768 | A1 | 4/2017 | |
| WO | 2017/058792 | A1 | 4/2017 | |
| WO | 2017/058805 | A1 | 4/2017 | |
| WO | 2017/058807 | A1 | 4/2017 | |
| WO | 2017/058902 | A1 | 4/2017 | |
| WO | 2017/058915 | A1 | 4/2017 | |
| WO | 2017/070256 | A2 | 4/2017 | |
| WO | 2017/087528 | A1 | 5/2017 | |
| WO | 2017/100546 | A1 | 6/2017 | |
| WO | 2017/172979 | A1 | 10/2017 | |
| WO | 2017/201161 | A1 | 11/2017 | |
| WO | 2018/022897 | A1 | 2/2018 | |
| WO | 2018/064510 | A1 | 4/2018 | |
| WO | 2018/068017 | A1 | 4/2018 | |
| WO | 2018/119183 | A2 | 6/2018 | |
| WO | 2018/140512 | A1 | 8/2018 | |
| WO | 2018/140513 | A1 | 8/2018 | |
| WO | 2018/140514 | A1 | 8/2018 | |
| WO | 2018/140598 | A1 | 8/2018 | |
| WO | 2018/140599 | A1 | 8/2018 | |
| WO | 2018/140600 | A1 | 8/2018 | |
| WO | 2018/143315 | A1 | 8/2018 | |
| WO | 2018/206539 | A1 | 11/2018 | |
| WO | 2018/217651 | A1 | 11/2018 | |
| WO | 2018/218069 | A1 | 11/2018 | |
| WO | 2018/218070 | A2 | 11/2018 | |
| WO | 2018/218071 | A1 | 11/2018 | |
| WO | 2019/051291 | A1 | 3/2019 | |
| WO | 2019/058132 | A1 | 3/2019 | |
| WO | 2019/058393 | A1 | 3/2019 | |
| WO | 2019/077631 | A1 | 4/2019 | |
| WO | 2019/099524 | A1 | 5/2019 | |
| WO | 2019/099703 | A1 | 5/2019 | |
| WO | 2019/110751 | A1 | 6/2019 | |
| WO | 2019/155399 | A1 | 8/2019 | |
| WO | 2019/167000 | A1 | 9/2019 | |
| WO | 2019/185525 | A1 | 10/2019 | |
| WO | 2019/215203 | A1 | 11/2019 | |
| WO | 2019213526 | A1 | 11/2019 | |
| WO | 2019217307 | A1 | 11/2019 | |
| WO | 2019217691 | A1 | 11/2019 | |
| WO | 2019232419 | A1 | 12/2019 | |
| WO | 2020/035031 | A1 | 2/2020 | |
| WO | 2020/041331 | A1 | 2/2020 | |
| WO | 2020/050890 | A2 | 3/2020 | |
| WO | 2020047192 | A1 | 3/2020 | |
| WO | 2020055755 | A1 | 3/2020 | |
| WO | 2020055756 | A1 | 3/2020 | |
| WO | 2020055758 | A1 | 3/2020 | |
| WO | 2020055760 | A1 | 3/2020 | |
| WO | 2020055761 | A1 | 3/2020 | |
| WO | 2020/085493 | A1 | 4/2020 | |
| WO | 2020/097537 | A2 | 5/2020 | |
| WO | 2020/101736 | A1 | 5/2020 | |
| WO | 2020102730 | A1 | 5/2020 | |
| WO | 2020/113071 | A1 | 6/2020 | |
| WO | 2020118066 | A1 | 6/2020 | |
| WO | 2020/146613 | A1 | 7/2020 | |
| WO | 2020/156285 | A1 | 8/2020 | |
| WO | 2020/177629 | A1 | 9/2020 | |
| WO | 2020/178282 | A1 | 9/2020 | |
| WO | 2020/221239 | A1 | 11/2020 | |
| WO | 2020/233592 | A1 | 11/2020 | |
| WO | 2020/234103 | A1 | 11/2020 | |
| WO | 2020/236940 | A1 | 11/2020 | |
| WO | 2020/238791 | A1 | 12/2020 | |
| WO | 2020/239077 | A1 | 12/2020 | |

(56) References Cited

FOREIGN PATENT DOCUMENTS

| | | | |
|---|---|---|---|
| WO | 2020/239123 | A1 | 12/2020 |
| WO | 2020/244637 | A1 | 12/2020 |
| WO | 2020/259432 | A1 | 12/2020 |
| WO | 2020/259513 | A1 | 12/2020 |
| WO | 2020/259573 | A1 | 12/2020 |
| WO | 2021/000885 | A1 | 1/2021 |
| WO | 2021/023154 | A1 | 2/2021 |
| WO | 2021/027911 | A1 | 2/2021 |
| WO | 2021/027943 | A1 | 2/2021 |
| WO | 2021/031952 | A1 | 2/2021 |
| WO | 2021/037018 | A1 | 3/2021 |
| WO | 2021/041671 | A1 | 3/2021 |
| WO | 2021/043322 | A1 | 3/2021 |
| WO | 2021/052499 | A1 | 3/2021 |
| WO | 2021/055728 | A1 | 3/2021 |
| WO | 2021/057832 | A1 | 4/2021 |
| WO | 2021/058018 | A1 | 4/2021 |
| WO | 2021/063346 | A1 | 4/2021 |
| WO | 2021/078312 | A1 | 4/2021 |
| WO | 2021/081212 | A1 | 4/2021 |
| WO | 2021/083167 | A1 | 5/2021 |
| WO | 2021/084765 | A1 | 5/2021 |
| WO | 2021/085653 | A1 | 5/2021 |
| WO | 2021/086833 | A1 | 5/2021 |
| WO | 2021/088458 | A1 | 5/2021 |
| WO | 2021/093758 | A1 | 5/2021 |
| WO | 2021/098859 | A1 | 5/2021 |
| WO | 2021/104431 | A1 | 6/2021 |
| WO | 2021/106230 | A1 | 6/2021 |
| WO | 2021/106231 | A1 | 6/2021 |
| WO | 2021/107160 | A1 | 6/2021 |
| WO | 2021/109737 | A1 | 6/2021 |
| WO | 2021/113595 | A1 | 6/2021 |
| WO | 2021/118877 | A1 | 6/2021 |
| WO | 2021/121330 | A1 | 6/2021 |
| WO | 2021/121367 | A1 | 6/2021 |
| WO | 2021/121371 | A1 | 6/2021 |
| WO | 2021/124222 | A1 | 6/2021 |
| WO | 2021/127404 | A1 | 6/2021 |
| WO | 2021/129824 | A1 | 7/2021 |
| WO | 2021/147965 | A1 | 7/2021 |
| WO | 2021/147967 | A1 | 7/2021 |
| WO | 2021142252 | A1 | 7/2021 |
| WO | 2021150613 | A1 | 7/2021 |
| WO | 2021/215545 | A1 | 10/2021 |
| WO | 2021211864 | A1 | 10/2021 |
| WO | 2021/219072 | A1 | 11/2021 |
| WO | 2022002102 | A1 | 1/2022 |
| WO | 2022015375 | A1 | 1/2022 |
| WO | 2022031678 | A1 | 2/2022 |
| WO | 2022/066646 | A1 | 3/2022 |
| WO | 2022042630 | A1 | 3/2022 |
| WO | 2022047260 | A1 | 3/2022 |
| WO | 2022061251 | A1 | 3/2022 |
| WO | 2022068921 | A1 | 4/2022 |
| WO | 2022083569 | A1 | 4/2022 |
| WO | 2022087371 | A1 | 4/2022 |
| WO | 2022087375 | A1 | 4/2022 |
| WO | 2022/105857 | A1 | 5/2022 |
| WO | 2022/109485 | A1 | 5/2022 |
| WO | 2022/109487 | A1 | 5/2022 |
| WO | 2022/132200 | A1 | 6/2022 |
| WO | 2022/133038 | A1 | 6/2022 |
| WO | 2022/148421 | A1 | 7/2022 |
| WO | 2022/148422 | A1 | 7/2022 |
| WO | 2022/173870 | A1 | 8/2022 |
| WO | 2022/177917 | A2 | 8/2022 |
| WO | 2022187688 | A1 | 9/2022 |
| WO | 2022/221739 | A1 | 10/2022 |
| WO | 2022/228568 | A1 | 11/2022 |
| WO | 2022/232318 | A1 | 11/2022 |
| WO | 2022/232320 | A1 | 11/2022 |
| WO | 2022/247760 | A1 | 12/2022 |
| WO | 2022/250170 | A1 | 12/2022 |
| WO | 2022/251576 | A1 | 12/2022 |
| WO | 2022/256459 | A1 | 12/2022 |
| WO | 2022/266206 | A1 | 12/2022 |
| WO | 2022248885 | A2 | 12/2022 |
| WO | 2022258974 | A1 | 12/2022 |
| WO | 2022261210 | A1 | 12/2022 |
| WO | 2022262686 | A1 | 12/2022 |
| WO | 2022266069 | A1 | 12/2022 |
| WO | 2022271658 | A1 | 12/2022 |
| WO | 2023018699 | A1 | 2/2023 |
| WO | 2023018809 | A1 | 2/2023 |
| WO | 2023018812 | A1 | 2/2023 |
| WO | 2023020518 | A1 | 2/2023 |
| WO | 2023020519 | A1 | 2/2023 |
| WO | 2023020521 | A1 | 2/2023 |
| WO | 2023020523 | A1 | 2/2023 |
| WO | 2023/046135 | A1 | 3/2023 |
| WO | 2023034290 | A1 | 3/2023 |
| WO | 2023049697 | A1 | 3/2023 |
| WO | 2023/059596 | A1 | 4/2023 |
| WO | 2023/059597 | A1 | 4/2023 |
| WO | 2023/059598 | A1 | 4/2023 |
| WO | 2023056421 | A1 | 4/2023 |
| WO | 2023056951 | A1 | 4/2023 |
| WO | 2023060253 | A1 | 4/2023 |
| WO | 2023061294 | A1 | 4/2023 |
| WO | 2023061463 | A1 | 4/2023 |
| WO | 2023064857 | A1 | 4/2023 |
| WO | 2023072188 | A1 | 5/2023 |
| WO | 2023/097227 | A1 | 6/2023 |
| WO | 2023/103523 | A1 | 6/2023 |
| WO | 2023098425 | A1 | 6/2023 |
| WO | 2023098426 | A1 | 6/2023 |
| WO | 2023098832 | A1 | 6/2023 |
| WO | 2023099592 | A1 | 6/2023 |
| WO | 2023099608 | A1 | 6/2023 |
| WO | 2023099612 | A1 | 6/2023 |
| WO | 2023099620 | A1 | 6/2023 |
| WO | 2023099623 | A1 | 6/2023 |
| WO | 2023099624 | A1 | 6/2023 |
| WO | 2023101928 | A1 | 6/2023 |
| WO | 2023103906 | A1 | 6/2023 |
| WO | 2023104018 | A1 | 6/2023 |
| WO | 2023105491 | A1 | 6/2023 |
| WO | 2023114733 | A1 | 6/2023 |
| WO | 2023117681 | A1 | 6/2023 |
| WO | 2023122154 | A1 | 6/2023 |
| WO | 2023125627 | A1 | 7/2023 |
| WO | 2023125989 | A1 | 7/2023 |
| WO | 2023133183 | A | 7/2023 |
| WO | 2023/150284 | A2 | 8/2023 |
| WO | 2023/159087 | A1 | 8/2023 |
| WO | 2023/173017 | A1 | 9/2023 |
| WO | 2023/179703 | A1 | 9/2023 |
| WO | 2023/193085 | A1 | 10/2023 |
| WO | 2023/197984 | A1 | 10/2023 |
| WO | 2023/244615 | A1 | 12/2023 |
| WO | 2024/009191 | A1 | 1/2024 |
| WO | 2024/012519 | A1 | 1/2024 |
| WO | 2024/015262 | A1 | 1/2024 |
| WO | 2024/032704 | A1 | 2/2024 |
| WO | 2024/041573 | A1 | 2/2024 |
| WO | 2024/044667 | A2 | 2/2024 |
| WO | 2024031088 | A1 | 2/2024 |
| WO | 2024/063578 | A1 | 3/2024 |
| WO | 2024/083168 | A1 | 4/2024 |
| WO | 2024/088069 | A1 | 5/2024 |
| WO | 2024/103010 | A1 | 5/2024 |
| WO | 2024/120433 | A1 | 6/2024 |
| WO | 2024/209339 | A1 | 10/2024 |
| WO | 2024/213979 | A1 | 10/2024 |
| WO | 2024/233776 | A1 | 11/2024 |
| WO | 2024/238343 | A1 | 11/2024 |
| WO | 2025/019819 | A1 | 1/2025 |

(56) References Cited

FOREIGN PATENT DOCUMENTS

| | | | |
|---|---|---|---|
| WO | 2025/019823 | A1 | 1/2025 |
| WO | 2025/085748 | A1 | 4/2025 |

OTHER PUBLICATIONS

Showalter, H.D. Hollis et al., "Tyrosine Kinase Inhibitors. 16. 6,5,6-Tricyclic Benzothieno[3,2-d]pyrimidines and Pyrimido[S,4-b]- and -[4,5-b]indoles as Potent Inhibitors of the Epidermal Growth Factor Receptor Tyrosine Kinase", Journal of Medicinal Chemistry, vol. 42, No. 26, pp. 5464-5474, abstract (1999).

Wang, H. et al., "Annual review of KRAS inhibitors in 2022", European J. of Medicinal Chem., 249, p. 1-14 (2023).

Sanad, SMH et al., "New thieno[2,3-b ]pyridine-fused pyrimidin-4(3H)-ones as potential thymidylate synthase inhibitors: Synthesis, SAR, in vitro and in silica study", Journal of Molecular Structure, vol. 1282, (2023).

D.S. Hong, et al., "KRASG12C Inhibition with Sotorasib in Advanced Solid Tumors", The New England Journal of Medicine, vol. 383 No. 13 pp. 1207-1217 (2020).

D. Gentile, et al., "Ras Binder Induces a Modified Switch-II Pocket in GTP and GDP States", Cell Chemical Biology, 24, pp. 1455-1466 (2017).

D. Kessler, et al., "Drugging an undruggable pocket on KRAS", Proceedings of the National Academy of Sciences (PNAS), vol. 116, No. 32, pp. 15823-15829 (2019).

Y. Mao, et al., "Design, synthesis and biological evaluation of novel pyrimidine, 3-cyanopyridine and m-amino-N-phenylbenzamide based monocyclic EGFR tyrosine kinase inhibitors", Bioorganic & Medicinal Chemistry, 21, pp. 3090-3104 (2013).

PubChem CID 10121096, PubChem release Jun. 18, 2019, modify date Nov. 21, 2020, retrieved on Feb. 10, 2021 (9 pages).

G. Palfy, et al., "1H, 15N backbone assignment and comparative analysis of the wild type and G12C, G12D, G12V mutants of K-Ras bound to GDP at physiological pH", Biomolecular NMR Assignment, vol. 14, No. 1, pp. 1-7 (2019).

M.R. Janes, et al., "Targeting KRAS Mutant Cancers with a Covalent G12C-Specific Inhibitor", Cell, 172, pp. 578-589 (2018).

M.P. Patricelli, et al., "Selective Inhibition of Oncogenic KRAS Output with Small Molecules Targeting the Inactive State", Cancer Discovery, 6(3), pp. 316-329 (2016).

H. Chuang, et al., "Pharmacological strategies to target oncogenic KRAS signaling in pancreatic cancer", Pharmacological Research, 117, pp. 370-376 (2017).

Lopez-Tapia, F., et al., "Linker Variation and Structure-Activity Relationship Analyses of Carboxylic Acid-based Small Molecule STAT3 Inhibitors", ACS Med. Chem. Lett. 2018, 9, 250-255.

R.B. Kargbo, "Small Molecule Inhibitors of KRAS G12C Mutant", Acs Med. Chem. Lett., vol. 12, pp. 1210-1211 (2021).

International Search Report and Written Opinion in corresponding international application No. PCT/JP2021/017316 dated Sep. 16, 2021 (12 pages).

PubChem SID 469710826, available Jul. 28, 2022.

J.G. Kettle, et al., "Structure-Based Design and Pharmacokinetic Optimization of Covalent Allosteric Inhibitors of the Mutant GTPase Kras G12C", J. Med. Chem., vol. 63, pp. 4468-4483 (2020).

Q. Zheng, et al., "Drugging the Next Undruggable KRAS Allele-Gly12Asp", J. Med. Chem, vol. 65, pp. 3119-3122 (2022).

* cited by examiner

KRAS G12D PROTEIN INHIBITORS

BACKGROUND OF THE INVENTION

RAS, which is a small monomeric GTP-binding protein having a molecular weight of about 21 kDa, acts as a molecular on/off switch. RAS can bind to GTP by binding to proteins of a guanine nucleotide exchange factor (GEF) (e.g., SOS1), which forces the release of a bound nucleotide, and the release of GDP. When RAS binds to GTP, it becomes activated (turned on) and recruits and activates proteins necessary for the propagation of other receptors' signals, such as c-Raf and PI 3-kinase. RAS also possesses enzymatic activity with which it cleaves the terminal phosphate of the nucleotide and converts it to GDP. The rate of conversion is usually slow, but can be dramatically sped up by a protein of the GTPase-activating protein (GAP) class, such as RasGAP. When GTP is converted into GDP, RAS is deactivated (turned off).

Well-known members of the RAS subfamily include HRAS, KRAS, and NRAS. Of these, mutations of KRAS are observed in many malignant tumors: 95% of pancreatic ductal adenocarcinomas (PDAC), 45% of colon and rectal carcinomas (CRC), and 35% of non-small cell lung carcinomas (NSCLC). The mutations often occur in the glycine residue of KRAS at position 12 in 82% of PDAC, 64% of CRC, and 92% of NSCLC. Among such mutations, the predominant mutation of KRAS at position 12 in PDAC (39%) and CRC (44%) has been reported to be a mutation into aspartic acid (Nat Rev Drug Discov. 2014 November; 13 (11), 828-51).

For many years, it was thought that RAS was undruggable, i.e., could not be affected by pharmaceutical intervention. However, it has been reported that targeting the inactive, GDP-bound KRAS G12C is a promising approach for generating novel anti-RAS therapies (Cancer Discov 2016; 6: 316-329). Because KRAS G12C retains the GTPase activity and nucleotide cycling exists in KRAS G12C in cells, an inhibitor bound to inactive KRAS G12C can inhibit the activation of KRAS G12C in cells. As well as KRAS G12C mutant, it has been reported that KRAS G12D also retains GTPase activity (Mol Cancer Res 2015; 13: 1325-1335). Similarly, the strategy for targeting the GDP-bound KRAS G12D and inhibiting the conversion from the GDP- to the GTP-bound state is thought to be extremely attractive for the treatment of cancers associated with the KRAS G12D mutation, e.g., PDAC and CRC.

SUMMARY OF INVENTION

To selectively inhibit the KRAS G12D protein, provided herein are certain compounds of Formula (I)

(I)

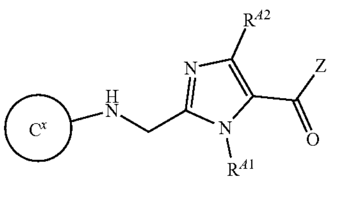

and their pharmaceutically acceptable salts, which modulate the activity of KRAS and thereby affect the signaling pathway which regulates cell growth, differentiation, and proliferation associated with oncological disorders, i.e., cancer.

Also provided herein are processes for preparing compounds of Formula (I), methods for using such compounds to treat cancer, and pharmaceutical compositions which comprise compounds of Formula (I).

DETAILED DESCRIPTION

This disclosure provides a compound of Formula (I) or a pharmaceutically acceptable salt thereof (I)

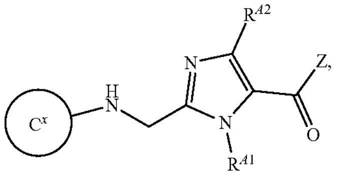

wherein ring $C^x$ is

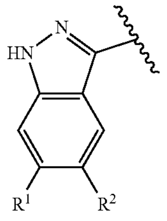

or

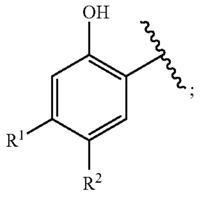

;

$R^1$ is halo;

$R^2$ is $C_1$-$C_6$ alkyl;

$R^{A1}$ is $C_1$-$C_6$ alkyl or ring $C^{A1}$, ring $C^{A1}$ being (a) a 4- to 8-membered saturated monocyclic heterocyclic ring containing from 1 to 2 heteroatoms selected from the group consisting of N, O, and S or (b) $C_3$-$C_6$ cycloalkyl, and ring $C^{A1}$ being unsubstituted or substituted by one to three substituents selected from the group consisting of halo, $C_1$-$C_6$ alkyl, $C_1$-$C_6$ fluoroalkyl, amino, hydroxy, and cyano;

$R^{A2}$ is chloro; and

Z is

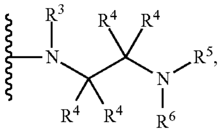

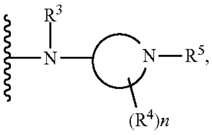

or

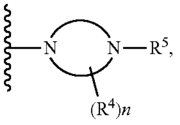

where

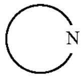

represents a 3- to 5-membered saturated monocyclic heterocyclic ring containing the illustrated nitrogen atom and optionally one additional heteroatom selected from the group consisting of O and S;

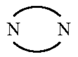

represents a 7- to 8-membered saturated monocyclic heterocyclic ring containing the illustrated nitrogen atoms and optionally one additional heteroatom selected from the group consisting of O and S;

$R^3$ is methyl;

each $R^4$ is independently selected from the group consisting of hydrogen, fluoro, $C_1$-$C_6$ alkyl, and $C_1$-$C_6$ fluoroalkyl, or alternatively, any two $R^4$ moieties, together with the carbon atom or atoms to which they are attached, form a cyclopropyl moiety or an aziridinyl moiety;

n is 0, 1, 2, or 3;

$R^5$ is hydrogen; and $R^6$ is hydrogen, or, when two $R^4$ moieties, together with the carbon atom or atoms to which they are attached, form a cyclopropyl moiety, $R^6$ is methyl, with the following provisos:

(a) when Z is

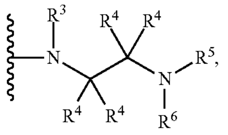

Z is not

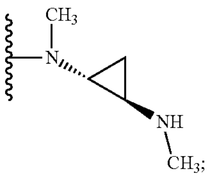 [SMILES: *N(C)[C@@H]1C[C@H]1NC]

(b) when Z is

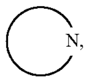

Z is not

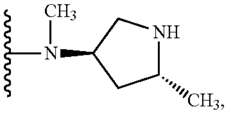

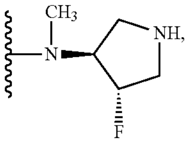

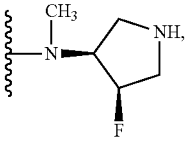

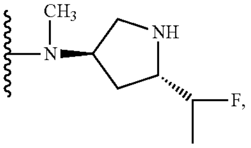

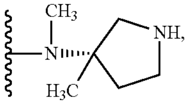

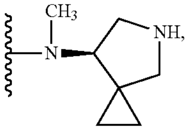

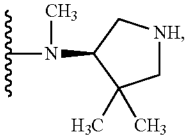

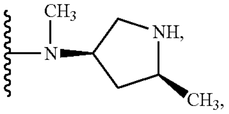

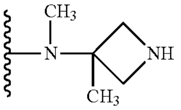

or

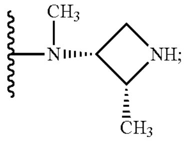

and (c) when Z is

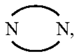

$R^4$ is not methyl.

In an embodiment of the compound of Formula (I) or a pharmaceutically acceptable salt thereof, ring $C^x$ is

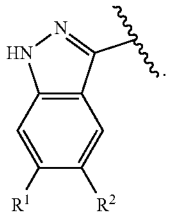

In an embodiment of the compound of Formula (I) or a pharmaceutically acceptable salt thereof, ring $C^x$ is

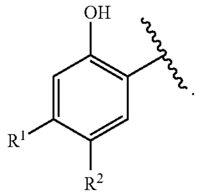

In an embodiment of the compound of Formula (I) or a pharmaceutically acceptable salt thereof, $R^1$ is chloro.

In an embodiment of the compound of Formula (I) or a pharmaceutically acceptable salt thereof, $R^2$ is tert-butyl.

In an embodiment of the compound of Formula (I) or a pharmaceutically acceptable salt thereof, $R^{A1}$ is methyl.

In an embodiment of the compound of Formula (I) or a pharmaceutically acceptable salt thereof, $R^{A1}$ is ring $C^{A1}$, and ring $C^{A1}$ is a substituted or unsubstituted 5- to 6-membered saturated monocyclic heterocyclic ring containing from 1 to 2 N heteroatoms. In a further embodiment, ring $C^{A1}$ is unsubstituted pyrrolidinyl or pyrrolidinyl substituted by one $C_1$-$C_6$ alkyl.

In an embodiment of the compound of Formula (I) or a pharmaceutically acceptable salt thereof, Z is

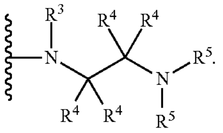

In a further embodiment, Z is

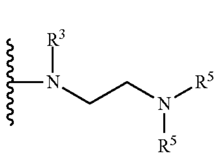

or

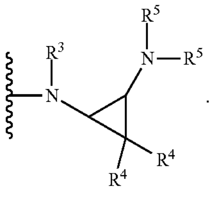

In an embodiment of the compound of Formula (I) or a pharmaceutically acceptable salt thereof, Z is

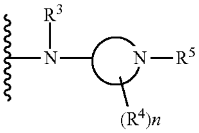

or

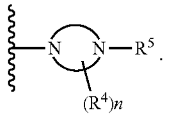

In a further embodiment, Z is

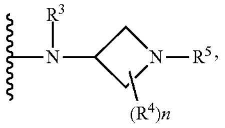

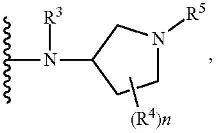

, or

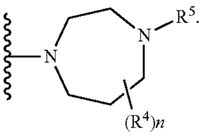

In an embodiment of the compound of Formula (I) or a pharmaceutically acceptable salt thereof, Z is

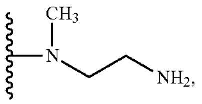

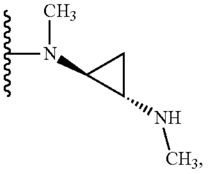

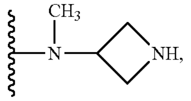

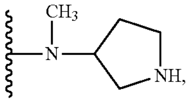

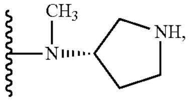

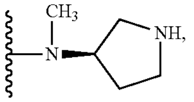

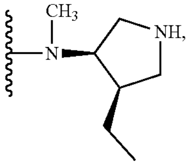

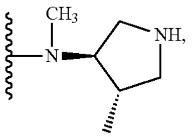

-continued
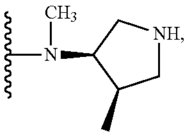
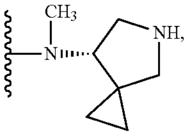
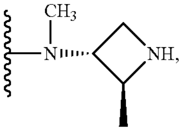
or
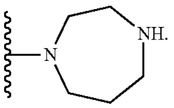
In an embodiment of the compound of Formula (I) or a pharmaceutically acceptable salt thereof, the compound of Formula (I) has the Formula (IA)
(IA)
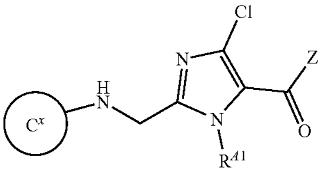
wherein
ring $C^x$ is
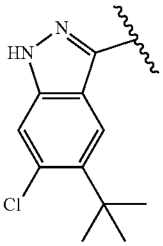
or
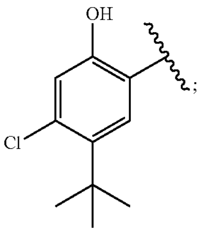
;
$R^{A1}$ is methyl or
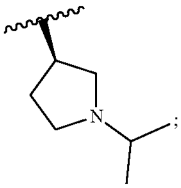 [SMILES: *[C@@H]1CCN(C(C)C)C1]
;
and
Z is selected from the group consisting of:
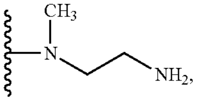
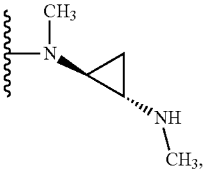
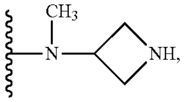
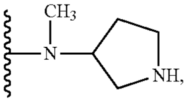
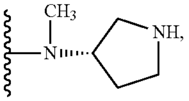
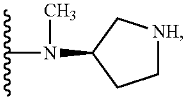
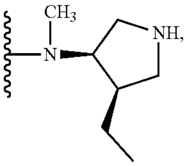
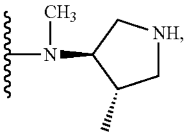
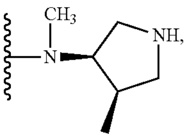
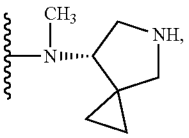
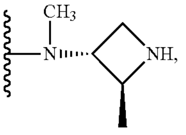
and
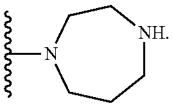

In a further embodiment, ring $C^x$ is

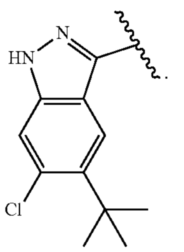

In an alternative further embodiment, ring $C^x$ is

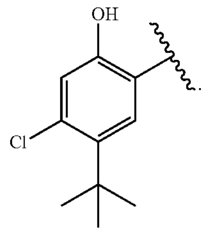 [SMILES: *c1cc(C(C)(C)C)c(Cl)cc1O]

In an embodiment of the compound of Formula (I) or a pharmaceutically acceptable salt thereof, the compound of Formula (I) is:

N-(azetidin-3-yl)-2-(((5-(tert-butyl)-6-chloro-1H-indazol-3-yl)amino)methyl)-4-chloro-N,1-dimethyl-1H-imidazole-5-carboxamide, (S)-2-(((5-(tert-butyl)-6-chloro-1H-indazol-3-yl)amino)methyl)-4-chloro-N,1-dimethyl-N-(pyrrolidin-3-yl)-1H-imidazole-5-carboxamide, (R)-2-(((5-(tert-butyl)-6-chloro-1H-indazol-3-yl)amino)methyl)-4-chloro-N,1-dimethyl-N-(pyrrolidin-3-yl)-1H-imidazole-5-carboxamide, (2-(((5-(tert-butyl)-6-chloro-1H-indazol-3-yl)amino)methyl)-4-chloro-1-methyl-1H-imidazol-5-yl)(1,4-diazepan-1-yl)methanone, 2-(((5-(tert-butyl)-6-chloro-1H-indazol-3-yl)amino)methyl)-4-chloro-1-((R)-1-isopropylpyrrolidin-3-yl)-N-methyl-N-((R)-pyrrolidin-3-yl)-1H-imidazole-5-carboxamide, (R)-N-(azetidin-3-yl)-2-(((5-(tert-butyl)-6-chloro-1H-indazol-3-yl)amino)methyl)-4-chloro-1-(1-isopropylpyrrolidin-3-yl)-N-methyl-1H-imidazole-5-carboxamide, N-(2-aminoethyl)-2-(((5-(tert-butyl)-6-chloro-1H-indazol-3-yl)amino)methyl)-4-chloro-N,1-dimethyl-1H-imidazole-5-carboxamide, (R)-N-(2-aminoethyl)-2-(((5-(tert-butyl)-6-chloro-1H-indazol-3-yl)amino)methyl)-4-chloro-1-(1-isopropylpyrrolidin-3-yl)-N-methyl-1H-imidazole-5-carboxamide, 2-(((5-(tert-butyl)-6-chloro-1H-indazol-3-yl)amino)methyl)-4-chloro-N-((3R,4R)-4-ethylpyrrolidin-3-yl)-N,1-dimethyl-1H-imidazole-5-carboxamide, (S)-2-(((5-(tert-butyl)-6-chloro-1H-indazol-3-yl)amino)methyl)-4-chloro-N,1-dimethyl-N-(5-azaspiro[2.4]heptan-7-yl)-1H-imidazole-5-carboxamide, 2-(((5-(tert-butyl)-6-chloro-1H-indazol-3-yl)amino)methyl)-4-chloro-N,1-dimethyl-N-(trans-(2-methylazetidin-3-yl)-1H-imidazole-5-carboxamide, 2-(((5-(tert-butyl)-6-chloro-1H-indazol-3-yl)amino)methyl)-4-chloro-N,1-dimethyl-N-((1S,2S)-2-(methylamino)cyclopropyl)-1H-imidazole-5-carboxamide, 2-(((5-(tert-butyl)-6-chloro-1H-indazol-3-yl)amino)methyl)-4-chloro-N,1-dimethyl-N-(trans-4-methylpyrrolidin-3-yl)-1H-imidazole-5-carboxamide, 2-(((5-(tert-butyl)-6-chloro-1H-indazol-3-yl)amino)methyl)-4-chloro-N,1-dimethyl-N-(cis-4-methylpyrrolidin-3-yl)-1H-imidazole-5-carboxamide, (R)-2-(((5-(tert-butyl)-4-chloro-2-hydroxyphenyl)amino)methyl)-4-chloro-N,1-dimethyl-N-(pyrrolidin-3-yl)-1H-imidazole-5-carboxamide, (S)-2-(((5-(tert-butyl)-4-chloro-2-hydroxyphenyl)amino)methyl)-4-chloro-N,1-dimethyl-N-(pyrrolidin-3-yl)-1H-imidazole-5-carboxamide, N-(azetidin-3-yl)-2-(((5-(tert-butyl)-4-chloro-2-hydroxyphenyl)amino)methyl)-4-chloro-N,1-dimethyl-1H-imidazole-5-carboxamide, 2-(((5-(tert-butyl)-4-chloro-2-hydroxyphenyl)amino)methyl)-4-chloro-1-((R)-1-isopropylpyrrolidin-3-yl)-N-methyl-N-((R)-pyrrolidin-3-yl)-1H-imidazole-5-carboxamide, 2-(((5-(tert-butyl)-4-chloro-2-hydroxyphenyl)amino)methyl)-4-chloro-1-((R)-1-isopropylpyrrolidin-3-yl)-N-methyl-N-((S)-pyrrolidin-3-yl)-1H-imidazole-5-carboxamide, (R)-N-(azetidin-3-yl)-2-(((5-(tert-butyl)-4-chloro-2-hydroxyphenyl)amino)methyl)-4-chloro-1-(1-isopropylpyrrolidin-3-yl)-N-methyl-1H-imidazole-5-carboxamide, and 2-(((5-(tert-butyl)-6-chloro-1H-indazol-3-yl)amino)methyl)-4-chloro-N,1-dimethyl-N-(pyrrolidin-3-yl)-1H-imidazole-5-carboxamide, or a pharmaceutically acceptable salt thereof.

Unless defined otherwise, all technical and scientific terms used herein have the same meaning as is commonly understood by one of skill in the art to which this invention belongs.

As used throughout this disclosure, "a compound of Formula (I)" is to be understood to include "a compound of Formula (I) or a pharmaceutically acceptable salt thereof".

As used herein, the wavy line ∿∿∿ indicates a point of attachment to the rest of a compound.

As used herein, "halo" refers to a halogen atom and includes chlorine, bromine, fluorine, and iodine.

As used herein, "alkyl" refers to a linear or branched saturated hydrocarbon group. Examples of alkyl include $C_1$-$C_6$ alkyl, such as methyl, ethyl, n-propyl, isopropyl, n-butyl, isobutyl, sec-butyl, tert-butyl, n-pentyl, isopentyl, and hexyl. "Alkyl" is preferably methyl, ethyl, n-propyl, isopropyl, n-butyl, isobutyl, or tert-butyl.

As used herein, "saturated monocyclic heterocyclic ring" refers to nonaromatic monocyclic ring structures in which one or more atoms in the ring, the heteroatom(s), is an element other than carbon. Heteroatoms are typically O, S or N atoms. Examples of saturated monocyclic heterocyclic ring groups include: piperidinyl, piperazinyl, morpholinyl, pyrrolidinyl, tetrahydrofuranyl, azetidinyl, oxiranyl, or aziridinyl, and the like. Some saturated monocyclic heterocyclic rings have 4-8 members and include 1-2 heteroatoms, while other saturated monocyclic heterocyclic rings have 3-5 members and include a nitrogen heteroatom and optionally one additional heteroatom, while still other saturated monocyclic heterocyclic rings have 7-8 members and include two nitrogen heteroatoms and optionally one additional heteroatom.

As used herein, "cycloalkyl" refers to a monocyclic saturated hydrocarbon. Examples of cycloalkyl include $C_3$-$C_6$ cycloalkyl, such as cyclopropyl, cyclobutyl, cyclopentyl, and cyclohexyl, with cyclopropyl, cyclobutyl, and cyclopentyl being preferable, and cyclopropyl and cyclobutyl being particularly preferable.

As used herein, "fluoroalkyl" refers to mono-substituted as well as multiple fluoro-substituted alkyl groups, up to perfluoro substituted alkyl. For example, fluoromethyl, 1,1-difluoroethyl, trifluoromethyl or 1,1,1,2,2-pentafluorobutyl are included.

As used herein, "pharmaceutically acceptable salt(s)" refers to salt(s) prepared from pharmaceutically acceptable non-toxic bases or acids.

When the compound of the present invention is acidic, its corresponding salt can be conveniently prepared from pharmaceutically acceptable non-toxic bases, including inorganic bases and organic bases. Salts derived from such inorganic bases include aluminum, ammonium, calcium, copper (ic and ous), ferric, ferrous, lithium, magnesium, manganese (ic and ous), potassium, sodium, zinc and the like salts. Preferred are the ammonium, calcium, magnesium, potassium and sodium salts. Salts prepared from pharmaceutically acceptable organic non-toxic bases include salts of primary, secondary, and tertiary amines derived from both naturally occurring and synthetic sources. Pharmaceutically acceptable organic non-toxic bases from which salts can be formed include, for example, arginine, betaine, caffeine, choline, N,N'-dibenzylethylenediamine, diethylamine, 2-diethylaminoethanol, 2-dimethylaminoethanol, ethanolamine, ethylenediamine, N-ethylmorpholine, N-ethylpiperidine, glucamine, glucosamine, histidine, hydrabamine, isopropylamine, dicyclohexylamine, lysine, methylglucamine, morpholine, piperazine, piperidine, polyamine resins, procaine, purines, theobromine, triethylamine, trimethylamine, tripropylamine, tromethamine and the like.

When the compound of the present invention is basic, its corresponding salt can be conveniently prepared from pharmaceutically acceptable non-toxic inorganic and organic acids. Such acids include, for example, acetic, benzenesulfonic, benzoic, camphorsulfonic, citric, ethanesulfonic, fumaric, gluconic, glutamic, hydrobromic, hydrochloric, isethionic, lactic, maleic, malic, mandelic, methanesulfonic, mucic, nitric, pamoic, pantothenic, phosphoric, succinic, sulfuric, tartaric, p-toluenesulfonic acid and the like. Preferred are citric, hydrobromic, hydrochloric, maleic, phosphoric, sulfuric, and tartaric acids. If the compounds of Formula (I) simultaneously contain acidic and basic groups in the molecule, the invention also includes, in addition to the salt forms mentioned, inner salts or betaines (zwitterions).

Salts can be obtained from the compounds of Formula (I) by customary methods which are known to the person skilled in the art, for example, by combination with an organic or inorganic acid or base in a solvent or dispersant, or by anion exchange or cation exchange from other salts. The present disclosure also includes all salts of the compounds of Formula (I) which, owing to low physiological compatibility, are not directly suitable for use in pharmaceuticals but which can be used, for example, as intermediates for chemical reactions or for the preparation of pharmaceutically acceptable salts.

As used herein, "KRAS G12D" or "KRAS G12D protein" refers to a mutant form of a mammalian KRAS protein that contains an amino acid substitution of an aspartic acid for a glycine at amino acid position 12. The assignment of amino acid codon and residue positions for human KRAS is based on the amino acid sequence identified by, for example, GenPept ID NP_004976. Compounds of Formula (I) are KRAS G12D inhibitors. Compounds of this disclosure are capable of negatively modulating or inhibiting all or a portion of the enzymatic activity of KRAS G12D. Without being bound to any specific theory, it is believed that the present KRAS G12D inhibitors bind to KRAS G12D by forming an ionic interaction with the aspartic acid at position 12 of inactive KRAS (GDP), thus preventing conversion of inactive KRAS (GDP) to active KRAS (GTP) and inhibiting downstream signaling.

In an embodiment, the compound of Formula (I) or the pharmaceutically acceptable salt thereof is used in the treatment of cancer.

Methods of Preparing the Compounds of Formula (I)

This disclosure also provides processes for the preparation of the compounds of Formula (I) which are described in the following and by which the compounds of the invention are obtainable.

Compounds of Formula (I) may be prepared from commercially available reagents using the synthetic methods and reaction schemes described herein, or using other reagents and conventional methods well known in the art, for example, through the following production methods or reaction steps described in the Examples. However, the production methods are not limited to these methods and reaction scheme as long as a product of interest can be obtained. An intermediate product or a final product obtained in each step can be subjected to the subsequent step after, or without, isolation and purification by known separation and purification methods, such as concentration, vacuum concentration, crystallization, solvent extraction, reprecipitation, and chromatography.

To the reaction product obtained in each step and the starting material, a protecting group that can be easily converted to the functional group can be introduced if it is effective in each step, or so as to change the order of the steps. Examples of the protecting group used herein may be the protecting groups, etc. used in the method disclosed in Greene's Protective Groups in Organic Synthesis, 5th edition, P.G.M. Wuts, John Wiley & Sons Inc. (2014). The protecting group may be appropriately selected according to the reaction conditions of each step. After introducing a protecting group and performing the reaction, the protecting group is optionally removed to thus yield a desired compound.

General Method A to Produce Compounds of Formula (I)

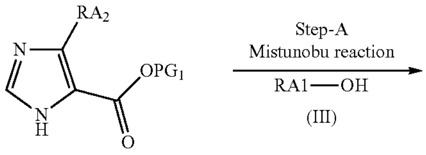

(II)

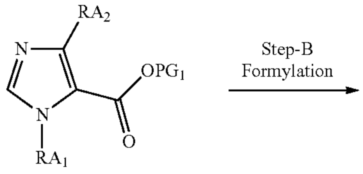

(IV)

-continued

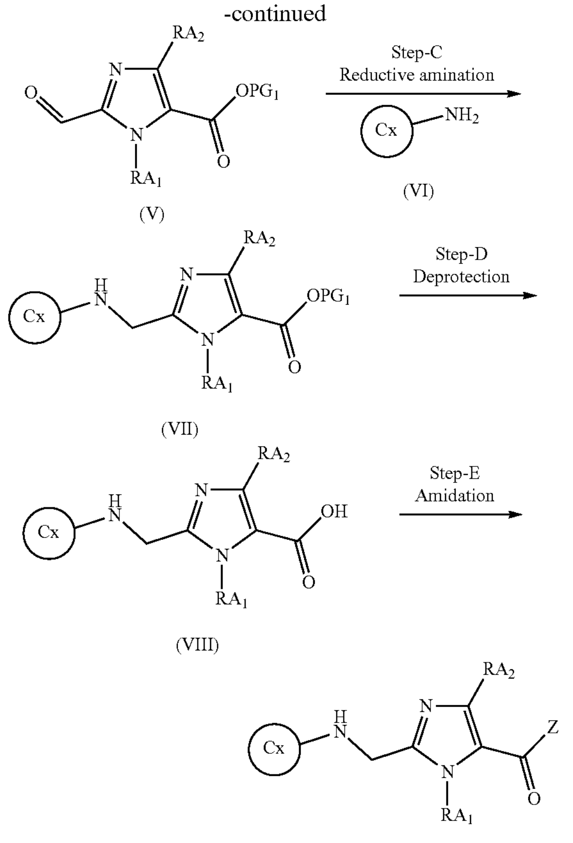

(V) (VI) (VII) (VIII) (I)

wherein $PG_1$ represents a protecting group and $R^{A1}$, $R^{A2}$, $C^X$, Z are as defined above.

In step A, a compound of Formula (II) is subjected to a Mitsunobu reaction with a compound of Formula (III) to produce a compound of Formula (IV). A Mitsunobu reaction well known in the field of organic chemistry is acceptable. The compounds of Formula (II) and the compounds of Formula (III) are either commercially available or may be prepared using methods identical to or analogous to those described in the Examples. The process typically comprises reacting a compound of Formula (II) with a compound of Formula (III) and suitable azodicarboxylate and suitable phosphine in a suitable solvent at a suitable temperature. An example of a suitable azodicarboxylate is DIAD (diisopropyl azodicarboxylate). An example of a suitable phosphine is triphenylphosphine. An example of a suitable solvent is THF (tetrahydrofuran). The amount of a compound of Formula (III) used herein is usually 1 to 100 moles, preferably 1 to 10 moles, per mole of the compound of Formula (II). The amount of the azodicarboxylate used is usually 1 to 100 moles, preferably 1 to 20 moles, per mole of the compound of Formula (II). The amount of the phosphine used is usually 1 to 100 moles, preferably 1 to 20 moles, per mole of the compound of Formula (II). The reaction temperature generally ranges from 0 to 100° C., preferably 0 to 60° C. The reaction time generally ranges from 5 minutes to 7 days, preferably 30 minutes to 4 days. The thus-obtained compound of Formula (IV) can be subjected to the subsequent step after or without isolation or purification by known separation and purification means, such as concentration, vacuum concentration, crystallization, solvent extraction, reprecipitation, and chromatography.

In step B, known reaction methods for introducing a formyl group may be used. For example, a method in which a strong base is used to generate anions, followed by reaction with a formylating agent. The process typically comprises reacting a compound of Formula (IV) with a suitable base and suitable formylating agent in a suitable solvent at a suitable temperature. Examples of a suitable strong base is 2,2,6,6-tetramethylpiperidinyl magnesium chloride and a lithium chloride complex. An example of a suitable formylating agent is DMF (N,N-dimethylformamide). An example of a suitable solvent is THF. The amount of a strong base used herein is usually 1 to 100 moles, preferably 1 to 10 moles, per mole of the compound of Formula (IV). The amount of the formylating agent used is usually 1 to 100 moles, preferably 1 to 20 moles, per mole of the compound of Formula (IV). The reaction temperature generally ranges from −78° C. to 0° C. The reaction time generally ranges from 5 minutes to 7 days, preferably 30 minutes to 4 days. A thus-obtained compound of Formula (V) can be subjected to the subsequent step after or without isolation or purification by known separation and purification means, such as concentration, vacuum concentration, crystallization, solvent extraction, reprecipitation, and chromatography.

In step C, the compound of Formula (V) is subjected to a reductive amination with the compound of Formula (VI) to produce a compound of Formula (VII). A reductive amination well known in the field of organic chemistry is acceptable. The compounds of Formula (VI) are either commercially available or may be prepared using methods identical to or analogous to those described in the Examples. The process typically comprises reacting a compound of Formula (V) with a compound of Formula (VI) and suitable reducing agent and suitable acid in a suitable solvent at a suitable temperature. An example of a suitable reducing agent is triacetoxyborohydride. An example of a suitable acid is trifluoroacetic acid. An example of a suitable solvent is THF. The amount of a reducing agent used herein is usually 1 to 100 moles, preferably 1 to 10 moles, per mole of the compound of Formula (V). The amount of the acid agent used is usually 5 to 100 moles, preferably 5 to 20 moles, per mole of the compound of Formula (V). The reaction temperature generally ranges from 0 to 100° C., preferably 0 to 60° C. The reaction time generally ranges from 5 minutes to 7 days, preferably 30 minutes to 4 days. A thus-obtained compound of Formula (VII) can be subjected to the subsequent step after or without isolation or purification by known separation and purification means, such as concentration, vacuum concentration, crystallization, solvent extraction, reprecipitation, and chromatography.

In step D, the compound of Formula (VII) is subjected to a hydrolysis reaction of carboxylate to produce a compound of Formula (VIII). A hydrolysis reaction of carboxylate well known in the field of organic chemistry is acceptable. The process typically comprises reacting a compound of Formula (VII) with a suitable base in a suitable solvent at a suitable temperature. An example of a suitable base is sodium hydroxide. An example of a suitable solvent is ethanol. The amount of a base used herein is usually 1 to 100 moles, preferably 10 to 30 moles, per mole of the compound of Formula (VII). The reaction temperature generally ranges from 0 to 100° C., preferably 0 to 60° C. The reaction time generally ranges from 5 minutes to 7 days, preferably 30 minutes to 4 days. The thus-obtained compound of Formula (VIII) can be subjected to the subsequent step after or without isolation or purification by known separation and purification means, such as concentration, vacuum concentration, crystallization, solvent extraction, reprecipitation, and chromatography.

In step E, the compound of Formula (VIII) is subjected to a condensation reaction with the amines corresponding to Z, as described above with respect to the compound of Formula (I), to produce the compound of Formula (I). A condensation reaction well known in the field of organic chemistry is acceptable. The amines are either commercially available or may be prepared using methods identical to or analogous to those described in the Examples. The process typically comprises reacting a compound of Formula (VIII) with an amine corresponding to Z and a suitable coupling reagent and a suitable base in a suitable solvent at a suitable temperature. An example of a suitable coupling reagent is HATU (1-[bis(dimethylamino)methylene]-1H-1,2,3-triazole [4,5-b]pyridinium-3-oxidehexafluorophosphate). An example of a suitable base is DIPEA (N,N-diisopropylethylamine). An example of a suitable solvent is DMF. The amount of a coupling reagent used herein is usually 1 to 100 moles, preferably 1 to 10 moles, per mole of the compound of Formula (VIII). The amount of a base used herein is usually 1 to 100 moles, preferably 3 to 30 moles, per mole of the compound of Formula (VIII). The reaction temperature generally ranges from 0 to 100° C., preferably 0 to 60° C. The reaction time generally ranges from 5 minutes to 7 days, preferably 30 minutes to 4 days. The thus-obtained compound of Formula (I) can be subjected to the subsequent step after or without isolation or purification by known separation and purification means, such as concentration, vacuum concentration, crystallization, solvent extraction, reprecipitation, and chromatography.

General Method B to Produce Compounds of Formula (XI)

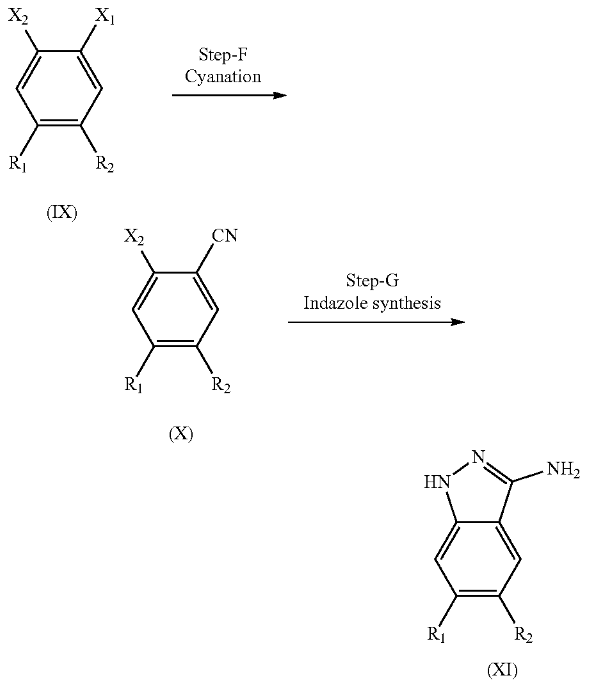

(IX) (X) (XI)

wherein $X_1$ is a substituent that is convertible into cyano or the like. Examples of $X_1$ include halogen, amine, ester, amide, carboxylic acid, and the like. $X_2$ is a substituent that is convertible into hydrazine or the like. Examples of $X_2$ include a protector, etc. for halogen, amine, and hydrazine. $R_1$ and $R_2$ are as defined above with respect to the compound of Formula (I).

A compound of Formula (IX), which can be synthesized by known methods, is subjected to a cyanation reaction of step F to obtain a compound of Formula (X), and then the obtained compound is subjected to an indazole cyclization reaction of step G to thus produce a compound of Formula (XI).

In step F, a method well known in the field of organic chemistry is used to introduce a cyano group. For example, when $X_1$ in the compound of Formula (IX) is an amino group, a diazotization agent is used at −20° C. to room temperature in an appropriate solvent to prepare a diazonium salt, and the obtained diazonium salt is added at −20 to 100° C. to a solution of a base and a cyanating agent. Examples of suitable reaction solvents include acidic solvents, such as hydrochloric acid, acetic acid, trifluoroacetic acid, and sulfuric acid, alcohols, such as methanol and ethanol, water, and mixtures thereof. Examples of the diazotization agent include sodium nitrite, isopentyl nitrite, and the like. Examples of the base include sodium hydroxide, sodium carbonate, sodium hydrogen carbonate, and the like. Examples of the cyanating agent include sodium cyanide, potassium cyanide, copper cyanide, zinc cyanide, and the like, and mixtures thereof. Further, for example, when $X_1$ in a compound of Formula (IX) is halogen, the reaction may also be performed at room temperature to 200° C. using a cyanating agent in an appropriate solvent. In the reaction, a palladium catalyst, etc. may be added. Examples of the cyanating agent include sodium cyanide, potassium cyanide, copper cyanide, zinc cyanide, and the like, and mixtures thereof. The usable reaction solvent is not limited as long as it does not affect the reaction. Examples include ethers, such as THE and 1,4-dioxane, alcohols, such as methanol and ethanol, amides, such as DMF, N,N-dimethylacetamide, and N-methyl-2-pyrrolidone, hydrocarbons, such as toluene, acetonitrile, dimethylsulfoxide, water, and mixed solvents thereof.

In step G, for example, when $X_2$ in a compound of Formula (X) is halogen, hydrazine, etc. may be reacted at 20 to 200° C. in an appropriate solvent. It is also possible to subject hydrazine, etc. protected by a protecting group to a cross-coupling reaction using a palladium catalyst, and thereafter remove the hydrazine protecting group. The reaction solvent useful here is not limited as long as it does not affect the reaction. Examples include ethers, such as THE and 1,4-dioxane, alcohols, such as methanol and ethanol, amides, such as DMF, N,N-dimethylacetamide, and N-methyl-2-pyrrolidone, hydrocarbons, such as toluene, acetonitrile, dimethylsulfoxide, water, and mixed solvents thereof. Examples of the palladium catalyst useful here include palladium acetate, palladium chloride, tetrakis(triphenylphosphine)palladium, dichlorobis(triphenylphosphine)palladium, dichloro(1,1'-bis(diphenylphosphino)ferrocene)palladium, dichlorobisacetonitrile palladium, and tris(dibenzylideneacetone) dipalladium (0). It is appropriate to use the palladium catalyst in an amount of 0.001 to 1 mol, per mol of the compound of Formula (X). As a ligand of palladium, it is possible to use 1-1'-bis(diphenylphosphino) ferrocene, 4,5-bis(diphenylphosphino)-9,9'-dimethylxanthene, 2-dicyclohexylphosphino-2',4',6'-triisopropylbiphenyl, 2-dicyclohexylphosphino-2',6'-dimethoxybiphenyl, 2-di-tert-butylphosphino-3,4,5,6-tetramethyl-2',4',6'-triisopropylbiphenyl, and the like, if necessary. In this step, it is possible to use a base. Examples include organic bases, such as potassium-tert-butyrate, sodium-tert-butyrate, sodium methoxide, sodium ethoxide, lithium hexamethyldisilazide, sodium hexamethyldisilazide, and potassium hexamethyldisilazide, and inorganic bases, such as sodium carbonate, potassium carbonate, cesium carbonate, sodium hydroxide, sodium phosphate, and potassium phosphate. Although it varies depending on the reaction temperature, the reaction may be performed for 30 minutes to 24 hours. The hydrazine protecting group may be removed, for example, by the method disclosed in Greene's Protective Groups in Organic Synthesis, 5th edition, P.G.M. Wuts, John Wiley & Sons Inc. (2014), or a similar method, although it varies depending on the type of the protecting group used.

Methods of Using the Compounds of Formula (I)

This disclosure also provides a method of inhibiting KRAS G12D protein comprising contacting KRAS G12D protein with a compound of Formula (I) or a pharmaceutically acceptable salt thereof, to inhibit the activity of the KRAS G12D protein. In some embodiments, KRAS G12D is inhibited by contacting the KRAS G12D protein with an effective amount of a compound of Formula (I). In some embodiments, KRAS G12D protein activity is inhibited by contacting a cell, tissue, or organ that expresses KRAS G12D protein with an effective amount of a compound of Formula (I). In some embodiments, KRAS G12D protein is inhibited in a subject by administering to the subject an effective amount of a compound of Formula (I).

This disclosure also provides a method of treating disease conditions, including but not limited to, conditions implicated by KRAS G12D mutation, comprising administering a therapeutically effective amount of a compound of Formula (I) or a pharmaceutically acceptable salt thereof to a subject in need of such treatment. Such disease conditions include cancer.

As used herein, "inhibit the activity of the KRAS G12D protein" refers to negatively modulating or inhibiting all or a portion of the enzymatic activity of KRAS G12D. In an embodiment, "inhibit the activity of the KRAS G12D protein" refers to preventing conversion of inactive KRAS (GDP) to active KRAS (GTP) and inhibiting downstream signaling.

As used herein, "treat" or "treatment" includes treating for the purpose of curing or ameliorating cancer, or for the purpose of suppressing the progression, occurrence, or recurrence of the cancer or alleviating symptoms.

As used herein, a "therapeutically effective amount" refers to an amount of a pharmaceutically active agent, e.g., a KRAS G12D inhibitor, that will elicit the biological or medical response of a tissue, system, animal or human that is being sought by a researcher, veterinarian, medical doctor or other clinician. In an embodiment, "therapeutically effective amount" means an amount of a pharmaceutically active agent that alleviates at least one clinical symptom in a human patient. In an embodiment, the "therapeutically effective amount" may also be a "prophylactically effective amount", i.e., an amount sufficient to prevent a cancer. In an embodiment, the "therapeutically effective amount" coincides with a daily dosage as defined below.

As used herein, "effective amount" refers to an amount of a compound of Formula (I) sufficient to achieve a reduction or prevention of an activity of enzyme or protein. In an embodiment, the "effective amount" is a "therapeutically effective amount".

As used herein, "subject" includes animals, both mammals and nonmammals, and preferably humans. In an embodiment, the subject is a human patient and may be a human who has been diagnosed to need a treatment for a clinical symptom or medical state associated with cancer as disclosed herein. In an embodiment, the subject has been identified or diagnosed as having a cancer having a KRAS G12D mutation. In an embodiment, the subject has a tumor that is positive for a KRAS G12D mutation. The subject may be in need of, or desire, treatment for an existing cancer or may be in need of or desire prophylactic treatment to prevent or reduce the risk of occurrence of cancer. As used herein, a subject "in need" of treatment of an existing cancer or of prophylactic treatment encompasses both a determination of need by a medical professional as well as the desire of a patient for such treatment.

Cancer, in accordance with the present disclosure includes, but is not limited to, glandular tumors, carcinoid tumors, undifferentiated carcinomas, angiosarcoma, adenocarcinoma, gastrointestinal cancers (e.g., colorectal cancers ("CRC") including colon cancer and rectal cancer, biliary cancers including gall bladder cancer and bile duct cancer, anal cancer, esophageal cancer, gastric (stomach) cancer, gastrointestinal carcinoid tumor(s), gastrointestinal stromal tumor(s) ("GIST"), liver cancer, duodenal cancer and small intestine cancer), lung cancers (e.g., non-small cell lung cancer ("NSCLC"), squamous-cell lung carcinoma, large-cell lung carcinoma, small cell lung carcinoma, mesothelioma and other lung cancers such as bronchial tumors and pleuropulmonary blastoma), urological cancers (e.g., kidney (renal) cancer, transitional cell cancer ("TCC") of kidney, TCC of the renal pelvis and ureter ("PDQ"), bladder cancer, urethral cancer and prostate cancer), head and neck cancers (e.g., eye cancer, retinoblastoma, intraocular melanoma, hypopharyngeal cancer, pharyngeal cancer, laryngeal cancer, laryngeal papillomatosis, metastatic squamous neck cancer with occult primary, oral (mouth) cancer, lip cancer, throat cancer, oropharyngeal cancer, esthesioneuroblastoma, nasal cavity and paranasal sinus cancer, nasopharyngeal cancer, and salivary gland cancer), endocrine cancers (e.g., thyroid cancer, parathyroid cancer, multiple endocrine neoplasia syndromes, thymoma and thymic carcinoma, pancreatic cancers including pancreatic ductal adenocarcinoma ("PDAC"), pancreatic neuroendocrine tumors and islet cell tumors), breast cancers (extrahepatic ductal carcinoma in situ ("DCIS"), lobular carcinoma in situ ("LCIS"), triple negative breast cancer, and inflammatory breast cancer), male and female reproductive cancers (e.g., cervical cancer, ovarian cancer, endometrial cancer, uterine sarcoma, uterine cancer, vaginal cancer, vulvar cancer, gestational trophoblastic tumor ("GTD"), extragonadal germ cell tumor, extracranial germ cell tumor, germ cell tumor, testicular cancer and penile cancer), brain and nervous system cancers (e.g., astrocytomas, brain stem glioma, brain tumor, craniopharyngioma, central nervous system ("CNS") cancer, chordomas, ependymoma, embryonal tumors, neuroblastoma, paraganglioma and atypical teratoid), skin cancers (e.g., basal cell carcinoma ("BCC"), squamous cell skin carcinoma ("SCC"), Merkel cell carcinoma and melanoma), tissue and bone cancers (e.g., soft-tissue sarcoma, rhabdomyosarcoma, fibrous histiocytoma of bone, Ewing sarcoma, malignant fibrous histiocytoma of bone ("MFH"), osteosarcoma and chondrosarcoma), cardiovascular cancers (e.g., heart cancer and cardiac tumors), appendix cancers, childhood and adolescent cancers (e.g., adrenocortical carcinoma childhood, midline tract carcinoma, hepatocellular carcinoma ("HCC"), hepatoblastoma and Wilms' tumor) and viral-induced cancers (e.g., HHV-8 related cancers (Kaposi sarcoma) and HIV/AIDS related cancers). In some embodiments, the cancer is lung cancer, pancreatic cancer, or colorectal cancer.

Cancer, in accordance with the present disclosure also includes, but is not limited to, hematological and plasma cell malignancies (e.g., cancers that affect blood, bone marrow and/or lymph nodes) such as multiple myeloma, leukemias and lymphomas, myelodysplastic syndromes and myeloproliferative disorders. Leukemias include, without limitation, acute lymphoblastic leukemia ("ALL"), acute myelogenous (myeloid) leukemia ("AML"), chronic lymphocytic leukemia ("CLL"), chronic myelogenous leukemia ("CML"), acute monocytic leukemia ("AMoL"), hairy cell leukemia, and/or other leukemias. Lymphomas include, without limitation, Hodgkin's lymphoma and non-Hodgkin's lymphoma ("NHL"). In some embodiments, NHL is B-cell lymphomas and/or T-cell lymphomas. In some embodiments, NHL includes, without limitation, diffuse large B-cell lymphoma ("DLBCL"), small lymphocytic lymphoma ("SLL"), chronic lymphocytic leukemia ("CLL"), mantle cell lymphoma ("MCL"), Burkitt's lymphoma, cutaneous T-cell lymphoma including mycosis fungoides and Sézary syndrome, AIDS-related lymphoma, follicular lymphoma, lymphoplasmacytic lymphoma (Waldenstrom's macroglobulinemia ("WM")), primary central nervous system (CNS) lymphoma and/or other lymphomas.

Dosing and Administration

A specific dosage regimen utilizing a compound of Formula (I) is selected in accordance with a variety of factors including type, species, age, weight, sex and medical condition of the subject, the severity of the condition to be treated, the potency of the compound chosen to be administered, the route of administration, and the renal and hepatic function of a subject. A consideration of these factors is well within the purview of the ordinarily skilled clinician for the purpose of determining the therapeutically effective amount needed to prevent, counter, or arrest the progress of the cancer. It is understood that a specific daily dosage amount can simultaneously be both a therapeutically effective amount, e.g., for treatment of an oncological condition, and a prophylactically effective amount, e.g., for prevention of an oncological condition.

While individual needs vary, determination of optimal ranges of effective amounts of the compound of Formula (I) is within the skill of the art. For administration to a human in the treatment or prophylaxis of cancer, for example, typical daily dosages of the compounds of Formula (I) can be about 0.05 mg/kg/day to about 50 mg/kg/day, for example at least 0.05 mg/kg, at least 0.08 mg/kg, at least 0.1 mg/kg, at least 0.2 mg/kg, at least 0.3 mg/kg, at least 0.4 mg/kg, or at least 0.5 mg/kg, and preferably 50 mg/kg or less, 40 mg/kg or less, 30 mg/kg or less, 20 mg/kg or less, or 10 mg/kg or less, which can be about 2.5 mg/day (0.5 mg/kg x 5 kg) to about 5000 mg/day (50 mg/kg x 100 kg), for example. For example, dosages of the compounds can be about 0.1 mg/kg/day to about 50 mg/kg/day, about 0.05 mg/kg/day to about 10 mg/kg/day, about 0.05 mg/kg/day to about 5 mg/kg/day, about 0.05 mg/kg/day to about 3 mg/kg/day, about 0.07 mg/kg/day to about 3 mg/kg/day, about 0.09 mg/kg/day to about 3 mg/kg/day, about 0.05 mg/kg/day to about 0.1 mg/kg/day, about 0.1 mg/kg/day to about 1 mg/kg/day, about 1 mg/kg/day to about 10 mg/kg/day, about 1 mg/kg/day to about 5 mg/kg/day, about 1 mg/kg/day to about 3 mg/kg/day, about 3 mg/day to about 500 mg/day, about 5 mg/day to about 250 mg/day, about 10 mg/day to about 100 mg/day, about 3 mg/day to about 10 mg/day, or about 100 mg/day to about 250 mg/day. Such doses may be administered in a single dose or may be divided into multiple doses.

The compounds of Formula (I) and their pharmaceutically acceptable salts can be administered to a subject as pharmaceutically active agents by themselves, in mixtures with one another, or in the form of pharmaceutical compositions (described below). Administration includes both self-administration and administration to the patient by another person.

Administration can be orally, for example, in the form of pills, tablets, coated tablets, lacquered tablets, sugar-coated tablets, granules, powders, hard and soft gelatin capsules, aqueous, alcoholic or oily solutions, syrups, emulsions or suspensions; rectally, for example, in the form of suppositories; parenterally, for example, subcutaneously, intramuscularly or intravenously in the form of solutions for injection or infusion; percutaneously or topically, for example, in the form of ointments, tinctures, sprays or transdermal therapeutic systems, or, for example, microcapsules, implants or rods or inhalations. The preferred administration form depends, for example, on the cancer to be treated and on its severity.

Pharmaceutical Compositions Containing Compounds of Formula (I)

This disclosure further provides a pharmaceutical composition comprising a compound of Formula (I) or a pharmaceutically acceptable salt thereof and a pharmaceutically acceptable carrier. In an embodiment, more than one compound of Formula (I) may be included in the pharmaceutical composition. In an embodiment, more than one pharmaceutically acceptable carrier may be included in the pharmaceutical composition. In an embodiment, the pharmaceutical composition is used in the treatment of cancer. In an embodiment, the pharmaceutical composition is suitable for oral administration.

In an embodiment, the compound of Formula (I) is present in a therapeutically effective amount. The amount of the compound of Formula (I) or a pharmaceutically acceptable salt thereof in the pharmaceutical composition typically is from 0.01 to 200 mg, such as from 0.1 to 200 mg, preferably from 1 to 200 mg, per dose, but depending on the type of pharmaceutical composition, it can also be higher. In some embodiments, the amount of the compound of Formula (I) or a pharmaceutically acceptable salt thereof in the pharmaceutical composition is from 0.01 to 10 mg per dose. The pharmaceutical compositions typically comprise 0.5 to 90 percent by weight of the compound of Formula (I) or a pharmaceutically acceptable salt thereof.

Pharmaceutical compositions according to the disclosure can be made according to any known or conventional technique. Formulating such pharmaceutical compositions is well within the purview of the ordinarily skilled formulator. As such a formulator would readily recognize, suitable pharmaceutically acceptable carriers for a given pharmaceutical composition will vary, depending on the dosage form desired. Pharmaceutically acceptable carriers include, without limitation, various conventional organic or inorganic carrier materials which can be used as, e.g., excipients, binders, solvents, etc.

For the production of pills, tablets, sugar-coated tablets and hard gelatin capsules, for example, it is possible to use lactose, starch, starch derivatives, talc, stearic acid or its salts, etc. Carriers for soft gelatin capsules and suppositories include, without limitation, fats, waxes, semisolid and liquid polyols, natural or hardened oils, etc. Suitable carriers for the preparation of solutions, emulsions or syrups include, for example, water, physiologically acceptable sodium chloride solution, alcohols such as ethanol, glycerol, polyols, sucrose, invert sugar, glucose, mannitol, vegetable oils, etc. It is also possible to lyophilize the compounds of Formula (I)

and to use the resulting lyophilisates, for example, for preparing preparations for injection or infusion. Suitable carriers for microcapsules, implants or rods are, for example, copolymers of glycolic acid and lactic acid.

The pharmaceutical compositions of the disclosure may further contain one or more additives. Suitable additives include materials which act as fillers, disintegrants, binders, lubricants, wetting agents, stabilizers, emulsifiers, dispersants, preservatives, sweeteners, colorants, flavorings, aromatizers, thickeners, diluents, buffer substances, solvents, solubilizers, agents for achieving a depot effect, salts for altering the osmotic pressure, coating agents, antioxidants, suspending agents, isotonizing agents, soothing agents, anesthetics, and antiseptics. A formulator of ordinary skill can readily incorporate one or more additives in a pharmaceutical composition, depending on factors such as the cancer being treated, the patient, and the desired dosage form.

Combinations

The compounds of Formula (I) can be used to treat cancer in combination with one or more additional active agents. In other words, a single compound of Formula (I) or more than one compound of Formula (I) may be used in combination with a single additional active agent or more than one additional active agents.

As used herein, an "additional active agent" can be any pharmaceutically active agent (or pharmaceutically acceptable salt thereof) that is active in the body and that is different from the compound of Formula (I). The additional active agents include prodrugs, free-acid, free-base and pharmaceutically acceptable salts of the additional active agents. Generally any suitable additional active agent, including chemotherapeutic agents or therapeutic antibodies, may be used in any combination with a compound of Formula (I) in a single dosage formulation (e.g., a fixed dose drug combination) or in one or more separate dosage formulations which allow for concurrent or sequential administration of the pharmaceutically active agents (co-administration of the separate active agents) to subjects. In certain embodiments, a compound of Formula (I) and an additional active agent are administered a few minutes apart, or a few hours apart, or a few days apart. In addition, the compounds of Formula (I) can be administered in combination with radiation therapy, hormone therapy, targeted therapy, surgery or immunotherapy. In one embodiment, the one or more additional active agents are included in a pharmaceutical composition as described above.

In one embodiment, the additional active agent(s) is an additional anti-cancer agent (also known as an antineoplastic agent). As used herein, an "anti-cancer agent" is any pharmaceutically active agent (or pharmaceutically active salt thereof) that is active in the body against cancer. Examples of anti-cancer agents include chemotherapeutic agents (e.g., cytotoxic agents), immunotherapeutic agents, hormonal and anti-hormonal agents, targeted therapy agents, and anti-angiogenesis agents. Many anti-cancer agents can be classified within one or more of these groups. While certain anti-cancer agents have been categorized within a specific group(s) or subgroup(s) herein, many of these agents can also be listed within one or more other group(s) or subgroup(s), as would be presently understood in the art. It is to be understood that the classification herein of a particular agent into a particular group is not intended to be limiting. Many anti-cancer agents are presently known in the art and can be used in combination with the compounds of the present disclosure.

Further, an agent can be an agonist, antagonist, allosteric modulator, toxin or, more generally, may act to inhibit or stimulate its target (e.g., receptor or enzyme activation or inhibition). For example, suitable for use are one or more agents (e.g., antibodies, antigen binding regions, or soluble receptors) that specifically bind and inhibit the activity of growth factors, such as antagonists of hepatocyte growth factor (HGF, also known as Scatter Factor), and antibodies or antigen binding regions that specifically bind its receptor "c-met".

In an embodiment, the additional anti-cancer agent is a chemotherapeutic agent, an immunotherapeutic agent, a hormonal agent, an anti-hormonal agent, a targeted therapy agent, or an anti-angiogenesis agent (or angiogenesis inhibitor). In an embodiment, the additional anti-cancer agent is selected from the group consisting of a chemotherapeutic agent, a mitotic inhibitor, a plant alkaloid, an alkylating agent, an anti-metabolite, a platinum analog, an enzyme, a topoisomerase inhibitor, a retinoid, an aziridine, an antibiotic, a hormonal agent, an anti-hormonal agent, an anti-estrogen, an anti-androgen, an anti-adrenal, an androgen, a targeted therapy agent, an immunotherapeutic agent, a biological response modifier, a cytokine inhibitor, a tumor vaccine, a monoclonal antibody, an immune checkpoint inhibitor, an anti-PD-1 agent, an anti-PD-L1 agent, a colony-stimulating factor, an immunomodulator, an immunomodulatory imide (IMiD), an anti-CTLA4 agent, an anti-LAG1 agent, an anti-OX40 agent, a GITR agonist, a CAR-T cell, a BiTE, a signal transduction inhibitor, a growth factor inhibitor, a tyrosine kinase inhibitor, an EGFR inhibitor, a histone deacetylase (HDAC) inhibitor, a proteasome inhibitor, a cell-cycle inhibitor, an anti-angiogenesis agent, a matrix-metalloproteinase (MMP) inhibitor, a hepatocyte growth factor inhibitor, a TOR inhibitor, a KDR inhibitor, a VEGF inhibitor, a HIF-1α inhibitor a HIF-2α inhibitor, a fibroblast growth factor (FGF) inhibitor, a RAF inhibitor, a MEK inhibitor, an ERK inhibitor, a PI3K inhibitor, an AKT inhibitor, an MCL-1 inhibitor, a BCL-2 inhibitor, an SHP2 inhibitor, a HER-2 inhibitor, a BRAF-inhibitor, a gene expression modulator, an autophagy inhibitor, an apoptosis inducer, an antiproliferative agent, and a glycolysis inhibitor.

In one embodiment, the additional anti-cancer agent(s) is a chemotherapeutic agent. Non-limiting examples of chemotherapeutic agents include mitotic inhibitors and plant alkaloids, alkylating agents, anti-metabolites, platinum analogs, enzymes, topoisomerase inhibitors, retinoids, aziridines, and antibiotics.

Non-limiting examples of mitotic inhibitors and plant alkaloids include taxanes such as cabazitaxel, docetaxel, larotaxel, ortataxel, paclitaxel, and tesetaxel; demecolcine; epothilone; eribulin; etoposide (VP-16); etoposide phosphate; navelbine; noscapine; teniposide; thaliblastine; vinblastine; vincristine; vindesine; vinflunine; and vinorelbine.

Non-limiting examples of alkylating agents include nitrogen mustards such as chlorambucil, chlornaphazine, cholophosphamide, cytophosphane, estramustine, ifosfamide, mannomustine, mechlorethamine, mechlorethamine oxide hydrochloride, melphalan, novembichin, phenesterine, prednimustine, tris(2-chloroethyl)amine, trofosfamide, and uracil mustard; alkyl sulfonates such as busulfan, improsulfan, and piposulfan; nitrosoureas such as carmustine, chlorozotocin, fotemustine, lomustine, nimustine, ranimustine, streptozotocin, and TA-07; ethylenimines and methylamelamines such as altretamine, thiotepa, triethylenemelamine, triethylenethiophosphaoramide, trietylenephosphoramide, and trimethylolomelamine; ambamustine; bendamustine; dacarbazine; etoglucid; irofulven; mafosfamide; mitobronitol; mitolactol; pipobroman; procarbazine; temozolomide; treosulfan; and triaziquone.

Non-limiting examples of anti-metabolites include folic acid analogues such as aminopterin, denopterin, edatrexate, methotrexate, pteropterin, raltitrexed, and trimetrexate; purine analogs such as 6-mercaptopurine, 6-thioguanine, fludarabine, forodesine, thiamiprine, and thioguanine; pyrimidine analogs such as 5-fluorouracil (5-FU), 6-azauridine, ancitabine, azacytidine, capecitabine, carmofur, cytarabine, decitabine, dideoxyuridine, doxifluridine, doxifluridine, enocitabine, floxuridine, galocitabine, gemcitabine, and sapacitabine; 3-aminopyridine-2-carboxaldehyde thiosemicarbazone; broxuridine; cladribine; cyclophosphamide; cytarabine; emitefur; hydroxyurea; mercaptopurine; nelarabine; pemetrexed; pentostatin; tegafur; and troxacitabine.

Non-limiting examples of platinum analogs include carboplatin, cisplatin, dicycloplatin, heptaplatin, lobaplatin, nedaplatin, oxaliplatin, satraplatin, and triplatin tetranitrate.

Non-limiting examples of enzymes include asparaginase and pegaspargase.

Non-limiting examples of topoisomerase inhibitors include acridine carboxamide, amonafide, amsacrine, belotecan, elliptinium acetate, exatecan, indolocarbazole, irinotecan, lurtotecan, mitoxantrone, razoxane, rubitecan, SN-38, sobuzoxane, and topotecan.

Non-limiting examples of retinoids include alitretinoin, bexarotene, fenretinide, isotretinoin, liarozole, RII retinamide, and tretinoin.

Non-limiting examples of aziridines include benzodopa, carboquone, meturedopa, and uredopa.

Non-limiting examples of antibiotics include intercalating antibiotics; anthracenediones; anthracycline antibiotics such as aclarubicin, amrubicin, daunomycin, daunorubicin, doxorubicin, epirubicin, idarubicin, menogaril, nogalamycin, pirarubicin, and valrubicin; 6-diazo-5-oxo-L-norleucine; aclacinomysins; actinomycin; authramycin; azaserine; bleomycins; cactinomycin; calicheamicin; carabicin; carminomycin; carzinophilin; chromomycins; dactinomycin; detorubicin; esorubicin; esperamicins; geldanamycin; marcellomycin; mitomycins; mitomycin C; mycophenolic acid; olivomycins; novantrone; peplomycin; porfiromycin; potfiromycin; puromycin; quelamycin; rebeccamycin; rodorubicin; streptonigrin; streptozocin; tanespimycin; tubercidin; ubenimex; zinostatin; zinostatin stimalamer; and zorubicin.

In one embodiment, the additional anti-cancer agent(s) is a hormonal and/or anti-hormonal agent (i.e., hormone therapy). Non-limiting examples of hormonal and anti-hormonal agents include anti-androgens such as abiraterone, apalutamide, bicalutamide, darolutamide, enzalutamide, flutamide, goserelin, leuprolide, and nilutamide; anti-estrogens such as 4-hydroxy tamoxifen, aromatase inhibiting 4(5)-imidazoles, EM-800, fosfestrol, fulvestrant, keoxifene, LY 117018, onapristone, raloxifene, tamoxifen, toremifene, and trioxifene; anti-adrenals such as aminoglutethimide, dexaminoglutethimide, mitotane, and trilostane; androgens such as calusterone, dromostanolone propionate, epitiostanol, mepitiostane, and testolactone; abarelix; anastrozole; cetrorelix; deslorelin; exemestane; fadrozole; finasteride; formestane; histrelin (RL 0903); human chorionic gonadotropin; lanreotide; LDI 200 (Milkhaus); letrozole; leuprorelin; mifepristone; nafarelin; nafoxidine; osaterone; prednisone; thyrotropin alfa; and triptorelin.

In one embodiment, the additional anti-cancer agent(s) is an immunotherapeutic agent (i.e., immunotherapy). Non-limiting examples of immunotherapeutic agents include biological response modifiers, cytokine inhibitors, tumor vaccines, monoclonal antibodies, immune checkpoint inhibitors, colony-stimulating factors, and immunomodulators.

Non-limiting examples of biological response modifiers, including cytokine inhibitors (cytokines) such as interferons and interleukins, include interferon alfa/interferon alpha such as interferon alfa-2, interferon alfa-2a, interferon alfa-2b, interferon alfa-n1, interferon alfa-n3, interferon alfacon-1, peginterferon alfa-2a, peginterferon alfa-2b, and leukocyte alpha interferon; interferon beta such as interferon beta-la, and interferon beta-1b; interferon gamma such as natural interferon gamma-1a, and interferon gamma-1b; aldesleukin; interleukin-1 beta; interleukin-2; oprelvekin; sonermin; tasonermin; and virulizin.

Non-limiting examples of tumor vaccines include APC 8015, AVICINE, bladder cancer vaccine, cancer vaccine (Biomira), gastrin 17 immunogen, Maruyama vaccine, melanoma lysate vaccine, melanoma oncolysate vaccine (New York Medical College), melanoma vaccine (New York University), melanoma vaccine (Sloan Kettering Institute), TICE® BCG (*Bacillus* Calmette-Guerin), and viral melanoma cell lysates vaccine (Royal Newcastle Hospital).

Non-limiting examples of monoclonal antibodies include abagovomab, adecatumumab, aflibercept, alemtuzumab, blinatumomab, brentuximab vedotin, CA 125 MAb (Biomira), cancer MAb (Japan Pharmaceutical Development), daclizumab, daratumumab, denosumab, edrecolomab, gemtuzumab zogamicin, HER-2 and Fc MAb (Medarex), ibritumomab tiuxetan, idiotypic 105AD7 MAb (CRC Technology), idiotypic CEA MAb (Trilex), ipilimumab, lintuzumab, LYM-1-iodine 131 MAb (Techni clone), mitumomab, moxetumomab, ofatumumab, polymorphic epithelial mucin-yttrium 90 MAb (Antisoma), ranibizumab, rituximab, and trastuzumab.

Non-limiting examples of immune checkpoint inhibitors include anti-PD-1 agents or antibodies such as cemiplimab, nivolumab, and pembrolizumab; anti-PD-L1 agents or antibodies such as atezolizumab, avelumab, and durvalumab; anti-CTLA-4 agents or antibodies such as ipilumumab; anti-LAG1 agents; and anti-OX40 agents.

Non-limiting examples of colony-stimulating factors include darbepoetin alfa, epoetin alfa, epoetin beta, filgrastim, granulocyte macrophage colony stimulating factor, lenograstim, leridistim, mirimostim, molgramostim, nartograstim, pegfilgrastim, and sargramostim.

Non-limiting examples of additional immunotherapeutic agents include BiTEs, CAR-T cells, GITR agonists, imiquimod, immunomodulatory imides (IMiDs), mismatched double stranded RNA (Ampligen), resiquimod, SRL 172, and thymalfasin.

In one embodiment, the additional anti-cancer agent(s) is a targeted therapy agent (i.e., targeted therapy). Targeted therapy agents include, for example, monoclonal antibodies and small molecule drugs. Non-limiting examples of targeted therapy agents include signal transduction inhibitors, growth factor inhibitors, tyrosine kinase inhibitors, EGFR inhibitors, histone deacetylase (HDAC) inhibitors, proteasome inhibitors, cell-cycle inhibitors, angiogenesis inhibitors, matrix-metalloproteinase (MMP) inhibitors, hepatocyte growth factor inhibitors, TOR inhibitors, KDR inhibitors, VEGF inhibitors, fibroblast growth factors (FGF) inhibitors, MEK inhibitors, ERK inhibitors, PI3K inhibitors, AKT inhibitors, MCL-1 inhibitors, BCL-2 inhibitors, SHP2 inhibitors, HER-2 inhibitors, BRAF-inhibitors, gene expression modulators, autophagy inhibitors, apoptosis inducers, antiproliferative agents, and glycolysis inhibitors.

Non-limiting examples of signal transduction inhibitors include tyrosine kinase inhibitors, multiple-kinase inhibitors, anlotinib, avapritinib, axitinib, dasatinib, dovitinib, imatinib, lenvatinib, lonidamine, nilotinib, nintedanib, pazopanib, pegvisomant, ponatinib, vandetanib, and EGFR inhibitory agents.

Non-limiting examples of EGFR inhibitory agents include small molecule antagonists of EGFR such as afatinib, brigatinib, erlotinib, gefitinib, lapatinib, and osimertinib; and antibody-based EGFR inhibitors, including any anti-EGFR antibody or antibody fragment that can partially or completely block EGFR activation by its natural ligand. Antibody-based EGFR inhibitory agents may include, for example, those described in Modjtahedi, H., et al., 1993, Br. J. Cancer 67:247-253; Teramoto, T., et al., 1996, Cancer 77:639-645; Goldstein et al, 1995, Clin. Cancer Res. 1: 1311-1318; Huang, S. M., et al., 1999, Cancer Res. 15:59(8): 1935-40; and Yang, X., et al., 1999, Cancer Res. 59: 1236-1243; monoclonal antibody Mab E7.6.3 (Yang, 1999 supra); Mab C225 (ATCC Accession No. HB-8508), or an antibody or antibody fragment having the binding specificity thereof; specific antisense nucleotide or siRNA; afatinib, cetuximab; matuzumab; necitumumab; nimotuzumab; panitumumab; and zalutumumab.

Non-limiting examples of histone deacetylase (HDAC) inhibitors include belinostat, panobinostat, romidepsin, and vorinostat.

Non-limiting examples of proteasome inhibitors include bortezomib, carfilzomib, ixazomib, marizomib (salinosporamide a), and oprozomib.

Non-limiting examples of cell-cycle inhibitors, including CDK inhibitors, include abemaciclib, alvocidib, palbociclib, and ribociclib.

In one embodiment, the additional anti-cancer agent(s) is an anti-angiogenic agent (or angiogenesis inhibitor) including, but not limited to, matrix-metalloproteinase (MMP) inhibitors; VEGF inhibitors; EGFR inhibitors; TOR inhibitors such as everolimus and temsirolimus; PDGFR kinase inhibitory agents such as crenolanib; HIF-1α inhibitors such as PX 478; HIF-2α inhibitors such as belzutifan and the HIF-2α inhibitors described in WO 2015/035223; fibroblast growth factor (FGF) or FGFR inhibitory agents such as B-FGF and RG 13577; hepatocyte growth factor inhibitors; KDR inhibitors; anti-Ang1 and anti-Ang2 agents; anti-Tie2 kinase inhibitory agents; Tek antagonists (US 2003/0162712; U.S. Pat. No. 6,413,932); anti-TWEAK agents (U.S. Pat. No. 6,727,225); ADAM distintegrin domain to antagonize the binding of integrin to its ligands (US 2002/0042368); anti-eph receptor and/or anti-ephrin antibodies or antigen binding regions (U.S. Pat. Nos. 5,981,245; 5,728,813; 5,969,110; 6,596,852; 6,232,447; and 6,057,124); and anti-PDGF-BB antagonists as well as antibodies or antigen binding regions specifically binding to PDGF-BB ligands.

Non-limiting examples of matrix-metalloproteinase (MMP) inhibitors include MMP-2 (matrix-metalloproteinase 2) inhibitors, MMP-9 (matrix-metalloproteinase 9) inhibitors, prinomastat, RO 32-3555, and RS 13-0830. Examples of useful matrix metalloproteinase inhibitors are described, for example, in WO 96/33172, WO 96/27583, EP 1004578, WO 98/07697, WO 98/03516, WO 98/34918, WO 98/34915, WO 98/33768, WO 98/30566, EP 0606046, EP 0931788, WO 90/05719, WO 99/52910, WO 99/52889, WO 99/29667, WO 1999/007675, EP 1786785, EP 1181017, US 2009/0012085, U.S. Pat. Nos. 5,863,949, 5,861,510, and EP 0780386. Preferred MMP-2 and MMP-9 inhibitors are those that have little or no activity inhibiting MMP-1. More preferred, are those that selectively inhibit MMP-2 and/or MMP-9 relative to the other matrix-metalloproteinases (i.e., MMP-1, MMP-3, MMP-4, MMP-5, MMP-6, MMP-7, MMP-8, MMP-10, MMP-11, MMP-12, and MMP-13).

Non-limiting examples of VEGF and VEGFR inhibitory agents include bevacizumab, cediranib, CEP 7055, CP 547632, KRN 633, orantinib, pazopanib, pegaptanib, pegaptanib octasodium, semaxanib, sorafenib, sunitinib, VEGF antagonist (Borean, Denmark), and VEGF-TRAP™.

The additional anti-cancer agent(s) may also be another anti-angiogenic agent including, but not limited to, 2-methoxyestradiol, AE 941, alemtuzumab, alpha-D148 Mab (Amgen, US), alphastatin, anecortave acetate, angiocidin, angiogenesis inhibitors, (SUGEN, US), angiostatin, anti-Vn Mab (Crucell, Netherlands), atiprimod, axitinib, AZD 9935, BAY RES 2690 (Bayer, Germany, BC 1 (Genoa Institute of Cancer Research, Italy), beloranib, benefin (Lane Labs, US), cabozantinib, CDP 791 (Celltech Group, UK), chondroitinase AC, cilengitide, combretastatin A4 prodrug, CP 564959 (OSI, US), CV247, CYC 381 (Harvard University, US), E 7820, EHT 0101, endostatin, enzastaurin hydrochloride, ER-68203-00 (IVAX, US), fibrinogen-E fragment, Flk-1 (ImClone Systems, US), forms of FLT 1 (VEGFR 1), FR-111142, GCS-100, GW 2286 (GlaxoSmithKline, UK), IL-8, ilomastat, IM-862, irsogladine, KM-2550 (Kyowa Hakko, Japan), lenalidomide, lenvatinib, MAb alpha5beta3 integrin, second generation (Applied Molecular Evolution, USA and MedImmune, US), MAb VEGF (Xenova, UK), marimastat, maspin (Sosei, Japan), metastatin, motuporamine C, M-PGA, ombrabulin, OXI4503, PI 88, platelet factor 4, PPI 2458, ramucirumab, rBPI 21 and BPI-derived antiangiogenic (XOMA, US), regorafenib, SC-236, SD-7784 (Pfizer, US), SDX 103 (University of California at San Diego, US), SG 292 (Telios, US), SU-0879 (Pfizer, US), TAN-1120, TBC-1635, tesevatinib, tetrathiomolybdate, thalidomide, thrombospondin 1 inhibitor, Tie-2 ligands (Regeneron, US), tissue factor pathway inhibitors (EntreMed, US), tumor necrosis factor-alpha inhibitors, tumstatin, TZ 93, urokinase plasminogen activator inhibitors, vadimezan, vandetanib, vasostatin, vatalanib, VE-cadherin-2 antagonists, xanthorrhizol, XL 784 (Exelixis, US), ziv-aflibercept, and ZD 6126.

In embodiments, the additional anti-cancer agent(s) is an additional active agent that disrupts or inhibits RAS-RAF-ERK or PI3K-AKT-TOR signaling pathways or is a PD-1 and/or PD-L1 antagonist. In embodiments, the additional anti-cancer agent(s) is a RAF inhibitor, EGFR inhibitor, MEK inhibitor, ERK inhibitor, PI3K inhibitor, AKT inhibitor, TOR inhibitor, MCL-1 inhibitor, BCL-2 inhibitor, SHP2 inhibitor, proteasome inhibitor, or immune therapy, including monoclonal antibodies, immunomodulatory imides (IMiDs), anti-PD-1, anti-PDL-1, anti-CTLA4, anti-LAG1, and anti-OX40 agents, GITR agonists, CAR-T cells, and BiTEs.

Non-limiting examples of RAF inhibitors include dabrafenib, encorafenib, regorafenib, sorafenib, and vemurafenib.

Non-limiting examples of MEK inhibitors include binimetinib, CI-1040, cobimetinib, PD318088, PD325901, PD334581, PD98059, refametinib, selumetinib, and trametinib.

Non-limiting examples of ERK inhibitors include LY3214996, LTT462, MK-8353, SCH772984, ravoxertinib, ulixertinib, and an ERKi as described in WO 2017/068412.

Non-limiting examples of PI3K inhibitors include 17-hydroxywortmannin analogs (e.g., WO 06/044453); AEZS-136; alpelisib; AS-252424; buparlisib; CAL263; copanlisib; CUDC-907; dactolisib (WO 06/122806); demethoxyviridin;

duvelisib; GNE-477; GSK1059615; IC87114; idelalisib; INK1117; LY294002; Palomid 529; paxalisib; perifosine; PI-103; PI-103 hydrochloride; pictilisib (e.g., WO 09/036,082; WO 09/055,730); PIK 90; PWT33597; SF1126; sonolisib; TGI 00-115; TGX-221; XL147; XL-765; wortmannin; and ZSTK474.

Non-limiting examples of AKT inhibitors include Akt-1-1 (inhibits Akt1) (Barnett et al. (2005) *Biochem. J.,* 385 (Pt. 2), 399-408); Akt-1-1,2 (Barnett et al. (2005) *Biochem. J.* 385 (Pt. 2), 399-408); API-59CJ-Ome (e.g., Jin et al. (2004) Br. J. Cancer 91, 1808-12); 1-H-imidazo[4,5-c]pyridinyl compounds (e.g., WO05011700); indole-3-carbinol and derivatives thereof (e.g., U.S. Pat. No. 6,656,963; Sarkar and Li (2004) *J Nutr.* 134(12 Suppl), 3493S-3498S); perifosine, Dasmahapatra et al. (2004) *Clin. Cancer Res.* 10(15), 5242-52, 2004); phosphatidylinositol ether lipid analogues (e.g., Gills and Dennis (2004) *Expert. Opin. Investig. Drugs* 13, 787-97); triciribine (Yang et al. (2004) Cancer Res. 64, 4394-9); imidazooxazone compounds including trans-3-amino-1-methyl-3-[4-(3-phenyl-5H-imidazo[1,2-c]pyrido [3,4-e][1,3]oxazin-2-yl)phenyl]-cyclobutanol hydrochloride (WO 2012/137870); afuresertib; capivasertib; MK2206; and patasertib.

Non-limiting examples of TOR inhibitors include deforolimus; ATP-competitive TORC1/TORC2 inhibitors, including PI-103, PP242, PP30, and Torin 1; TOR inhibitors in FKBP12 enhancer, rapamycins and derivatives thereof, including temsirolimus, everolimus, WO 9409010; rapalogs, e.g. as disclosed in WO 98/02441 and WO 01/14387, e.g. AP23573, AP23464, or AP23841; 40-(2-hydroxyethyl) rapamycin, 40-[3-hydroxy(hydroxymethyl)methylpropanoate]-rapamycin; 40-epi-(tetrazolyl)-rapamycin (also called ABT578); 32-deoxorapamycin; 16-pentynyloxy-32(S)-dihydrorapanycin, and other derivatives disclosed in WO 05/005434; derivatives disclosed in U.S. Pat. No. 5,258,389, WO 94/090101, WO 92/05179, U.S. Pat. Nos. 5,118,677, 5,118,678, 5,100,883, 5,151,413, 5,120,842, WO 93/111130, WO 94/02136, WO 94/02485, WO 95/14023, WO 94/02136, WO 95/16691, WO 96/41807, WO 96/41807 and U.S. Pat. No. 5,256,790; and phosphorus-containing rapamycin derivatives (e.g., WO 05/016252).

Non-limiting examples of MCL-1 inhibitors include AMG-176, MIK665, and S63845.

Non-limiting examples of SHP2 inhibitors include SHP2 inhibitors described in WO 2019/167000 and WO 2020/022323.

Additional non-limiting examples of anti-cancer agents that are suitable for use include 2-ethylhydrazide, 2,2',2"-trichlorotriethylamine, ABVD, aceglatone, acemannan, aldophosphamide glycoside, alpharadin, amifostine, aminolevulinic acid, anagrelide, ANCER, ancestim, anti-CD22 immunotoxins, antitumorigenic herbs, apaziquone, arglabin, arsenic trioxide, azathioprine, BAM 002 (Novelos), bcl-2 (Genta), bestrabucil, biricodar, bisantrene, bromocriptine, brostallicin, bryostatin, buthionine sulfoximine, calyculin, cell-cycle nonspecific antineoplastic agents, celmoleukin, clodronate, clotrimazole, cytarabine ocfosfate, DA 3030 (Dong-A), defofamine, denileukin diftitox, dexrazoxane, diaziquone, dichloroacetic acid, dilazep, discodermolide, docosanol, doxercalciferol, edelfosine, eflornithine, EL532 (Elan), elfomithine, elsamitrucin, eniluracil, etanidazole, exisulind, ferruginol, folic acid replenisher such as frolinic acid, gacytosine, gallium nitrate, gimeracil/oteracil/tegafur combination (S-1), glycopine, histamine dihydrochloride, HIT diclofenac, HLA-B7 gene therapy (Vical), human fetal alpha fetoprotein, ibandronate, ibandronic acid, ICE chemotherapy regimen, imexon, iobenguane, IT-101 (CRLX101), laniquidar, LC 9018 (Yakult), leflunomide, lentinan, levamisole+fluorouracil, lovastatin, lucanthone, masoprocol, melarsoprol, metoclopramide, miltefosine, miproxifene, mitoguazone, mitozolomide, mopidamol, motexafin gadolinium, MX6 (Galderma), naloxone+pentazocine, nitracrine, nolatrexed, NSC 631570 octreotide (Ukrain), olaparib, P-30 protein, PAC-1, palifermin, pamidronate, pamidronic acid, pentosan polysulfate sodium, phenamet, picibanil, pixantrone, platinum, podophyllinic acid, porfimer sodium, PSK (Polysaccharide-K), rabbit antithymocyte polyclonal antibody, rasburiembodiment, retinoic acid, rhenium Re 186 etidronate, romurtide, samarium (153 Sm) lexidronam, sizofiran, sodium phenylacetate, sparfosic acid, spirogermanium, strontium-89 chloride, suramin, swainsonine, talaporfin, tariquidar, tazarotene, tegafur-uracil, temoporfin, tenuazonic acid, tetrachlorodecaoxide, thrombopoietin, tin ethyl etiopurpurin, tirapazamine, TLC ELL-12, tositumomab-iodine 131, trifluridine and tipiracil combination, troponin I (Harvard University, US), urethan, valspodar, verteporfin, zoledronic acid, and zosuquidar.

The present disclosure further provides a method for using the compounds of Formula (I) or pharmaceutical compositions provided herein, in combination with radiation therapy to treat cancer. Techniques for administering radiation therapy are known in the art, and these techniques can be used in the combination therapy described herein. The administration of the compound of Formula (I) in this combination therapy can be determined as described herein.

Radiation therapy can be administered through one of several methods, or a combination of methods, including, without limitation, external-beam therapy, internal radiation therapy, implant radiation, stereotactic radiosurgery, systemic radiation therapy, radiotherapy and permanent or temporary interstitial brachy therapy. The term "brachytherapy," as used herein, refers to radiation therapy delivered by a spatially confined radioactive material inserted into the body at or near a tumor or other proliferative tissue disease site. The term is intended, without limitation, to include exposure to radioactive isotopes (e.g., At-211, I-131, I-125, Y-90, Re-186, Re-188, Sm-153, Bi-212, P-32, and radioactive isotopes of Lu). Suitable radiation sources for use as a cell conditioner of the present disclosure include both solids and liquids. By way of non-limiting example, the radiation source can be a radionuclide, such as I-125, I-131, Yb-169, Ir-192 as a solid source, I-125 as a solid source, or other radionuclides that emit photons, beta particles, gamma radiation, or other therapeutic rays. The radioactive material can also be a fluid made from any solution of radionuclide(s), e.g., a solution of I-125 or I-131, or a radioactive fluid can be produced using a slurry of a suitable fluid containing small particles of solid radionuclides, such as Au-198, Y-90. Moreover, the radionuclide(s) can be embodied in a gel or radioactive microspheres.

The present application also provides methods for combination therapies in which the additional active agent is known to modulate other pathways, or other components of the same pathway, or even overlapping sets of target enzymes which are used in combination with a compound of Formula (I), or a pharmaceutically acceptable salt thereof. In one embodiment, such therapy includes, but is not limited to, the combination of one or more compounds of Formula (I) with chemotherapeutic agents, immunotherapeutic agents, hormonal therapy agents, therapeutic antibodies, targeted therapy agents, and radiation treatment, to provide a synergistic or additive therapeutic effect.

The present disclosure also provides for the use the compound of Formula (I) or the pharmaceutically acceptable salt thereof in therapy. The present disclosure also provides for the use the compound of Formula (I) or the pharmaceutically acceptable salt thereof for treating cancer. The present disclosure also provides for the use of the compound of Formula (I) or the pharmaceutically acceptable salt thereof for the preparation of a medicament for the treatment of the cancer. The present disclosure also provides a compound of Formula (I), or the pharmaceutically acceptable salt thereof, and an additional anti-cancer agent, for use in the treatment of cancer, or use of the compound of Formula (I), or the pharmaceutically acceptable salt thereof, and the additional anti-cancer agent for use in the treatment of cancer. The present disclosure also provides a pharmaceutical composition comprising the compound of Formula (I), or the pharmaceutically acceptable salt thereof, and an additional anti-cancer agent, for use in the treatment of cancer, or use of the pharmaceutical composition comprising the compound of Formula (I), or the pharmaceutically acceptable salt thereof, and the additional anti-cancer agent, for use in the treatment of cancer. The present disclosure also provides a compound of Formula (I), or the pharmaceutically acceptable salt thereof, and an additional anti-cancer agent, for the preparation of a medicament for the treatment of cancer, or use of the compound of Formula (I), or the pharmaceutically acceptable salt thereof, and the additional anti-cancer agent, for the preparation of a medicament for the treatment of cancer.

EXAMPLES

Specific embodiments of the invention will now be demonstrated by reference to the following examples. It should be understood that these examples are disclosed solely by way of illustrating the invention and should not be taken in any way to limit the scope of the present invention.

The reagents used in the Examples are commercially available products unless indicated otherwise. Prepacked columns manufactured by Shoko Scientific Co., Ltd. (Yokohama, Japan) or Biotage (Uppsala, Sweden) were used in silica gel column chromatography and basic silica gel column chromatography. A Bruker Avance NEO spectrometer at 400 MHz or a Bruker Avance III Spectrometer at 500 MHz was used for NMR spectra. For a deuterated solvent containing tetramethylsilane, tetramethylsilane was used as the internal reference. In other cases, measurement was performed using an NMR solvent as the internal reference. All δ values are indicated in ppm. Microwave reaction was performed using an Biotage® Initiator+. Reverse phase preparative HPLC column chromatography was performed at the following conditions:

Column: XSelect CSH C18 OBD manufactured by Waters. 130A. 5 μm. 19×100 mm
UV detection: 254 nm
Column flow rate: 18 mL/min
Mobile phase: water/acetonitrile (0.1% formic acid)
Injection volume: 0.5 mL
Basic gradient method: water/acetonitrile 15%-40% (8 minutes)

The following abbreviations are used herein:

s: singlet
d: doublet
t: triplet
q: quartet
sep: septet
dd: double doublet
dt: double triplet
td: triple doublet
tt: triple triplet
ddd: double double doublet
ddt: double double triplet
dtd: double triple doublet
tdd: triple double doublet
m: multiplet
br: broad
brs: broad singlet
tert: tertiary
DMSO-d 6: deuterated dimethyl sulfoxide
THF: tetrahydrofuran
DMF: N,N-dimethylformamide
NMP: 1-methyl-2-pyrrolidinone
DMSO: dimethyl sulfoxide
DIAD: diisopropyl azodicarboxylate
DIPEA: N,N-diisopropylethylamine
HATU: 1-[bis(dimethylamino)methylene]-1H-1,2,3-triazole[4,5-b]pyridinium-3-oxidehexafluorophosphate
Boc: tert-butoxycarbonyl group
Cbz: carbobenzoxy group

Preparation 1

5-(tert-butyl)-6-chloro-1H-indazole-3-amine

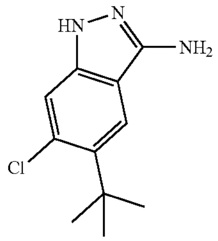

Step 1: After nitric acid (1.40) (23 mL) was slowly added to concentrated sulfuric acid (32 mL) at ice cooling temperature, 1-bromo-4-tert-butylbenzene (60 g) was added thereto at an internal temperature of 25° C. or below. The mixture was stirred at room temperature for 3 hours, and then poured onto ice, followed by extraction with diethyl ether. The organic layer was washed with a sodium hydrogen carbonate aqueous solution and a saturated sodium chloride solution and dried over sodium sulfate. The solution was evaporated under reduced pressure, thereby obtaining crude 1-bromo-4-(tert-butyl)-2-nitrobenzene (72.1 g).

Step 2: A suspension of crude 1-bromo-4-(tert-butyl)-2-nitrobenzene (72.1 g) obtained in Step 1, iron powder (50 g), and ammonium chloride (50 g) in ethanol (400 mL) and water (100 mL) was stirred at 70° C. for 90 minutes. After ethanol was evaporated under reduced pressure, water and ethyl acetate were added thereto, followed by filtrating off the insoluble matter. The organic layer was separated and washed with a saturated sodium chloride solution, followed by drying over sodium sulfate. The solvent was evaporated under reduced pressure, and then ethyl acetate (200 mL) and acetic anhydride (30 mL) were added thereto. The solvent was evaporated under reduced pressure, and hexane (300 mL) was added, followed by collecting the precipitated solid, thereby obtaining N-(2-bromo-5-(tert-butyl)phenyl)acetamide (40.6 g).

Step 3: N-chlorosuccinimide (4.00 g) was added to a solution of N-(2-bromo-5-(tert-butyl)phenyl)acetamide (5.40 g) obtained in Step 2, (D)-(+)-10-camphorsulfonic acid (2.40 g), and 1,3-dimethyl imidazolium chloride (264 mg) in 1,4-dioxane (54 mL), and the mixture was stirred at room temperature overnight. A sodium hydrogen carbonate aqueous solution and sodium thiosulfate were added to the reaction mixture, and the mixture was extracted with ethyl acetate, followed by washing the organic layer with a saturated sodium chloride solution. After the washed organic layer was dried over sodium sulfate, the solvent was evaporated under reduced pressure, followed by collecting the solid, thereby obtaining N-(2-bromo-5-(tert-butyl)-4-chlorophenyl)acetamide (5.40 g).

Step 4: A 5N sodium hydroxide aqueous solution (100 mL) was added to a solution of N-(2-bromo-5-(tert-butyl)-4-chlorophenyl)acetamide (17.1 g) obtained in Step 3 in ethanol (100 mL), and the mixture was stirred at 90° C. for 5 hours. After the ethanol in the reaction mixture was evaporated under reduced pressure, the mixture was extracted with 2-methyltetrahydrofuran, followed by washing the organic layer with a saturated sodium chloride solution. The washed organic layer was dried over sodium sulfate, and the solvent was evaporated under reduced pressure, thereby obtaining 2-bromo-5-(tert-butyl)-4-chloroaniline (14.8 g).

Step 5: 2-Bromo-5-(tert-butyl)-4-chloroaniline (81.1 g) obtained in Step 4 was cooled to an internal temperature of 0° C., and 3N hydrochloric acid (566 mL) was added thereto. Sodium nitrite (24.3 g) was added little by little, and the mixture was stirred at an internal temperature of 0° C. for 1 hour to prepare a diazonium salt suspension. The diazonium salt suspension was added to a suspension of copper(I) cyanide (27.7 g), sodium cyanide (30.3 g), and sodium hydrogen carbonate (145 g) in water (570 mL) at ice cooling temperature, and the mixture was stirred at 0° C. for 1 hour. After stirring, the mixture was heated to room temperature, and ethyl acetate was added thereto, followed by celite filtration. The filtrate was partitioned, and the organic layer was washed with a 20% sodium chloride solution, followed by drying over magnesium sulfate. The solvent was evaporated under reduced pressure, and the obtained residue was purified by column chromatography (hexane:ethyl acetate), thereby obtaining 2-bromo-5-(tert-butyl)-4-chlorobenzonitrile (61.1 g).

Step 6: Palladium acetate (2.5 g) was added to a suspension of 2-bromo-5-(tert-butyl)-4-chlorobenzonitrile (61.1 g) obtained in Step 5, benzophenone hydrazone (51.9 g), rac-2,2'-bis(diphenylphosphino)-1,1'-binaphthyl (7.7 g), and cesium carbonate (102 g) in toluene (470 mL). The mixture was heated at an internal temperature of 101° C. in a nitrogen atmosphere for 1.5 hours. The mixture was then cooled to room temperature, and ethyl acetate and water were added thereto, followed by celite filtration and separating the organic layer. The organic layer was dried over sodium sulfate, and the solvent was evaporated under reduced pressure. The residue was purified by column chromatography (hexane:dichloromethane), thereby obtaining 5-(tert-butyl)-4-chloro-2-(2-(diphenylmethylene)hydrazinyl) benzonitrile (52.8 g).

Step 7: p-toluenesulfonic acid monohydrate (51.8 g) was added to a solution of 5-(tert-butyl)-4-chloro-2-(2-(diphenylmethylene)hydrazinyl) benzonitrile (52.8 g) obtained in Step 6 in methanol (375 mL), and the mixture was heated at an internal temperature of 63° C. for 1.5 hours. The reaction mixture was cooled to room temperature and washed with hexane. The hexane layer was then extracted with methanol, and the solvent was evaporated under reduced pressure. The residue was dissolved in ethyl acetate and washed with a mixture solution of a saturated sodium hydrogen carbonate aqueous solution (375 mL) and a 5N sodium hydroxide aqueous solution. The aqueous layer was extracted with ethyl acetate, and the organic layer was washed with a saturated sodium hydrogen carbonate aqueous solution. The washed organic layer was dried over magnesium sulfate, and the solvent was evaporated under reduced pressure. The obtained residue was purified by column chromatography (hexane:ethyl acetate), thereby obtaining 5-(tert-butyl)-6-chloro-1H-indazole-3-amine (29.0 g).

Preparation 2 methyl 4-chloro-1H-imidazole-5-carboxylate

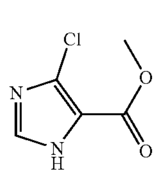

Step 1: Methanesulfonic acid (90 mL) was added to a solution of 4-amino-1H-imidazole-5-carboxamide (52 g) in methanol (300 mL), followed by stirring at 110° C. for 3 days. The solution was concentrated under reduced pressure, and a 5N sodium hydroxide aqueous solution was added thereto. The mixture was extracted with ethyl acetate, and the organic layer was washed with a saturated sodium chloride solution. The washed organic layer was dried over sodium sulfate, and the solvent was evaporated under reduced pressure, thereby obtaining crude methyl 4-amino-1H-imidazole-5-carboxylate (33 g).

Step 2: Concentrated hydrochloric acid (20 mL) was added to methyl 4-amino-1H-imidazole-5-carboxylate (4.5 g) obtained in Step 1, and a sodium nitrite (3.3 g) aqueous solution (1.5 mL) was added dropwise thereto at ice cooling temperature, followed by stirring at the same temperature for 15 minutes. The reaction solution was spread on a glass plate and irradiated with UV light at 302 nm from a distance of 3 cm overnight. A 5N sodium hydroxide aqueous solution was added at ice cooling temperature, and the precipitated solid was collected, followed by drying by heating overnight, thereby obtaining methyl 4-chloro-1H-imidazole-5-carboxylate (2.6 g).

Preparation 3 methyl 4-chloro-1-methyl-1H-imidazole-5-carboxylate

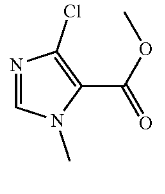

Methanol (150 μL), triphenylphosphine (1.2 g), and DIAD (880 μL) were added to a solution of methyl 4-chloro-1H-imidazole-5-carboxylate (600 mg) obtained in Preparation 2 in THF (7 mL), followed by stirring at room temperature for 30 minutes. The solvent was evaporated under reduced pressure, and the obtained residue was purified by column chromatography (hexane:ethyl acetate), thereby obtaining methyl 4-chloro-1-methyl-1H-imidazole-5-carboxylate (360 mg).

Preparation 4

2-(((5-(tert-butyl)-6-chloro-1H-indazol-3-yl)amino) methyl)-4-chloro-1-methyl-1H-imidazole-5-carboxylic Acid

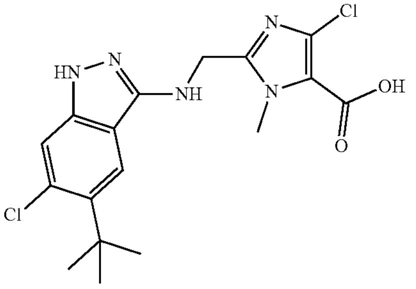 [SMILES: Cn1c(CNc2n[nH]c3cc(Cl)c(C(C)(C)C)cc23)nc(Cl)c1C(=O)O]

Step 1: A solution of methyl 4-chloro-1-methyl-1H-imidazole-5-carboxylate (1 g) obtained in Preparation 3 in carbon tetrachloride (20 mL) was mixed with N-bromosuccinimide (1.3 g) and azobisisobutyronitrile (120 mg) in a nitrogen atmosphere, followed by stirring at 95° C. overnight. After the reaction mixture was filtered, the solution was evaporated under reduced pressure, followed by subjecting the crude product to column purification (hexane: ethyl acetate), thereby obtaining methyl 2-bromo-4-chloro-1-methyl-1H-imidazole-5-carboxylate (930 mg).

Step 2: A solution of 2M isopropyl magnesium chloride in tetrahydrofuran (3.5 mL) was added dropwise to a solution of methyl 2-bromo-4-chloro-1-methyl-1H-imidazole-5-carboxylate (730 mg) obtained in Step 1 in tetrahydrofuran (26 mL) at −78° C., followed by stirring at the same temperature for 1 hour. After N,N-dimethylformamide was added dropwise to the reaction mixture, the mixture was heated to −20° C., followed by stirring for another 1 hour. 1N hydrochloric acid was added to the reaction mixture, and the mixture was extracted with ethyl acetate. The organic layer was washed with a saturated sodium chloride solution and dried over sodium sulfate. The solution was evaporated under reduced pressure, and the crude product was subjected to column purification (hexane:ethyl acetate), thereby obtaining methyl 4-chloro-2-formyl-1-methyl-1H-imidazole-5-carboxylate (460 mg).

Step 3: A solution of methyl 4-chloro-2-formyl-1-methyl-1H-imidazole-5-carboxylate (290 mg) obtained in Step 2 in dichloromethane (6 mL) was mixed with 5-(tert-butyl)-6-chloro-1H-indazole-3-amine (290 mg) obtained in Preparation 1, trifluoroacetic acid (220 μL), and sodium triacetoxyborohydride (550 mg), followed by stirring at room temperature for 15 minutes. A sodium hydrogen carbonate aqueous solution was added to the reaction mixture, and the mixture was extracted with ethyl acetate. The organic layer was washed with a saturated sodium chloride solution and dried over sodium sulfate. The solvent was evaporated under reduced pressure, and the obtained residue was purified by column chromatography (hexane:ethyl acetate), thereby obtaining methyl 2-(((5-(tert-butyl)-6-chloro-1H-indazol-3-yl)amino)methyl)-4-chloro-1-methyl-1H-imidazole-5-carboxylate (430 mg).

Step 4: A 5N sodium hydroxide aqueous solution (1 mL) was added to a solution of methyl 2-(((5-(tert-butyl)-6-chloro-1H-indazol-3-yl)amino)methyl)-4-chloro-1-methyl-1H-imidazole-5-carboxylate (85 mg) obtained in Step 3 in ethanol (1 mL), followed by stirring at room temperature for 1 hour. The reaction mixture was evaporated under reduced pressure, and 5N hydrochloric acid was added thereto, followed by extraction with ethyl acetate. The organic layer was washed with a saturated sodium chloride solution and dried over sodium sulfate. The solution was evaporated under reduced pressure, thereby obtaining 2-(((5-(tert-butyl)-6-chloro-1H-indazol-3-yl)amino)methyl)-4-chloro-1-methyl-1H-imidazole-5-carboxylic acid (70 mg).

Preparation 5 methyl (R)-1-(1-(tert-butoxycarbonyl)pyrrolidin-3-yl)-4-chloro-1H-imidazole-5-carboxylate

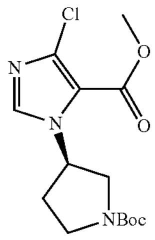 [SMILES: COC(=O)c1c(Cl)ncn1[C@@H]1CCN(C(=O)OC(C)(C)C)C1]

The procedure of Preparation 3 was performed except that (S)-1-(tert-butoxycarbonyl)-3-pyrrolidinol was used instead of methanol used in Preparation 3, thereby obtaining methyl (R)-1-(1-(tert-butoxycarbonyl)pyrrolidin-3-yl)-4-chloro-1H-imidazole-5-carboxylate (10.61 g, >99% ee).

Preparation 6 methyl (R)-1-(1-(tert-butoxycarbonyl)pyrrolidin-3-yl)-4-chloro-2-formyl-1H-imidazole-5-carboxylate

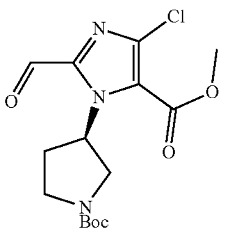 [SMILES: COC(=O)c1c(Cl)nc(C=O)n1[C@@H]1CCN(C(=O)OC(C)(C)C)C1]

THF (70 mL) and DMF (3.18 mL) were added to methyl (R)-1-(1-(tert-butoxycarbonyl)pyrrolidin-3-yl)-4-chloro-1H-imidazole-5-carboxylate (3.29 g) obtained in Preparation 5, followed by cooling in an ice-methanol bath. 2,2,6,6-Tetramethylpiperidinyl magnesium chloride and a lithium chloride complex (a 1M THF/toluene solution, 40 mL) were added thereto, and the mixture was stirred for 30 minutes. Water and a 10% phosphoric acid aqueous solution were added to the reaction mixture, and the mixture was extracted with ethyl acetate. The organic layer was washed with a saturated sodium chloride solution and dried over sodium sulfate, followed by evaporating the solvent under reduced pressure. The obtained residue was purified by column chromatography (hexane:ethyl acetate) and concentrated, followed by adding hexane to collect the precipitated solid, thereby obtaining methyl (R)-1-(1-(tert-butoxycarbonyl)pyrrolidin-3-yl)-4-chloro-2-formyl-1H-imidazole-5-carboxylate (2.29 g).

Preparation 7 methyl (R)-1-(1-(tert-butoxycarbonyl)pyrrolidin-3-yl)-2-(((5-(tert-butyl)-6-chloro-1H-indazol-3-yl)amino)methyl)-4-chloro-1H-imidazole-5-carboxylate

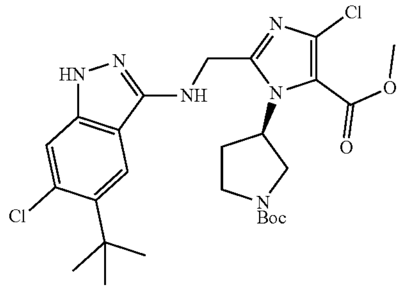 [SMILES: COC(=O)c1c(Cl)nc(CNc2n[nH]c3cc(Cl)c(C(C)(C)C)cc23)n1[C@@H]1CCN(C(=O)OC(C)(C)C)C1]

Trifluoroacetic acid (1.00 mL) was added to a solution of methyl (R)-1-(1-(tert-butoxycarbonyl)pyrrolidin-3-yl)-4-chloro-2-formyl-1H-imidazole-5-carboxylate (2.16 g) obtained in Preparation 6 and 5-(tert-butyl)-6-chloro-1H-indazole-3-amine (1.34 g) obtained in Preparation 1 in THE (30 mL), followed by stirring at room temperature for 30 minutes. Sodium triacetoxyborohydride (600 mg) was added every 60 minutes 5 times. Thereafter, the mixture was stirred at room temperature for 80 minutes. Ethyl acetate and a saturated sodium hydrogen carbonate aqueous solution were added to the reaction mixture, and the organic layer was separated. The separated organic layer was washed with a saturated sodium chloride solution and then dried over sodium sulfate. The solvent was evaporated under reduced pressure, and the obtained residue was purified by column chromatography (chloroform:ethanol), followed by concentrating the resulting product. The obtained solid was collected, thereby obtaining methyl (R)-1-(1-(tert-butoxycarbonyl)pyrrolidin-3-yl)-2-(((5-(tert-butyl)-6-chloro-1H-indazol-3-yl)amino)methyl)-4-chloro-1H-imidazole-5-carboxylate (2.81 g).

Preparation 8

(R)-2-(((5-(tert-butyl)-6-chloro-1H-indazol-3-yl)amino)methyl)-4-chloro-1-(1-isopropylpyrrolidin-3-yl)-1H-imidazole-5-carboxylic acid

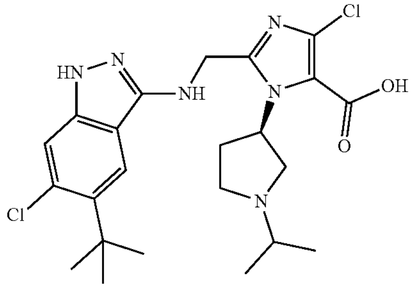 [SMILES: CC(C)N1CC[C@@H](n2c(CNc3n[nH]c4cc(Cl)c(C(C)(C)C)cc34)nc(Cl)c2C(=O)O)C1]

Step 1: Trifluoroacetic acid (1.0 mL) was added to methyl (R)-1-(1-(tert-butoxycarbonyl)pyrrolidin-3-yl)-2-(((5-(tert-butyl)-6-chloro-1H-indazol-3-yl)amino)methyl)-4-chloro-1H-imidazole-5-carboxylate (300 mg) obtained in Preparation 7, and the mixture was stirred at room temperature for 15 minutes, followed by concentrating the reaction mixture. Dichloromethane (5.0 mL), ethanol (0.5 mL), acetone (250 μL), and potassium acetate (150 mg) were added to the obtained residue. Subsequently, sodium triacetoxyborohydride (350 mg) was added thereto, followed by stirring at room temperature for 2 hours. Sodium triacetoxyborohydride (100 mg) was further added to the reaction mixture, followed by stirring at room temperature for 1 hour. A saturated sodium hydrogen carbonate aqueous solution and ethyl acetate were added to the reaction mixture. The organic layer was separated and washed with a saturated sodium chloride solution, followed by drying over sodium sulfate. The solvent was evaporated under reduced pressure. The obtained residue was purified by column chromatography (basic silica gel:hexane:ethyl acetate), thereby obtaining methyl (R)-2-(((5-(tert-butyl)-6-chloro-1H-indazol-3-yl)amino)methyl)-4-chloro-1-(1-isopropylpyrrolidin-3-yl)-1H-imidazole-5-carboxylate (170 mg).

Step 2: The procedure of Step 4 of Preparation 4 was performed except that methyl (R)-2-(((5-(tert-butyl)-6-chloro-1H-indazol-3-yl)amino)methyl)-4-chloro-1-(1-isopropylpyrrolidin-3-yl)-1H-imidazole-5-carboxylate (170 mg) obtained in step 1 was used instead of methyl 2-(((5-(tert-butyl)-6-chloro-1H-indazol-3-yl)amino)methyl)-4-chloro-1-methyl-1H-imidazole-5-carboxylate, thereby obtaining (R)-2-(((5-(tert-butyl)-6-chloro-1H-indazol-3-yl)amino)methyl)-4-chloro-1-(1-isopropylpyrrolidin-3-yl)-1H-imidazole-5-carboxylic acid (36 mg).

Preparation 9

2-amino-4-(tert-butyl)-5-chlorophenol

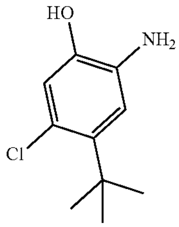

Step 1: To 2-amino-4-(tert-butyl)phenol (10 g), acetic anhydride (20 mL) was added, and the mixture was stirred for 10 minutes. Sodium acetate (8 g) was added to the reaction solution, and the mixture was stirred at 60° C. for 6 hours. The reaction solution was concentrated under reduced pressure, then water and ethyl acetate were added to the residue, and the organic layer was washed with saturated saline and dried over sodium sulfate. The solvent was distilled off under reduced pressure, and the obtained solids were collected to obtain 2-acetamido-4-(tert-butyl)phenyl acetate (13.94 g).

Step 2: To a solution of 2-acetamido-4-(tert-butyl)phenyl acetate (13.77 g) obtained in the Step 1 in acetic acid (140 mL), N-Chlorosuccinimide (7.77 g) was added, and the mixture was stirred overnight at 60° C. The reaction solution was concentrated under reduced pressure, then water and ethyl acetate were added to the residue, and the organic layer was washed with a saturated aqueous solution of sodium bicarbonate and saturated saline and dried over sodium sulfate. The solvent was distilled off under reduced pressure, and the obtained solids were collected to obtain 2-acetamido-4-(tert-butyl)-5-chlorophenyl acetate (12.67 g).

Step 3: To 2-acetamido-4-(tert-butyl)-5-chlorophenyl acetate (2.19 g) obtained in Step 2 in ethanol (7 mL), a 4 M aqueous sodium hydroxide solution (7.72 mL) was added, and the mixture was reacted at 100° C. for 2 hours in a microwave reaction apparatus. The reaction solution was poured into a saturated aqueous solution of ammonium chloride (10 mL), and precipitates were collected by filtration to obtain 2-amino-4-(tert-butyl)-5-chlorophenol (1.43 g).

Preparation 10

2-(((5-(tert-butyl)-4-chloro-2-hydroxyphenyl)amino)methyl)-4-chloro-1-methyl-1H-imidazole-5-carboxylic acid

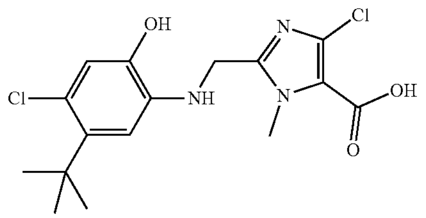 [SMILES: Cn1c(CNc2cc(C(C)(C)C)c(Cl)cc2O)nc(Cl)c1C(=O)O]

The procedure of Preparation 4 was performed except that 2-amino-4-(tert-butyl)-5-chlorophenol obtained in Preparation 9 was used instead of 5-(tert-butyl)-6-chloro-1H-indazole-3-amine obtained in Preparation 1, thereby obtaining 2-(((5-(tert-butyl)-4-chloro-2-hydroxyphenyl)amino)methyl)-4-chloro-1-methyl-1H-imidazole-5-carboxylic acid.

Preparation 11 methyl (R)-1-(1-(tert-butoxycarbonyl)pyrrolidin-3-yl)-2-(((5-(tert-butyl)-4-chloro-2-hydroxyphenyl)amino)methyl)-4-chloro-1H-imidazole-5-carboxylate

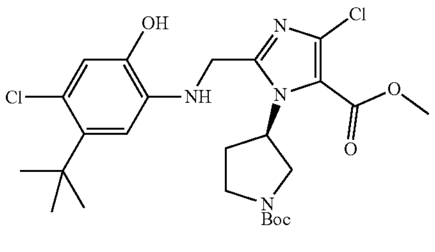 [SMILES: COC(=O)c1c(Cl)nc(CNc2cc(C(C)(C)C)c(Cl)cc2O)n1[C@@H]1CCN(C(=O)OC(C)(C)C)C1]

The procedure of Preparation 7 was performed except that 2-amino-4-(tert-butyl)-5-chlorophenol obtained in Preparation 9 was used instead of 5-(tert-butyl)-6-chloro-1H-indazole-3-amine obtained in Preparation 1, thereby obtaining methyl (R)-1-(1-(tert-butoxycarbonyl)pyrrolidin-3-yl)-2-(((5-(tert-butyl)-4-chloro-2-hydroxyphenyl)amino)methyl)-4-chloro-1H-imidazole-5-carboxylate.

Preparation 12 methyl (R)-1-(1-(tert-butoxycarbonyl)pyrrolidin-3-yl)-2-(((5-(tert-butyl)-4-chloro-2-hydroxyphenyl)amino)methyl)-4-chloro-1H-imidazole-5-carboxylate

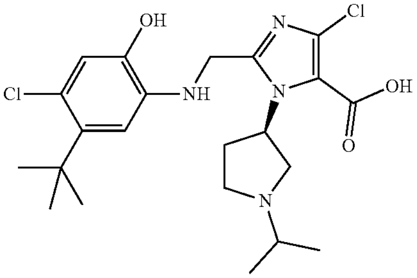 [SMILES: CC(C)N1CC[C@@H](n2c(CNc3cc(C(C)(C)C)c(Cl)cc3O)nc(Cl)c2C(=O)O)C1]

The procedure of Preparation 8 was performed except that methyl (R)-1-(1-(tert-butoxycarbonyl)pyrrolidin-3-yl)-2-(((5-(tert-butyl)-4-chloro-2-hydroxyphenyl)amino)methyl)-4-chloro-1H-imidazole-5-carboxylate obtained in Preparation 11 was used instead of methyl (R)-1-(1-(tert-butoxycarbonyl)pyrrolidin-3-yl)-2-(((5-(tert-butyl)-6-chloro-1H-indazol-3-yl)amino)methyl)-4-chloro-1H-imidazole-5-carboxylate obtained in Preparation 7, thereby obtaining methyl (R)-1-(1-(tert-butoxycarbonyl)pyrrolidin-3-yl)-2-(((5-(tert-butyl)-4-chloro-2-hydroxyphenyl)amino)methyl)-4-chloro-1H-imidazole-5-carboxylate.

Preparation 13 tert-butyl (3R,4R)-3-ethyl-4-(methylamino)pyrrolidine-1-carboxylate

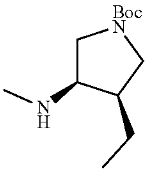 [SMILES: CC[C@@H]1CN(C(=O)OC(C)(C)C)C[C@@H]1NC]

Step 1: To a solution of tert-butyl(3R,4R)-3-amino-4-ethylpyrrolidine-1-carboxylate (0.20 g) and trimethylamine (0.42 mL) in dichloromethane (6.0 mL), benzyl chloroformate (0.22 mL) was added, followed by stirring at room temperature for 3 hours. Chloroform and a saturated sodium hydrogen carbonate aqueous solution were added to the reaction mixture, and the organic layer was separated. The separated organic layer was dried over sodium sulfate. The solvent was evaporated under reduced pressure, thereby obtaining the crude tert-butyl (3R,4R)-3-(((benzyloxy)carbonyl)amino)-4-ethylpyrrolidine-1-carboxylate, and it was used in the next step without further purification.

Step 2: To a solution of the crude tert-butyl (3R,4R)-3-(((benzyloxy)carbonyl)amino)-4-ethylpyrrolidine-1-carboxylate obtained in Step 1 in DMF (10 mL), sodium hydride (135 mg 60% oil suspension) was added. After the mixture was stirred at room temperature for 30 minutes, iodomethane was added to the solution, followed by stirring at room temperature for 30 minutes. Ethyl acetate and a saturated sodium hydrogen carbonate aqueous solution were added to the reaction mixture, and the organic layer was separated. The separated organic layer was dried over sodium sulfate. The solvent was evaporated under reduced pressure, and the obtained residue was purified by column chromatography (silica gel:hexane:ethyl acetate), thereby obtaining tert-butyl (3R,4R)-3-(((benzyloxy)carbonyl)(methyl)amino)-4-ethylpyrrolidine-1-carboxylate.

Step 3: 5% Palladium on carbon was added to the mixture of (((benzyloxy)carbonyl)(methyl)amino)-4-ethylpyrrolidine-1-carboxylate obtained in Step 2 in methanol (10 mL). The mixture was stirred at room temperature for 2 hours under hydrogen atmosphere. 5% Palldium on carbon was removed by filtration, and the filtrate was evaporated under reduced pressure, thereby obtaining tert-butyl (3R,4R)-3-ethyl-4-(methylamino)pyrrolidine-1-carboxylate (70 mg).

Preparation 14 benzyl (S)-7-(methylamino)-5-azaspiro[2.4]heptane-5-carboxylate

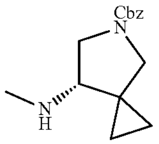 [SMILES: CN[C@@H]1CN(C(=O)OCc2ccccc2)CC12CC2]

Step 1: To a solution of tert-butyl (S)-(5-azaspiro[2.4]heptan-7-yl)carbamate (0.20 g) and trimethylamine (0.42 mL) in dichloromethane (6.0 mL), benzyl chloroformate (0.22 mL) was added, followed by stirring at room temperature for 3 hours. Chloroform and a saturated sodium hydrogen carbonate aqueous solution were added to the reaction mixture, and the organic layer was separated. The separated organic layer was dried over sodium sulfate. The solvent was evaporated under reduced pressure, thereby obtaining the crude benzyl (S)-7-((tert-butoxycarbonyl)amino)-5-azaspiro[2.4]heptane-5-carboxylate, and it was used in the next step without further purification.

Step 2: To a solution of crude benzyl (S)-7-((tert-butoxycarbonyl)amino)-5-azaspiro[2.4]heptane-5-carboxylate obtained in Step 1 in DMF (10 mL), sodium hydride (135 mg 60% oil suspension) was added. After the mixture was stirred at room temperature for 30 minutes, iodomethane was added to the solution, followed by stirring at room temperature for 30 minutes. Ethyl acetate and a saturated sodium hydrogen carbonate aqueous solution were added to the reaction mixture, and the organic layer was separated. The separated organic layer was dried over sodium sulfate. The solvent was evaporated under reduced pressure, and the obtained residue was purified by column chromatography (silica gel:hexane:ethyl acetate), thereby obtaining benzyl (S)-7-((tert-butoxycarbonyl)(methyl)amino)-5-azaspiro[2.4]heptane-5-carboxylate.

Step 3: The mixture of benzyl (S)-7-((tert-butoxycarbonyl)(methyl)amino)-5-azaspiro[2.4]heptane-5-carboxylate obtained by Step 2 with 4M hydrochloric acid solution in 1,4-dioxane (5 mL) was stirred at room temperature for 1 hour. The solvent was evaporated under reduced pressure, thereby obtaining benzyl (S)-7-(methylamino)-5-azaspiro[2.4]heptane-5-carboxylate (120 mg).

Preparation 15 tert-butyl trans-2-methyl-3-(methylamino)azetidine-1-carboxylate

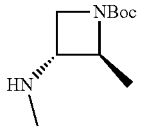

The procedure of Preparation 13 was performed except that tert-butyl trans-3-amino-2-methylazetidine-1-carboxylate was used instead of tert-butyl(3R,4R)-3-amino-4-ethylpyrrolidine-1-carboxylate, thereby obtaining tert-butyl trans-2-methyl-3-(methylamino)azetidine-1-carboxylate.

Preparation 16 tert-butyl N-methyl-N-[(1S,2S)-2-(methylamino)cyclopropyl]carbamate

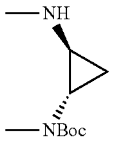

The procedure of Preparation 13 was performed except that tert-butyl ((1S,2S)-2-aminocyclopropyl)carbamate was used instead of tert-butyl(3R,4R)-3-amino-4-ethylpyrrolidine-1-carboxylate, thereby obtaining tert-butyl N-methyl-N-[(1S,2S)-2-(methylamino)cyclopropyl]carbamate.

Preparation 17 tert-butyl trans-3-methyl-4-(methylamino)pyrrolidine-1-carboxylate

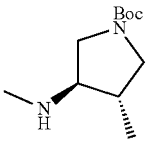

The procedure of Preparation 13 was performed except that tert-butyl trans-3-methyl-4-aminopyrrolidine-1-carboxylate was used instead of tert-butyl(3R,4R)-3-amino-4-ethylpyrrolidine-1-carboxylate, thereby obtaining tert-butyl trans-3-methyl-4-(methylamino)pyrrolidine-1-carboxylate.

Preparation 18 tert-butyl cis-3-methyl-4-(methylamino)pyrrolidine-1-carboxylate

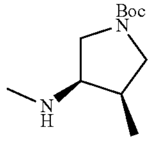

The procedure of Preparation 13 was performed except that tert-butyl cis-3-methyl-4-aminopyrrolidine-1-carboxylate was used instead of tert-butyl(3R,4R)-3-amino-4-ethylpyrrolidine-1-carboxylate, thereby obtaining tert-butyl cis-3-methyl-4-(methylamino)pyrrolidine-1-carboxylate.

Example 1

N-(azetidin-3-yl)-2-(((5-(tert-butyl)-6-chloro-1H-indazol-3-yl)amino)methyl)-4-chloro-N,1-dimethyl-1H-imidazole-5-carboxamide Step 1: To a mixture of 2-(((5-(tert-butyl)-6-chloro-1H-indazol-3-yl)amino)methyl)-4-chloro-1-methyl-1H-imidazole-5-carboxylic acid obtained in Preparation 4 (30 mg, 0.075 mmol), tert-butyl 3-(methylamino)azetidine-1-carboxylate (26 mg, 0.15 mmol) in DMF (0.75 mL), HATU (43 mg, 0.11 mmol) and DIPEA (26 L) were added at room temperature. The mixture was stirred at room temperature for 1 h. The mixture was diluted with EtOAc and water, extracted with EtOAc. The organic phase was washed with brine, dried over $Na_2SO_4$, filtered, and concentrated in vacuo. The residue was used in the next step without purification.

Step 2: Trifluoroacetic acid (0.5 mL) was added to the residue obtained in Step 1, and the mixture was stirred at room temperature for 30 minutes, followed by concentrating the reaction mixture. The residue was purified by reverse phase preparative HPLC to give N-(azetidin-3-yl)-2-(((5-(tert-butyl)-6-chloro-1H-indazol-3-yl)amino)methyl)-4-chloro-N,1-dimethyl-1H-imidazole-5-carboxamide (15 mg) as a white solid.

Example 2

(S)-2-(((5-(tert-butyl)-6-chloro-1H-indazol-3-yl)amino)methyl)-4-chloro-N,1-dimethyl-N-(pyrrolidin-3-yl)-1H-imidazole-5-carboxamide The procedure of Example 1 was performed except that tert-butyl (3S)-3-(methylamino)pyrrolidine-1-carboxylate was used instead of tert-butyl 3-(methylamino)azetidine-1-carboxylate, thereby obtaining (S)-2-(((5-(tert-butyl)-6-chloro-1H-indazol-3-yl)amino)methyl)-4-chloro-N,1-dimethyl-N-(pyrrolidin-3-yl)-1H-imidazole-5-carboxamide as a pale yellow solid.

Example 3

(R)-2-(((5-(tert-butyl)-6-chloro-1H-indazol-3-yl)amino)methyl)-4-chloro-N,1-dimethyl-N-(pyrrolidin-3-yl)-1H-imidazole-5-carboxamide The procedure of Example 1 was performed except that tert-butyl (3R)-3-(methylamino)pyrrolidine-1-carboxylate was used instead of tert-butyl 3-(methylamino)azetidine-1-carboxylate, thereby obtaining (R)-2-(((5-(tert-butyl)-6-chloro-1H-indazol-3-yl)amino)methyl)-4-chloro-N,1-dimethyl-N-(pyrrolidin-3-yl)-1H-imidazole-5-carboxamide as a white solid.

Example 4

(2-(((5-(tert-butyl)-6-chloro-1H-indazol-3-yl)amino)methyl)-4-chloro-1-methyl-1H-imidazol-5-yl)(1,4-diazepan-1-yl)methanone The procedure of Example 1 was performed except that tert-butyl 1,4-diazepane-1-carboxylate was used instead of tert-butyl 3-(methylamino)azetidine-1-carboxylate, thereby obtaining (2-(((5-(tert-butyl)-6-chloro-1H-indazol-3-yl)amino)methyl)-4-chloro-1-methyl-1H-imidazol-5-yl)(1,4-diazepan-1-yl)methanone.

Example 5

2-(((5-(tert-butyl)-6-chloro-1H-indazol-3-yl)amino)methyl)-4-chloro-1-((R)-1-isopropylpyrrolidin-3-yl)-N-methyl-N-((R)-pyrrolidin-3-yl)-1H-imidazole-5-carboxamide Step 1: To a mixture of (R)-2-(((5-(tert-butyl)-6-chloro-1H-indazol-3-yl)amino)methyl)-4-chloro-1-(1-isopropylpyrrolidin-3-yl)-1H-imidazole-5-carboxylic acid obtained in Preparation 8 (30 mg, 0.061 mmol), tert-butyl (3R)-3-(methylamino)pyrrolidine-1-carboxylate (23 mg, 0.13 mmol) in DMF (0.61 mL), HATU (35 mg, 0.09 mmol) and DIPEA (26 L) were added at room temperature. The mixture was stirred at room temperature for 1 h. The mixture was diluted with EtOAc and water, extracted with EtOAc. The organic phase was washed with brine, dried over $Na_2SO_4$, filtered, and concentrated in vacuo. The residue was used in the next step without purification.

Step 2: Trifluoroacetic acid (0.5 mL) was added to the residue obtained in Step 1, and the mixture was stirred at room temperature for 30 minutes, followed by concentrating the reaction mixture. The residue was purified by reverse phase preparative HPLC to give 2-(((5-(tert-butyl)-6-chloro-1H-indazol-3-yl)amino)methyl)-4-chloro-1-((R)-1-isopropylpyrrolidin-3-yl)-N-methyl-N-((R)-pyrrolidin-3-yl)-1H-imidazole-5-carboxamide (12 mg) as a white solid.

Example 6

(R)-N-(azetidin-3-yl)-2-(((5-(tert-butyl)-6-chloro-1H-indazol-3-yl)amino)methyl)-4-chloro-1-(1-isopropylpyrrolidin-3-yl)-N-methyl-1H-imidazole-5-carboxamide The procedure of Example 5 was performed except that 5 tert-butyl 3-(methylamino)azetidine-1-carboxylate was used instead of tert-butyl (3R)-3-(methylamino)pyrrolidine-1-carboxylate, thereby obtaining (R)-N-(azetidin-3-yl)-2-(((5-(tert-butyl)-6-chloro-1H-indazol-3-yl)amino)methyl)-4-chloro-1-(1-isopropylpyrrolidin-3-yl)-N-methyl-1H-imidazole-5-carboxamide.

Example 7

N-(2-aminoethyl)-2-(((5-(tert-butyl)-6-chloro-1H-indazol-3-yl)amino)methyl)-4-chloro-N,1-dimethyl-1H-imidazole-5-carboxamide The procedure of Example 1 was performed except that tert-butyl N-[2-(methylamino)ethyl]carbamate was used instead of tert-butyl 3-(methylamino)azetidine-1-carboxylate, thereby obtaining N-(2-aminoethyl)-2-(((5-(tert-butyl)-6-chloro-1H-indazol-3-yl)amino)methyl)-4-chloro-N,1-dimethyl-1H-imidazole-5-carboxamide.

Example 8

(R)-N-(2-aminoethyl)-2-(((5-(tert-butyl)-6-chloro-JH-indazol-3-yl)amino)methyl)-4-chloro-1-(1-isopropylpyrrolidin-3-yl)-N-methyl-JH-imidazole-5-carboxamide The procedure of Example 5 was performed except that tert-butyl N-[2-(methylamino)ethyl]carbamate was used instead of tert-butyl (3R)-3-(methylamino)pyrrolidine-1-carboxylate, thereby obtaining (R)-N-(2-aminoethyl)-2-(((5-(tert-butyl)-6-chloro-1H-indazol-3-yl)amino)methyl)-4-chloro-1-(1-isopropylpyrrolidin-3-yl)-N-methyl-1H-imidazole-5-carboxamide.

Example 9

2-(((5-(tert-butyl)-6-chloro-1H-indazol-3-yl)amino)methyl)-4-chloro-N-((3R,4R)-4-ethylpyrrolidin-3-yl)-N,1-dimethyl-1H-imidazole-5-carboxamide The procedure of Example 1 was performed except that tert-butyl (3R,4R)-3-ethyl-4-(methylamino)pyrrolidine-1-carboxylate obtained in Preparation 13 was used instead of tert-butyl 3-(methylamino)azetidine-1-carboxylate, thereby obtaining 2-(((5-(tert-butyl)-6-chloro-1H-indazol-3-yl)amino)methyl)-4-chloro-N-((3R,4R)-4-ethylpyrrolidin-3-yl)-N,1-dimethyl-1H-imidazole-5-carboxamide.

Example 10

(S)-2-(((5-(tert-butyl)-6-chloro-1H-indazol-3-yl)amino)methyl)-4-chloro-N,1-dimethyl-N-(5-azaspiro[2.4]heptan-7-yl)-1H-imidazole-5-carboxamide Step 1: To a mixture of 2-(((5-(tert-butyl)-6-chloro-1H-indazol-3-yl)amino)methyl)-4-chloro-1-methyl-1H-imidazole-5-carboxylic acid obtained in Preparation 4 (15 mg, 0.038 mmol), benzyl (S)-7-(methylamino)-5-azaspiro[2.4]heptane-5-carboxylate obtained in Preparation 14 (20 mg) in DMF (0.75 mL), HATU (20 mg) and DIPEA (30 μL) were added at room temperature. The mixture was stirred at room temperature for 1 h. The mixture was diluted with EtOAc and water, extracted with EtOAc. The organic phase was washed with brine, dried over $Na_2SO_4$, filtered, and concentrated in vacuo. The residue was used in the next step without purification.

Step 2: 5% Palladium on carbon was added to the mixture of the crude residue in methanol (2 mL). The mixture was stirred at room temperature for 2 hours under hydrogen atmosphere. 5% Palladium on carbon was removed by filtration, the filtrate was evaporated under reduced pressure, and the residue was purified by reverse phase preparative HPLC to give (S)-2-(((5-(tert-butyl)-6-chloro-1H-indazol-3-yl)amino)methyl)-4-chloro-N,1-dimethyl-N-(5-azaspiro[2.4]heptan-7-yl)-1H-imidazole-5-carboxamide (7 mg) as a white solid.

Example 11

2-(((5-(tert-butyl)-6-chloro-1H-indazol-3-yl)amino)methyl)-4-chloro-N,1-dimethyl-N-(trans-(2-methylazetidin-3-yl)-1H-imidazole-5-carboxamide The procedure of Example 1 was performed except that tert-butyl trans-2-methyl-3-(methylamino)azetidine-1-carboxylate obtained in Preparation 15 was used instead of tert-butyl 3-(methylamino)azetidine-1-carboxylate, thereby obtaining 2-(((5-(tert-butyl)-6-chloro-1H-indazol-3-yl)amino)methyl)-4-chloro-N,1-dimethyl-N-(trans-(2-methylazetidin-3-yl)-1H-imidazole-5-carboxamide.

Example 12

2-(((5-(tert-butyl)-6-chloro-1H-indazol-3-yl)amino)methyl)-4-chloro-N,1-dimethyl-N-((1S,2S)-2-(methylamino)cyclopropyl)-1H-imidazole-5-carboxamide The procedure of Example 1 was performed except that tert-butyl N-methyl-N-[(1S,2S)-2-(methylamino)cyclopropyl]carbamate obtained in Preparation 16 was used instead of tert-butyl 3-(methylamino)azetidine-1-carboxylate, thereby obtaining 2-(((5-(tert-butyl)-6-chloro-1H-indazol-3-yl)amino)methyl)-4-chloro-N,1-dimethyl-N-((1S,2S)-2-(methylamino)cyclopropyl)-1H-imidazole-5-carboxamide.

Example 13

2-(((5-(tert-butyl)-6-chloro-1H-indazol-3-yl)amino)methyl)-4-chloro-N,1-dimethyl-N-(trans-4-methylpyrrolidin-3-yl)-1H-imidazole-5-carboxamide The procedure of Example 1 was performed except that tert-butyl trans-3-methyl-4-(methylamino)pyrrolidine-1-carboxylate obtained in Preparation 17 was used instead of tert-butyl 3-(methylamino)azetidine-1-carboxylate, thereby obtaining 2-(((5-(tert-butyl)-6-chloro-1H-indazol-3-yl)amino)methyl)-4-chloro-N,1-dimethyl-N-(trans-4-methylpyrrolidin-3-yl)-1H-imidazole-5-carboxamide.

Example 14

2-(((5-(tert-butyl)-6-chloro-1H-indazol-3-yl)amino)methyl)-4-chloro-N,1-dimethyl-N-(cis-4-methylpyrrolidin-3-yl)-1H-imidazole-5-carboxamide The procedure of Example 1 was performed except that tert-butyl cis-3-methyl-4-(methylamino)pyrrolidine-1-carboxylate obtained in Preparation 18 was used instead of tert-butyl 3-(methylamino)azetidine-1-carboxylate, thereby obtaining 2-(((5-(tert-butyl)-6-chloro-1H-indazol-3-yl)amino)methyl)-4-chloro-N,1-dimethyl-N-(cis-4-methylpyrrolidin-3-yl)-1H-imidazole-5-carboxamide.

Example 15

(R)-2-(((5-(tert-butyl)-4-chloro-2-hydroxyphenyl)amino)methyl)-4-chloro-N,1-dimethyl-N-(pyrrolidin-3-yl)-1H-imidazole-5-carboxamide The procedure of Example 3 was performed except that 2-(((5-(tert-butyl)-4-chloro-2-hydroxyphenyl)amino)

methyl)-4-chloro-1-methyl-1H-imidazole-5-carboxylic acid obtained in Preparation 10 was used instead of 2-(((5-(tert-butyl)-6-chloro-1H-indazol-3-yl)amino)methyl)-4-chloro-1-methyl-1H-imidazole-5-carboxylic acid, thereby obtaining (R)-2-(((5-(tert-butyl)-4-chloro-2-hydroxyphenyl)amino)methyl)-4-chloro-N,1-dimethyl-N-(pyrrolidin-3-yl)-1H-imidazole-5-carboxamide.

Example 16

(S)-2-(((5-(tert-butyl)-4-chloro-2-hydroxyphenyl)amino)methyl)-4-chloro-N,1-dimethyl-N-(pyrrolidin-3-yl)-1H-imidazole-5-carboxamide The procedure of Example 2 was performed except that 2-(((5-(tert-butyl)-4-chloro-2-hydroxyphenyl)amino)methyl)-4-chloro-1-methyl-1H-imidazole-5-carboxylic acid obtained in Preparation 10 was used instead of 2-(((5-(tert-butyl)-6-chloro-1H-indazol-3-yl)amino)methyl)-4-chloro-1-methyl-1H-imidazole-5-carboxylic acid, thereby obtaining (S)-2-(((5-(tert-butyl)-4-chloro-2-hydroxyphenyl)amino)methyl)-4-chloro-N,1-dimethyl-N-(pyrrolidin-3-yl)-1H-imidazole-5-carboxamide.

Example 17

N-(azetidin-3-yl)-2-(((5-(tert-butyl)-4-chloro-2-hydroxyphenyl)amino)methyl)-4-chloro-N,1-dimethyl-1H-imidazole-5-carboxamide The procedure of Example 1 was performed except that 2-(((5-(tert-butyl)-4-chloro-2-hydroxyphenyl)amino)methyl)-4-chloro-1-methyl-1H-imidazole-5-carboxylic acid obtained in Preparation 10 was used instead of 2-(((5-(tert-butyl)-6-chloro-1H-indazol-3-yl)amino)methyl)-4-chloro-1-methyl-1H-imidazole-5-carboxylic acid, thereby obtaining N-(azetidin-3-yl)-2-(((5-(tert-butyl)-4-chloro-2-hydroxyphenyl)amino)methyl)-4-chloro-N,1-dimethyl-1H-imidazole-5-carboxamide.

Example 18

2-(((5-(tert-butyl)-4-chloro-2-hydroxyphenyl)amino)methyl)-4-chloro-1-((R)-1-isopropylpyrrolidin-3-yl)-N-methyl-N-((R)-pyrrolidin-3-yl)-1H-imidazole-5-carboxamide The procedure of Example 5 was performed except that methyl (R)-1-(1-(tert-butoxycarbonyl)pyrrolidin-3-yl)-2-(((5-(tert-butyl)-4-chloro-2-hydroxyphenyl)amino)methyl)-4-chloro-1H-imidazole-5-carboxylate obtained in Preparation 12 was used instead of (R)-2-(((5-(tert-butyl)-6-chloro-1H-indazol-3-yl)amino)methyl)-4-chloro-1-(1-isopropylpyrrolidin-3-yl)-1H-imidazole-5-carboxylic acid, thereby obtaining 2-(((5-(tert-butyl)-4-chloro-2-hydroxyphenyl)amino)methyl)-4-chloro-1-((R)-1-isopropylpyrrolidin-3-yl)-N-methyl-N-((R)-pyrrolidin-3-yl)-1H-imidazole-5-carboxamide.

Example 19

2-(((5-(tert-butyl)-4-chloro-2-hydroxyphenyl)amino)methyl)-4-chloro-1-((R)-1-isopropylpyrrolidin-3-yl)-N-methyl-N-((S)-pyrrolidin-3-yl)-1H-imidazole-5-carboxamide The procedure of Example 5 was performed except that methyl (R)-1-(1-(tert-butoxycarbonyl)pyrrolidin-3-yl)-2-(((5-(tert-butyl)-4-chloro-2-hydroxyphenyl)amino)methyl)-4-chloro-1H-imidazole-5-carboxylate obtained in preparation 12 and tert-butyl (3S)-3-(methylamino)pyrrolidine-1-carboxylate was used instead of (R)-2-(((5-(tert-butyl)-6-chloro-1H-indazol-3-yl)amino)methyl)-4-chloro-1-(1-isopropylpyrrolidin-3-yl)-1H-imidazole-5-carboxylic acid and tert-butyl (3R)-3-(methylamino)pyrrolidine-1-carboxylate, thereby obtaining 2-(((5-(tert-butyl)-4-chloro-2-hydroxyphenyl)amino)methyl)-4-chloro-1-((R)-1-isopropylpyrrolidin-3-yl)-N-methyl-N-((S)-pyrrolidin-3-yl)-1H-imidazole-5-carboxamide.

Example 20

(R)-N-(azetidin-3-yl)-2-(((5-(tert-butyl)-4-chloro-2-hydroxyphenyl)amino)methyl)-4-chloro-1-(1-isopropylpyrrolidin-3-yl)-N-methyl-1H-imidazole-5-carboxamide The procedure of Example 6 was performed except that methyl (R)-1-(1-(tert-butoxycarbonyl)pyrrolidin-3-yl)-2-(((5-(tert-butyl)-4-chloro-2-hydroxyphenyl)amino)methyl)-4-chloro-1H-imidazole-5-carboxylate obtained in Preparation 12 was used instead of (R)-2-(((5-(tert-butyl)-6-chloro-1H-indazol-3-yl)amino)methyl)-4-chloro-1-(1-isopropylpyrrolidin-3-yl)-1H-imidazole-5-carboxylic acid, thereby obtaining (R)-N-(azetidin-3-yl)-2-(((5-(tert-butyl)-4-chloro-2-hydroxyphenyl)amino)methyl)-4-chloro-1-(1-isopropylpyrrolidin-3-yl)-N-methyl-1H-imidazole-5-carboxamide.

Example 21

2-(((5-(tert-butyl)-6-chloro-1H-indazol-3-yl)amino)methyl)-4-chloro-N,1-dimethyl-N-(pyrrolidin-3-yl)-1H-imidazole-5-carboxamide The procedure of Example 1 was performed except that tert-butyl 3-(methylamino)pyrrolidine-1-carboxylate was used instead of tert-butyl 3-(methylamino)azetidine-1-carboxylate, thereby obtaining 2-(((5-(tert-butyl)-6-chloro-1H-indazol-3-yl)amino)methyl)-4-chloro-N,1I-dimethyl-N-(pyrrolidin-3-yl)-1H-imidazole-5-carboxamide as a pale yellow solid.

The structure and NMR and MS information for each of the compounds prepared in Examples 1-21 are listed in Table 1 below.

TABLE 1

| Ex. No. | Structure | Name | NMR | ESI-MS [M + H]+ |
|---|---|---|---|---|
| 1 | 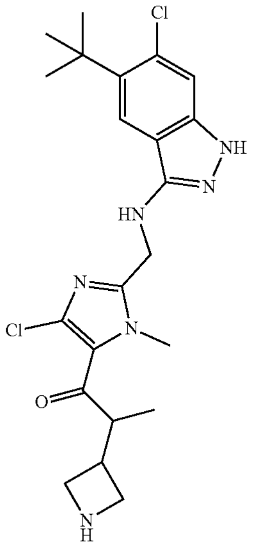 [SMILES: CC(C(=O)c1c(Cl)nc(CNc2n[nH]c3cc(Cl)c(C(C)(C)C)cc23)n1C)C1CNC1] | N-(azetidin-3-yl)-2-(((5-(tert-butyl)-6-chloro-1H-indazol-3-yl)amino)methyl)-4-chloro-N,1-dimethyl-1H-imidazole-5-carboxamide | 1H NMR (DMSO-d6, 400 MHz) δ 11.48 (s, 1H), 7.92 (s, 1H), 7.28 (s, 1H), 6.7-6.8 (m, 1H), 4.4-4.6 (m, 2H), 3.60 (s, 3H), 3.0-3.25 (s, 3H), 3.60-1.48 (m, 5H), 1.48 (s, 9H) | 464 |
| 2 | 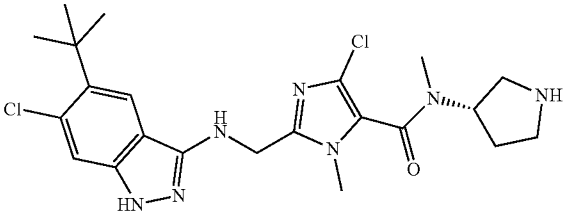 [SMILES: CN(C(=O)c1c(Cl)nc(CNc2n[nH]c3cc(Cl)c(C(C)(C)C)cc23)n1C)[C@H]1CCNC1] | (S)-2-(((5-(tert-butyl)-6-chloro-1H-indazol-3-yl)amino)methyl)-4-chloro-N,1-dimethyl-N-(pyrrolidin-3-yl)-1H-imidazole-5-carboxamide | 1H NMR (DMSO-d6, 400 MHz) δ 11.49 (s, 1H), 7.93 (s, 1H), 7.29 (s, 1H), 6.75 (s, 1H), 4.4-4.5 (m, 2H), 3.5-3.7 (m, 3H), 2.92 (s, 3H), 3.50-1.50 (m, 7H), 1.48 (s, 9H) | 478 |
| 3 | 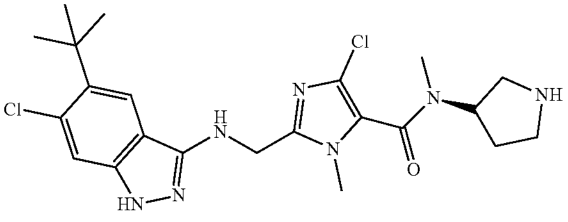 | (R)-2-(((5-(tert-butyl)-6-chloro-1H-indazol-3-yl)amino)methyl)-4-chloro-N,1-dimethyl-N-(pyrrolidin-3-yl)-1H-imidazole-5-carboxamide | 1H NMR (DMSO-d6, 400 MHz) δ 11.49 (s, 1H), 7.93 (s, 1H), 7.29 (s, 1H), 6.75 (s, 1H), 4.4-4.5 (m, 2H), 3.5-3.7 (m, 3H), 2.92 (s, 3H), 3.50-1.50 (m, 7H),1.48 (s, 9H) | 478 |
| 4 | 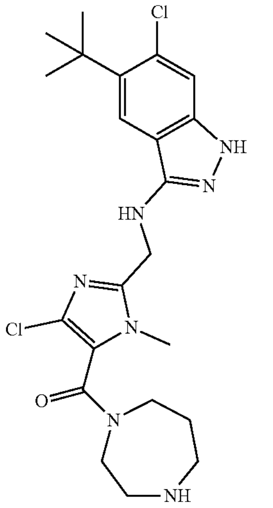 [SMILES: Cn1c(CNc2n[nH]c3cc(Cl)c(C(C)(C)C)cc23)nc(Cl)c1C(=O)N1CCCNCC1] | (2-(((5-(tert-butyl)-6-chloro-1H-indazol-3-yl)amino)methyl)-4-chloro-1-methyl-1H-imidazol-5-yl)(1,4-diazepan-1-yl)methanone | 0 | 478 |

TABLE 1-continued

| Ex. No. | Structure | Name | NMR | ESI-MS [M + H]+ |
|---|---|---|---|---|
| 5 | 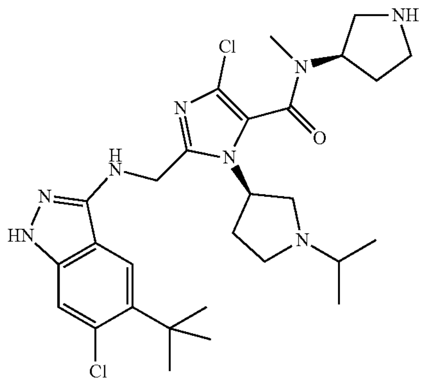 [SMILES: CC(C)N1CC[C@@H](n2c(CNc3n[nH]c4cc(Cl)c(C(C)(C)C)cc34)nc(Cl)c2C(=O)N(C)[C@@H]2CCNC2)C1] | 2-(((5-(tert-butyl)-6-chloro-1H-indazol-3-yl)amino)methyl)-4-chloro-1-((R)-1-isopropylpyrrolidin-3-yl)-N-methyl-N-((R)-pyrrolidin-3-yl)-1H-imidazole-5-carboxamide | 1H NMR (DMSO-d6, 400 MHz) δ 11.4-11.5 (m, 1H), 7.93 (s, 1H), 7.28 (s, 1H), 6.6-6.8 (m, 1H), 4.4-5.0 (m, 4H), 1.5-3.5 (m, 16H) 1.47 (s, 9H), 0.9-1.0 (m, 6H) | 575 |
| 6 | 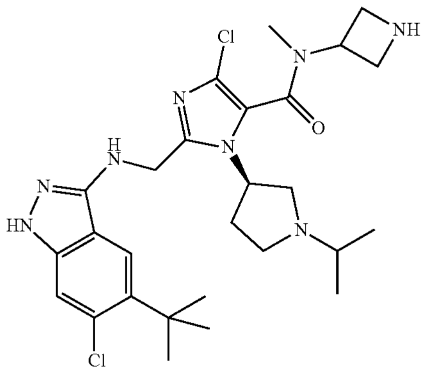 [SMILES: CC(C)N1CC[C@@H](n2c(CNc3n[nH]c4cc(Cl)c(C(C)(C)C)cc34)nc(Cl)c2C(=O)N(C)C2CNC2)C1] | (R)-N-(azetidin-3-yl)-2-(((5-(tert-butyl)-6-chloro-1H-indazol-3-yl)amino)methyl)-4-chloro-1-(1-isopropylpyrrolidin-3-yl)-N-methyl-1H-imidazole-5-carboxamide | 1H NMR (DMSO-d6, 400 MHz) δ 11.4-11.5 (m, 1H), 7.9-8.0 (m, 1H), 7.2-7.3 (m, 1H), 6.7-6.8 (m, 1H), 4.4-5.0 (m, 4H), 2.0-3.8 (m, 14H) 1.47 (s, 9H), 0.9-1.0 (m, 6H) | 561 |
| 7 | 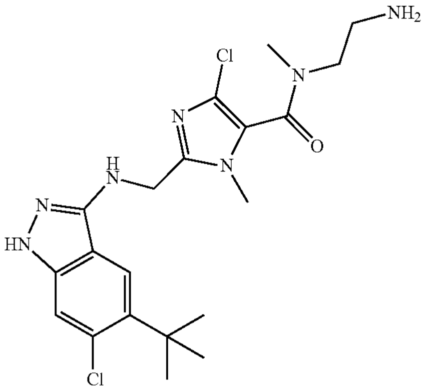 [SMILES: CN(CCN)C(=O)c1c(Cl)nc(CNc2n[nH]c3cc(Cl)c(C(C)(C)C)cc23)n1C] | N-(2-aminoethyl)-2-(((5-(tert-butyl)-6-chloro-1H-indazol-3-yl)amino)methyl)-4-chloro-N,1-dimethyl-1H-imidazole-5-carboxamide | 1H NMR (DMSO-d6, 400 MHz) δ 11.4-11.5 (m, 1H), 7.9-8.0 (m, 1H), 7.29 (s, 1H), 6.7-6.8 (m, 1H), 4.4-4.5 (m, 2H), 3.62 (s, 3H), 3.2 (m, 3H), 2.3-3.5 (m, 4H), 1.48 (s, 9H) | 452 |
| 8 | 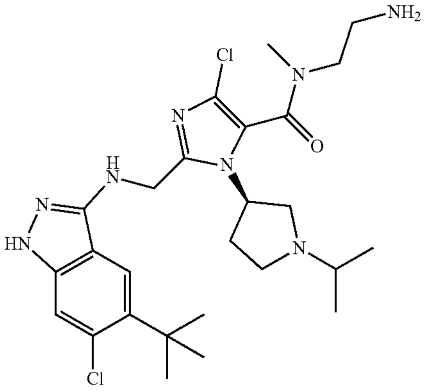 [SMILES: CC(C)N1CC[C@@H](n2c(CNc3n[nH]c4cc(Cl)c(C(C)(C)C)cc34)nc(Cl)c2C(=O)N(C)CCN)C1] | (R)-N-(2-aminoethyl)-2-(((5-(tert-butyl)-6-chloro-1H-indazol-3-yl)amino)methyl)-4-chloro-1-(1-isopropylpyrrolidin-3-yl)-N-methyl-1H-imidazole-5-carboxamide | 1H NMR (DMSO-d6, 400 MHz) δ 11.4-11.5 (m, 1H), 7.9-8.0 (m, 1H), 7.2-7.3 (m, 1H), 6.6-6.8 (m, 1H), 4.5-5.0 (m, 3H), 1.5-3.5 (m, 14H), 1.48 (s, 9H), 0.9-1.0 (m, 6H) | 549 |

TABLE 1-continued

| Ex. No. | Structure | Name | NMR | ESI-MS [M + H]+ |
| --- | --- | --- | --- | --- |
| 9 | 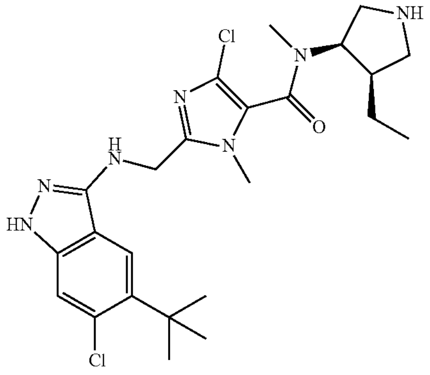 [SMILES: CC[C@@H]1CNC[C@@H]1N(C)C(=O)c1c(Cl)nc(CNc2n[nH]c3cc(Cl)c(C(C)(C)C)cc23)n1C] | 2-(((5-(tert-butyl)-6-chloro-1H-indazol-3-yl)amino)methyl)-4-chloro-N-((3R,4R)-4-ethylpyrrolidin-3-yl)-N,1-dimethyl-1H-imidazole-5-carboxamide | 1H NMR (DMSO-d6, 500 MHz) δ 11.5-11.5 (m, 1H), 7.9-8.0 (m, 1H), 7.2-7.3 (m, 1H), 6.7-6.8 (m, 1H), 4.4-4.6 (m, 2H), 3.61 (s, 3H), 2.0-3.2 (m, 9H), 1.48 (s, 9H), 1.1-1.3 (m, 2H), 0.8-1.0 (m, 3H) | 506 |
| 10 | 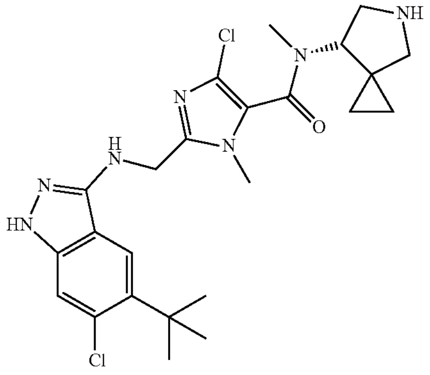 | (S)-2-(((5-(tert-butyl)-6-chloro-1H-indazol-3-yl)amino)methyl)-4-chloro-N,1-dimethyl-N-(5-azaspiro[2.4]heptan-7-yl)-1H-imidazole-5-carboxamide | 1H NMR (DMSO-d6, 500 MHz) δ 11.4-11.5 (m, 1H), 7.9-8.0 (m, 1H), 7.2-7.3 (m, 1H), 6.7-6.8 (m, 1H), 4.4-4.5 (m, 2H), 3.5-3.6 (m, 3H), 2.99 (s, 3H), 2.3-3.0 (m, 5H), 1.48 (s, 9H), 0.5-0.8 (m, 4H) | 504 |
| 11 | 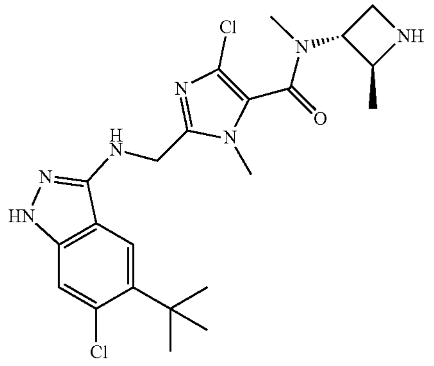 [SMILES: C[C@@H]1NC[C@H]1N(C)C(=O)c1c(Cl)nc(CNc2n[nH]c3cc(Cl)c(C(C)(C)C)cc23)n1C] | 2-(((5-(tert-butyl)-6-chloro-1H-indazol-3-yl)amino)methyl)-4-chloro-N,1-dimethyl-N-(trans-(2-methylazetidin-3-yl)-1H-imidazole-5-carboxamide | 1H NMR (DMSO-d6, 500 MHz) δ 11.4-11.5 (m, 1H), 7.92 (s, 1H), 7.28 (s, 1H), 6.7-6.8 (m, 1H), 4.4-4.6 (m, 2H), 3.9-4.0 (m, 1H), 3.5-3.7 (m, 4H), 3.0-3.1 (m, 3H), 2.4-2.7 (m, 2H), 1.48 (s, 9H), 0.5-0.8 (m, 3H) | 478 |
| 12 | 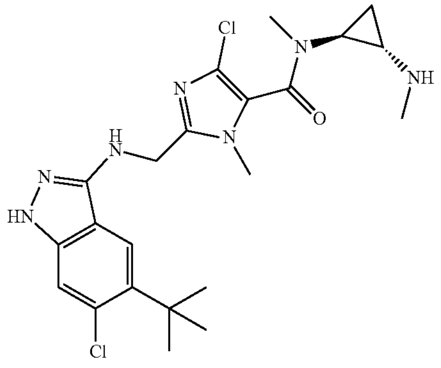 [SMILES: CN[C@H]1C[C@@H]1N(C)C(=O)c1c(Cl)nc(CNc2n[nH]c3cc(Cl)c(C(C)(C)C)cc23)n1C] | 2-(((5-(tert-butyl)-6-chloro-1H-indazol-3-yl)amino)methyl)-4-chloro-N,1-dimethyl-N-((1S,2S)-2-(methylamino)cyclopropyl)-1H-imidazole-5-carboxamide | 1H NMR (DMSO-d6, 500 MHz) δ 11.4-11.5 (m, 1H), 7.9-8.0 (m, 1H), 7.3-7.3 (m, 1H), 6.7-6.8 (m, 1H), 4.4-4.5 (m, 2H), 3.6-3.7 (m, 3H), 3.3-3.4 (m, 6H), 2.8-3.1 (m, 2H), 1.48 (s, 9H), 0.5-0.8 (m, 2H) | 478 |

TABLE 1-continued

| Ex. No. | Structure | Name | NMR | ESI-MS [M + H]+ |
|---|---|---|---|---|
| 13 | 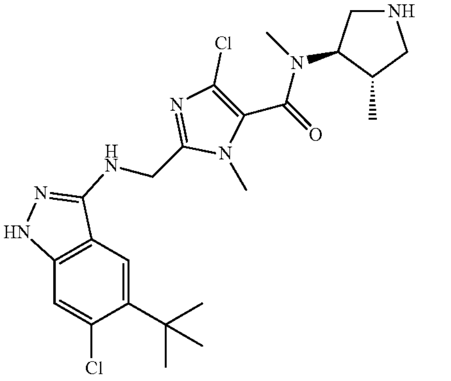 [SMILES: C[C@H]1CNC[C@@H]1N(C)C(=O)c1c(Cl)nc(CNc2n[nH]c3cc(Cl)c(C(C)(C)C)cc23)n1C] | 2-(((5-(tert-butyl)-6-chloro-1H-indazol-3-yl)amino)methyl)-4-chloro-N,1-dimethyl-N-(trans-4-methylpyrrolidin-3-yl)-1H-imidazole-5-carboxamide | 1H NMR (DMSO-d6, 400 MHz) δ 11.4-11.6 (m, 1H), 7.92 (s, 1H), 7.28 (s, 1H), 6.7-6.9 (m, 1H), 4.4-4.5 (m, 2H), 3.6-3.7 (m, 3H), 2.9-3.0 (m, 3H), 2.0-3.2 (m, 6H), 1.48 (s, 9H), 0.7-1.1 (m, 3H) | 492 |
| 14 | 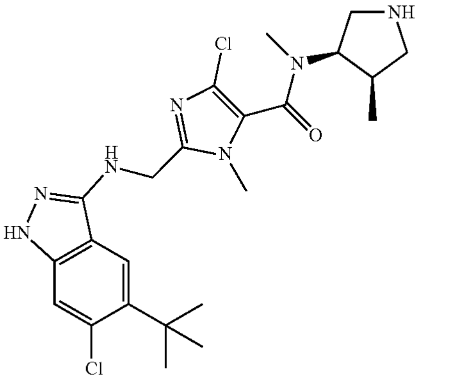 [SMILES: C[C@@H]1CNC[C@@H]1N(C)C(=O)c1c(Cl)nc(CNc2n[nH]c3cc(Cl)c(C(C)(C)C)cc23)n1C] | 2-(((5-(tert-butyl)-6-chloro-1H-indazol-3-yl)amino)methyl)-4-chloro-N,1-dimethyl-N-(cis-4-methylpyrrolidin-3-yl)-1H-imidazole-5-carboxamide | 1H NMR (DMSO-d6, 400 MHz) δ 11.49 (s, 1H), 7.9-8.0 (m, 1H), 7.29 (s, 1H), 6.7-6.8 (m, 1H), 4.4-4.6 (m, 2H), 3.5-3.7 (m, 3H), 2.9-3.0 (m, 3H), 2.0-3.2 (m, 6H), 1.48 (s, 9H), 0.8-1.0 (m, 3H) | 492 |
| 15 | 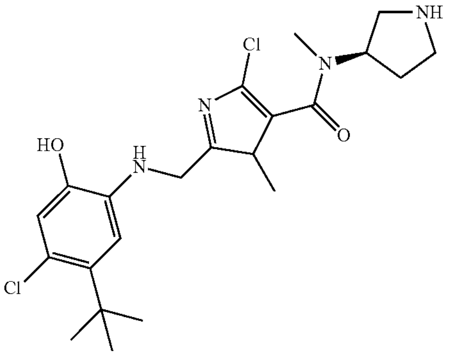 [SMILES: CC1C(CNc2cc(C(C)(C)C)c(Cl)cc2O)=NC(Cl)=C1C(=O)N(C)[C@@H]1CCNC1] | (R)-2-(((5-(tert-butyl)-4-chloro-2-hydroxyphenyl)amino) methyl)-4-chloro-N,1-dimethyl-N-(pyrrolidin-3-yl)-1H-imidazole-5-carboxamide | 1H NMR (DMSO-d6, 400 MHz) δ 9.5-9.7 (m, 1H), 6.79 (s, 1H), 6.64 (s, 1H), 5.4-5.5 (m, 1H), 4.3-4.4 (m, 2H), 3.54 (br s, 3H), 2.89 (s, 3H), 1.7-2.9 (m, 7H), 1.35 (s, 9H) | 454 |
| 16 | 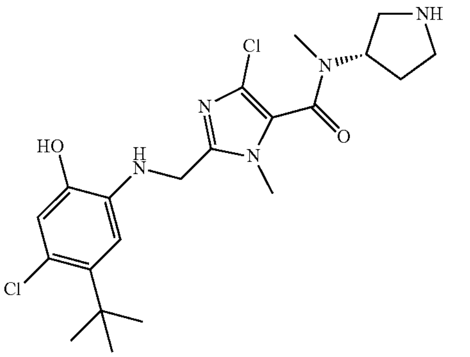 [SMILES: CN(C(=O)c1c(Cl)nc(CNc2cc(C(C)(C)C)c(Cl)cc2O)n1C)[C@H]1CCNC1] | (S)-2-(((5-(tert-butyl)-4-chloro-2-hydroxyphenyl)amino) methyl)-4-chloro-N,1-dimethyl-N-(pyrrolidin-3-yl)-1H-imidazole-5-carboxamide | 1H NMR (DMSO-d6, 400 MHz) δ 9.5-9.7 (m, 1H), 6.79 (s, 1H), 6.64 (s, 1H), 5.4-5.5 (m, 1H), 4.3-4.4 (m, 2H), 3.54 (br s, 3H), 2.89 (s, 3H), 1.7-2.9 (m, 7H), 1.35 (s, 9H) | 454 |

TABLE 1-continued

| Ex. No. | Structure | Name | NMR | ESI-MS [M + H]+ |
|---|---|---|---|---|
| 17 | 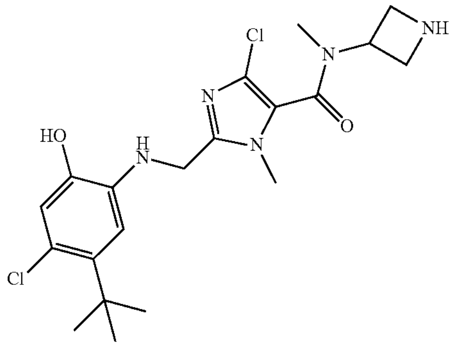 [SMILES: CN(C(=O)c1c(Cl)nc(CNc2cc(C(C)(C)C)c(Cl)cc2O)n1C)C1CNC1] | N-(azetidin-3-yl)-2-(((5-(tert-butyl)-4-chloro-2-hydroxyphenyl)amino)methyl)-4-chloro-N,1-dimethyl-1H-imidazole-5-carboxamide | 1H NMR (DMSO-d6, 400 MHz) δ 9.5-9.7 (m, 1H), 6.80 (s, 1H), 6.64 (s, 1H), 5.4-5.5 (m, 1H), 4.34 (s, 2H), 3.55 (br s, 6H), 3.0-3.5 (m, 5H), 1.36 (s, 9H) | 440 |
| 18 | 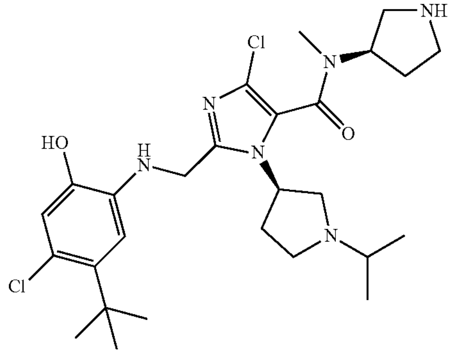 [SMILES: CC(C)N1CC[C@@H](n2c(CNc3cc(C(C)(C)C)c(Cl)cc3O)nc(Cl)c2C(=O)N(C)[C@@H]2CCNC2)C1] | 2-(((5-(tert-butyl)-4-chloro-2-hydroxyphenyl)amino)methyl)-4-chloro-1-((R)-1-isopropylpyrrolidin-3-yl)-N-methyl-N-((R)-pyrrolidin-3-yl)-1H-imidazole-5-carboxamide | 1H NMR (DMSO-d6, 400 MHz) δ 9.5-9.7 (m, 1H), 6.7-6.8 (m, 1H), 6.63 (s, 1H), 5.5-5.6 (m, 1H), 4.8-5.2 (m, 1H), 4.4-4.5 (m, 2H), 0.5-3.50 (m, 18H), 1.3-1.4 (m, 9H), 1.0 (m, 6H) | 551 |
| 19 | 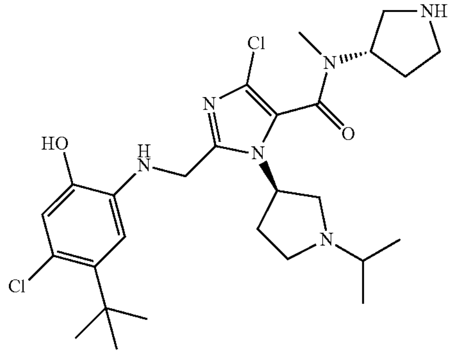 [SMILES: CC(C)N1CC[C@@H](n2c(CNc3cc(C(C)(C)C)c(Cl)cc3O)nc(Cl)c2C(=O)N(C)[C@H]2CCNC2)C1] | 2-(((5-(tert-butyl)-4-chloro-2-hydroxyphenyl)amino)methyl)-4-chloro-1-((R)-1-isopropylpyrrolidin-3-yl)-N-methyl-N-((S)-pyrrolidin-3-yl)-1H-imidazole-5-carboxamide | 1H NMR (DMSO-d6, 400 MHz) δ 9.5-9.7 (m, 1H), 6.7-6.8 (m, 1H), 6.63 (s, 1H), 5.5-5.6 (m, 1H), 4.8-5.2 (m, 1H), 4.4-4.5 (m, 2H), 0.5-3.50 (m, 18H), 1.3-1.4 (m, 9H), 1.0 (m, 6H) | 551 |
| 20 | 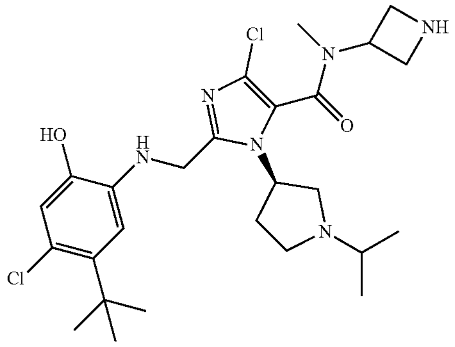 [SMILES: CC(C)N1CC[C@@H](n2c(CNc3cc(C(C)(C)C)c(Cl)cc3O)nc(Cl)c2C(=O)N(C)C2CNC2)C1] | (R)-N-(azetidin-3-yl)-2-(((5-(tert-butyl)-4-chloro-2-hydroxyphenyl)amino)methyl)-4-chloro-1-(1-isopropylpyrrolidin-3-yl)-N-methyl-1H-imidazole-5-carboxamide | 1H NMR (DMSO-d6, 400 MHz) δ 9.5-9.8 (m, 1H), 6.7-6.8 (m, 1H), 6.64 (s, 1H), 5.4-5.6 (m, 1H), 4.9-5.2 (m, 1H), 4.3-4.7 (m, 3H), 3.5-3.8 (m, 3H), 2.0-3.5 (m, 3H), 2.6-3.0 (m, 13H), 1.37 (s, 9H), 0.9-1.1 (m, 6H) | 537 |

TABLE 1-continued

| Ex. No. | Structure | Name | NMR | ESI-MS [M + H]+ |
|---|---|---|---|---|
| 21 | 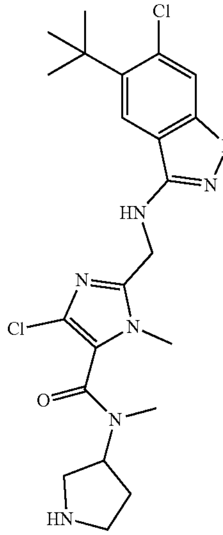 | 2-(((5-(tert-butyl)-6-chloro-1H-indazol-3-yl)amino)methyl)-4-chloro-N,1-dimethyl-N-(pyrrolidin-3-yl)-1H-imidazole-5-carboxamide | 1H NMR (DMSO-d6, 400 MHz) δ 11.49 (s, 1H), 7.93 (s, 1H), 7.29 (s, 1H), 6.75 (s, 1H), 4.4-4.5 (m, 2H), 3.5-3.7 (m, 3H), 2.92 (s, 3H), 3.50-1.50 (m, 7H), 1.48 (s, 9H) | |

Test Example: Evaluation of Inhibitory Activity of Compounds of Examples 1-21 on KRAS G12D Nucleotide (GDP-GTP) Exchange Reaction In Vitro Recombinant KRAS G12D (conjugated N-terminus $His_6$-tag, TEV protease cleavage site and KRAS G12D residues 1-169 (SEQ ID NO: 1), prepared by the method described below) and cleaved recombinant SOS1 (residues 564-1049 (SEQ ID NO: 2), prepared by the method described below) proteins were expressed in *E. coli* and purified by affinity chromatography.

To prepare the recombinant KRAS G12D, the codon-optimized DNA sequence for the recombinant KRAS G12D (conjugated N-terminus $His_6$-tag, TEV protease cleavage site and KRAS G12D residues 1-169 (SEQ ID NO: 3)) was synthesized by GeneArt Technology (Life Technologies, Carlsbad, California, US). The construct was subcloned into the expression vector pET28a and transformed into *Escherichia coli* BL21 (DE3) strains (Novagen, Madison, WI, USA).

The transformed strain was cultivated in 2 L Luria Broth medium with 25 g/mL kanamycin at a temperature of 37° C. to a density of 0.6 (OD600), then induced for expression with 500 mM IPTG and further cultivated for 4 h. The cell pellet was resuspended in ice-cold lysis buffer containing 50 mM Tris-HCl (pH 7.5), 200 mM NaCl, and 100 μM TCEP (tris(2-carboxyethyl)phosphine).

After sonication, the disrupted debris was removed by centrifugation. The supernatant was applied on to Ni-NTA affinity gels, and the recombinant human KRAS G12D eluted fraction was collected. The buffer of the collected fraction was exchanged to the buffer containing 50 mM Tris-HCl (pH 7.5), 200 mM NaCl, 10% Glycerol, and 5 mM DTT by PD-10 column (GE Healthcare, Chicago, Illinois, US).

To prepare the cleaved recombinant SOS1, the codon optimized DNA sequence for the recombinant SOS1 (residues 564-1049 with a conjugated N-terminus $His_6$-tag and TEV protease cleavage site (SEQ ID NO: 4)) was synthesized by GeneArt Technology (Life Technologies). The construct was subcloned into the expression vector pET28a and transformed into *Escherichia coli* BL21 (DE3) strains (Novagen, Madison, WI, USA). The transformed strain was cultivated in 2 L Terrific Broth medium with 25 μg/mL kanamycin at a temperature of 37° C. to a density of 0.8 (OD600), then shifted to a temperature of 16° C., induced for expression with 400 mM IPTG (isopropyl β-d-1-thiogalactopyranoside), and further cultivated for 16 h. The cell pellet was resuspended in ice-cold lysis buffer containing 50 mM Tris-HCl (pH 7.5), 200 mM NaCl, and 100 μM TCEP.

After sonication, the disrupted debris was removed by centrifugation. The supernatant was applied on to Ni-NTA affinity gels, and the recombinant human SOS1 eluted fraction was collected. Then, $His_6$-tagged TEV protease was added to the collected fraction, dialyzed with the ice-cold lysis buffer for 16 h at a temperature of 4° C., and applied on to Ni-NTA affinity gels. The flow-through fraction containing the tag-cleaved recombinant human SOS1 was collected. The buffer of the collected fraction was exchanged to the buffer containing 50 mM Tris-HCl (pH 7.5), 200 mM NaCl, 10% Glycerol, and 5 mM DTT by PD-10 column (GE Healthcare).

To prepare BODIPY FL (fluorescent dye) GDP-bound KRAS G12D protein, 50 μM KRAS G12D protein was incubated with 0.5 mM BODIPY FL GDP in a loading buffer (20 mM Tris-HCl (pH 7.5), 50 mM NaCl, 1 mM DTT and 2.5 mM EDTA) for 1 hour on ice. After the incubation, $MgCl_2$ was added to a final concentration of 10 mM, followed by incubation at room temperature for 30 minutes.

The mixture was allowed to pass through a NAP-5 column to remove free nucleotides, and purified BODIPY FL GDP-bound KRAS G12D protein was used for compound evaluation.

For the measurement of the inhibitory activity of compounds on GDP-GTP exchange rate of recombinant KRAS G12D, BODIPY FL GDP-bound KRAS G12D protein was incubated with various concentrations of compounds of Formula (I), i.e., compounds of Examples 1-21, in a reaction buffer (20 mM Tris-HCl (pH 7.5), 100 mM NaCl, 1 mM MgCl2, 2 mM DTT, 0.1% Tween 20) at 25° C. for 1 hour.

After the incubation, recombinant SOS1 and GMPPNP (guanosine-5'-[(β,γ)-imido]triphosphate, tetralithium salt) (Jena Bioscience GmbH, Jena, Germany) were added and incubated at room temperature for 30 minutes to proceed SOS1-dependent GDP-GTP exchange reaction on KRAS G12D. Replacement of BODIPY FL GDP by GMPPNP was measured by calculating the ratio of fluorescence intensities of BODIPY FL before and after the exchange reaction.

Inhibition % was calculated by setting the fluorescence ratio from the reaction without test compound (DMSO control) and the fluorescence ratio from the reaction without SOS1 and GMPPNP as 0% and 100% inhibition, respectively. IC50 values were calculated from a dose titration curve using curve fitting by XLfit software (IDBS, Boston, Massachusetts, US). Table 2 shows the inhibitory activity IC50 (μM) of the compounds of Examples 1-21.

TABLE 2

| Number | Exchange G12D IC50 (μM) |
|---|---|
| 1 | 20.7 |
| 2 | 12.4 |
| 3 | 18.7 |
| 4 | 38.0 |
| 5 | 1.3 |
| 6 | 3.8 |
| 7 | 43.5 |
| 8 | 35.3 |
| 9 | 33.5 |
| 10 | 46.9 |
| 11 | 43.7 |
| 12 | 38.2 |
| 13 | 17.1 |
| 14 | 43.1 |
| 15 | 32.9 |
| 16 | 26.2 |
| 17 | 12.0 |
| 18 | 1.6 |
| 19 | 3.7 |
| 20 | 3.2 |
| 21 | 31.5 |

Protein Sequences

Recombinant KRAS G12D (conjugated N-terminus $His_6$-tag, TEV protease cleavage site and KRAS G12D residues 1-169)

(SEQ ID NO: 1)
MASSHHHHHHSSENLYFQGMTEYKLVVVGADGVGKSALTIQLIQNHFVD
EYDPTIEDSYRKQVVIDGETCLLDILDTAGQEEYSAMRDQYMRTGEGFL
CVFAINNTKSFEDIHHYREQIKRVKDSEDVPMVLVGNKCDLPSRTVDTK
QAQDLARSYGIPFIETSAKTRQGVDDAFYTLVREIRKHKEK

Cleaved Recombinant SOS1 (Residues 564-1049)

(SEQ ID NO: 2)
GEEQMRLPSADVYRFAEPDSEENIIFEENMQPKAGIPIIKAGTVIKLIE
RLTYHMYADPNFVRTFLTTYRSFCKPQELLSLIIERFEIPEPEPTEADR
IAIENGDQPLSAELKRFRKEYIQPVQLRVLNVCRHWVEHHFYDFERDAY
LLQRMEEFIGTVRGKAMKKWVESITKIIQRKKIARDNGPGHNITFQSPS
PTVEWHISRPGHIETFDLLTLHPIEIARQLTLLESDLYRAVQPSELVGS
VWTKEDKEINSPNLLKMIRHTTNLTLWFEKCIVETENLEERVAVVSRII

-continued

EILQVFQELNNFNGVLEVVSAMNSSPVYRLDHTFEQIPSRQKKILEEAH
ELSEDHYKKYLAKLRSINPPCVPFFGIYLTNILKTEEGNPEVLKRHGKE
LINFSKRRKVAEITGEIQQYQNQPYCLRVESDIKRFFENLNPMGNSMEK
EFTDYLFNKSLEIEPRNPKPLPRFPKKYSYPLKSPGVRPSNPRPGT

DNA Sequences

For expressing recombinant KRAS G12D (conjugated N-terminus $His_6$-tag, TEV protease cleavage site and KRAS G12D residues 1-169)

(SEQ ID NO: 3)
ATGGCAAGCAGCCATCATCATCATCATCATAGCAGCGAAAACCTGTATT
TTCAGGGCATGACCGAATATAAACTGGTTGTTGTTGGTGCAGATGGTGT
TGGTAAAAGCGCACTGACCATTCAGCTGATTCAGAATCATTTTGTGGAT
GAGTATGATCCGACCATCGAAGATAGCTATCGTAAACAGGTTGTGATTG
ATGGTGAAACCTGTCTGCTGGATATTCTGGATACCGCAGGTCAAGAGGA
ATATAGCGCAATGCGTGATCAGTATATGCGTACCGGTGAAGGTTTTCTG
TGTGTTTTTGCAATCAACAATACCAAAAGCTTCGAGGATATCCATCATT
ATCGCGAGCAGATTAAACGTGTGAAAGATAGCGAAGATGTTCCGATGGT
TCTGGTTGGTAATAAATGTGATCTGCCGAGCCGTACCGTTGATACCAAA
CAGGCACAGGATCTGGCACGTAGCTATGGTATTCCGTTTATTGAAACCA
GCGCAAAAACCCGTCAGGGTGTTGATGATGCATTTTATACCCTGGTTCG
TGAAATCCGCAAACATAAAGAAAAATGA

For expressing recombinant SOS1 (residues 564-1049 with a conjugated N-terminus $His_6$-tag and TEV protease cleavage site)

(SEQ ID NO: 4)
ATGGGCAGCAGCCATCATCATCATCATCACAGCAGCGGCCTGGTGCCGC
GCGGCAGCCATATGGCTAGCATGACTGGTGGACAGCAAATGGGTCGCGG
ATCCGAAAACCTGTATTTTCAGGGCGAGGAGCAGATGAGGCTGCCTAGT
GCTGATGTTTATAGATTTGCAGAGCCTGACTCTGAAGAGAATATTATAT
TTGAAGAGAACATGCAGCCCAAGGCTGGAATTCCAATTATCAAAGCAGG
AACTGTTATTAAACTTATAGAGAGGCTTACGTACCATATGTACGCAGAT
CCCAATTTTGTTCGGACATTTCTTACAACATACAGATCCTTTTGCAAAC
CTCAAGAACTACTGAGTCTTATAATAGAAAGGTTTGAAATTCCAGAGCC
TGAGCCAACAGAAGCTGATCGCATAGCTATAGAGAATGGAGATCAACCC
TTGAGTGCAGAACTGAAAAGATTTAGAAAAGAATATATACAGCCTGTGC
AACTGCGAGTATTAAATGTATGTCGGCACTGGGTAGAGCACCACTTCTA
TGATTTTGAAAGAGATGCATATCTTTTGCAACGAATGGAAGAATTTATT
GGAACAGTAAGAGGTAAAGCAATGAAAAAATGGGTTGAATCCATCACTA
AAATAATCCAAAGGAAAAAAATTGCAAGAGACAATGGACCAGGTCATAA
TATTACATTTCAGAGTTCACCTCCCACAGTTGAGTGGCATATAAGCAGA
CCTGGGCACATAGAGACTTTTGACCTGCTCACCTTACACCCAATAGAAA
TTGCTCGACAACTCACTTTACTTGAATCAGATCTATACCGAGCTGTACA

-continued

GCCATCAGAATTAGTTGGAAGTGTGTGGACAAAAGAAGACAAAGAAATT
AACTCTCCTAATCTTCTGAAAATGATTCGACATACCACCAACCTCACTC
TGTGGTTTGAGAAATGTATTGTAGAAACTGAAAATTTAGAAGAAAGAGT
AGCTGTGGTGAGTCGAATTATTGAGATTCTACAAGTCTTTCAAGAGTTG
AACAACTTTAATGGTGTCCTTGAGGTTGTCAGTGCTATGAATTCATCAC
CTGTTTACAGACTAGACCACACATTTGAGCAAATACCAAGTCGCCAGAA
GAAAATTTTAGAAGAAGCTCATGAATTGAGTGAAGATCACTATAAGAAA
TATTTGGCAAAACTCAGGTCTATTAATCCACCATGTGTGCCTTTCTTTG
GAATTTATCTCACTAATATCTTGAAAACAGAAGAAGGCAACCCTGAGGT
CCTAAAAAGACATGGAAAAGAGCTTATAAACTTTAGCAAAAGGAGGAAA
GTAGCAGAAATAACAGGAGAGATCCAGCAGTACCAAAATCAGCCTTACT
GTTTACGAGTAGAATCAGATATCAAAAGGTTCTTTGAAAACTTGAATCC
GATGGGAAATAGCATGGAGAAGGAATTTACAGATTATCTTTTCAACAAA
TCCCTAGAAATAGAACCACGAAACCCTAAGCCTCTCCCAAGATTTCCAA
AAAAATATAGCTATCCCCTAAAATCTCCTGGTGTTCGTCCATCAAACC
CAAGACCAGGTACCTAA

What is claimed is:

1. A compound of Formula (I) or a pharmaceutically acceptable salt thereof (I)

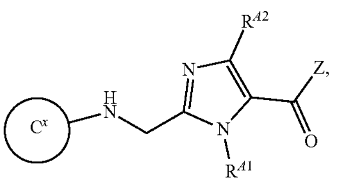

wherein ring $C^x$ is

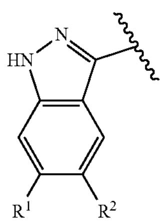

or

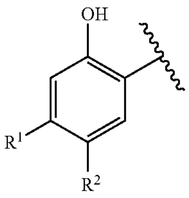

;

$R^1$ is halo;

$R^2$ is $C_1$-$C_6$ alkyl;

$R^{A1}$ is $C_1$-$C_6$ alkyl or ring $C^{A1}$, ring $C^{A1}$ being (a) a 4- to 8-membered saturated monocyclic heterocyclic ring containing from 1 to 2 heteroatoms selected from the group consisting of N, O, and S or (b) $C_3$-$C_6$ cycloalkyl, and ring $C^{A1}$ being unsubstituted or substituted by one to three substituents selected from the group consisting of halo, $C_1$-$C_6$ alkyl, $C_1$-$C_6$ fluoroalkyl, amino, hydroxy, and cyano;

$R^{A2}$ is chloro; and

Z is

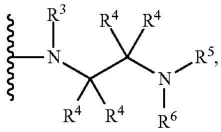

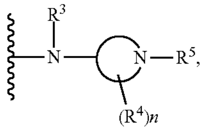

or

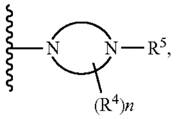

where

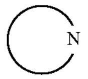

represents a 3- to 5-membered saturated monocyclic heterocyclic ring containing the illustrated nitrogen atom and optionally one additional heteroatom selected from the group consisting of O and S;

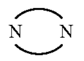

represents a 7- to 8-membered saturated monocyclic heterocyclic ring containing the illustrated nitrogen atoms and optionally one additional heteroatom selected from the group consisting of O and S;

$R^3$ is methyl;

each $R^4$ is independently selected from the group consisting of hydrogen, fluoro, $C_1$-$C_6$ alkyl, and $C_1$-$C_6$ fluoroalkyl, or alternatively, any two $R^4$ moieties, together with the carbon atom or atoms to which they are attached, form a cyclopropyl moiety or an aziridinyl moiety;

n is 0, 1, 2, or 3;

$R^5$ is hydrogen; and $R^6$ is hydrogen, or, when two $R^4$ moieties, together with the carbon atom or atoms to which they are attached, form a cyclopropyl moiety, $R^6$ is methyl, with the following provisos:

(a) when Z is

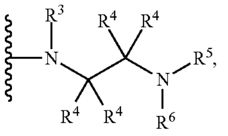

Z is not

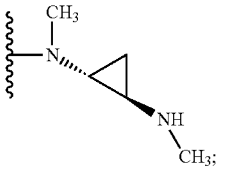

(b) when Z is

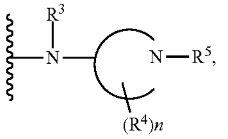

Z is not

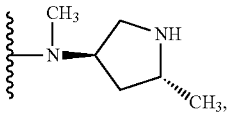 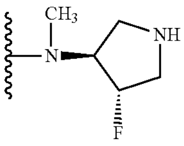 ,

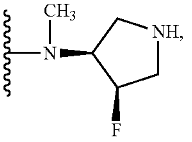 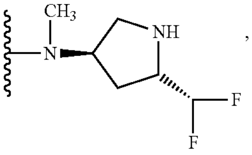 ,

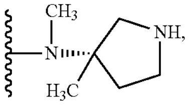 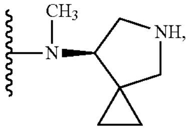

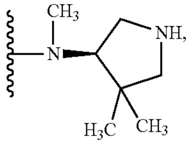 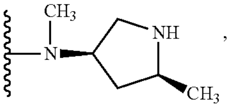 ,

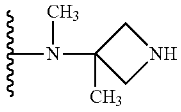 or 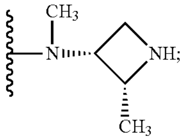

and (c) when Z is

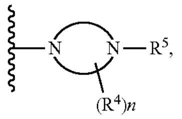

$R^4$ is not methyl.

2. The compound of claim 1 or the pharmaceutically acceptable salt thereof, wherein ring $C^x$ is

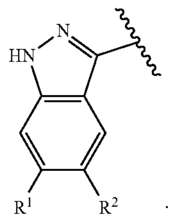

.

3. The compound of claim 1 or the pharmaceutically acceptable salt thereof, wherein ring $C^x$ is

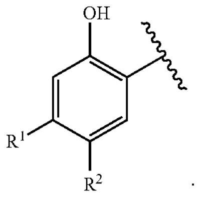

.

4. The compound of claim 1 or the pharmaceutically acceptable salt thereof, wherein $R^1$ is chloro.

5. The compound of claim 1 or the pharmaceutically acceptable salt thereof, wherein $R^2$ is tert-butyl.

6. The compound of claim 1 or the pharmaceutically acceptable salt thereof, wherein $R^{A1}$ is methyl.

7. The compound of claim 1 or the pharmaceutically acceptable salt thereof, wherein $R^{A1}$ is ring $C^{A1}$, and wherein ring $C^{A1}$ is a substituted or unsubstituted 5- to 6-membered saturated monocyclic heterocyclic ring containing from 1 to 2 N heteroatoms.

8. The compound of claim 7 or the pharmaceutically acceptable salt thereof, wherein ring $C^{A1}$ is unsubstituted pyrrolidinyl or pyrrolidinyl substituted by one $C_1$-$C_6$ alkyl.

9. The compound of claim 1 or the pharmaceutically acceptable salt thereof, wherein Z is

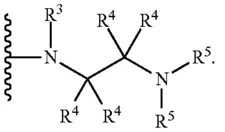

10. The compound of claim 9 or the pharmaceutically acceptable salt thereof, wherein Z is

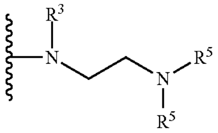 or 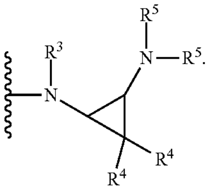

11. The compound of claim 1 or the pharmaceutically acceptable salt thereof, wherein Z is

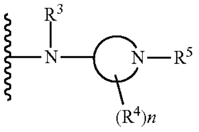 or 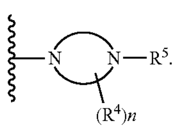

12. The compound of claim 11 or the pharmaceutically acceptable salt thereof, wherein Z is

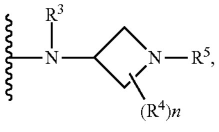 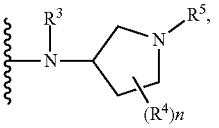 or

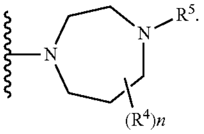

13. The compound of claim 1 or the pharmaceutically acceptable salt thereof, wherein Z is

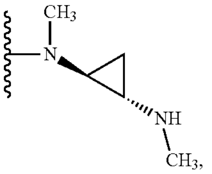

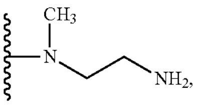

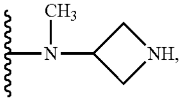

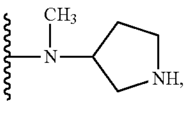

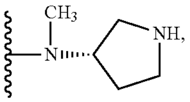

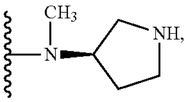

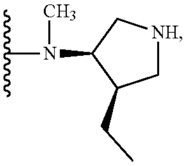

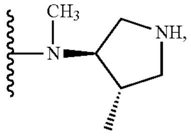

-continued

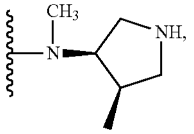

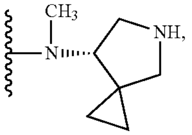

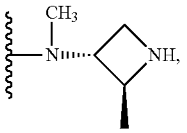 or 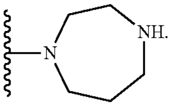

14. The compound of claim 1 or the pharmaceutically acceptable salt thereof, wherein the compound of Formula (I) has Formula (IA)

(IA)

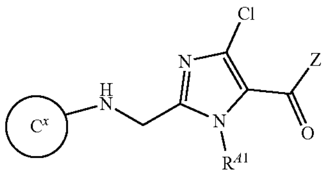

wherein ring $C^x$ is or

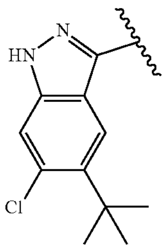 or 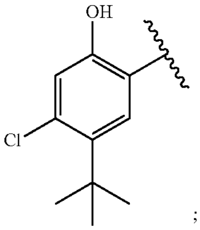 ;

$R^{A1}$ is methyl or

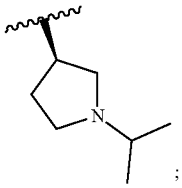 [SMILES: *[C@@H]1CCN(C(C)C)C1] ;

and

Z is selected from the group consisting of

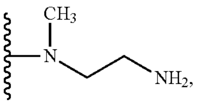

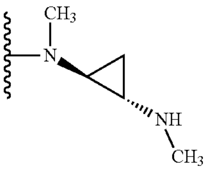 ,

-continued

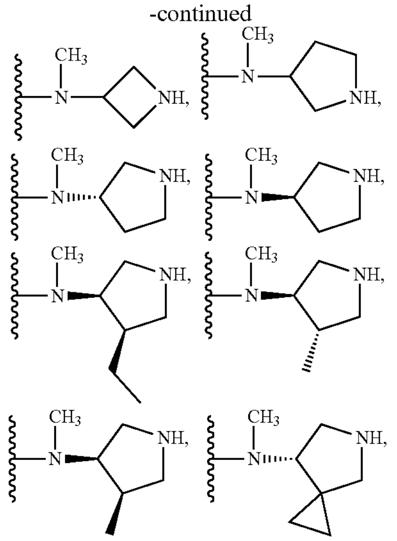

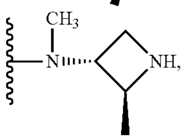

and

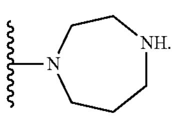

15. The compound of claim 14 or the pharmaceutically acceptable salt thereof, wherein ring $C^x$ is

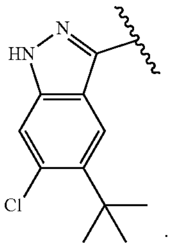 [SMILES: *c1n[nH]c2cc(Cl)c(C(C)(C)C)cc12]

16. The compound of claim 14 or the pharmaceutically acceptable salt thereof, wherein ring $C^x$ is

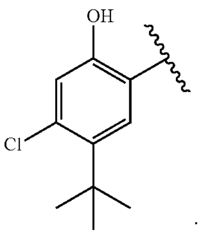 [SMILES: *c1cc(C(C)(C)C)c(Cl)cc1O]

17. A compound selected from the group consisting of:

N-(azetidin-3-yl)-2-(((5-(tert-butyl)-6-chloro-1H-indazol-3-yl)amino)methyl)-4-chloro-N,1-dimethyl-1H-imidazole-5-carboxamide, (S)-2-(((5-(tert-butyl)-6-chloro-1H-indazol-3-yl)amino)methyl)-4-chloro-N,1-dimethyl-N-(pyrrolidin-3-yl)-1H-imidazole-5-carboxamide, (R)-2-(((5-(tert-butyl)-6-chloro-1H-indazol-3-yl)amino)methyl)-4-chloro-N,1-dimethyl-N-(pyrrolidin-3-yl)-1H-imidazole-5-carboxamide, (2-(((5-(tert-butyl)-6-chloro-1H-indazol-3-yl)amino)methyl)-4-chloro-1-methyl-1H-imidazol-5-yl)(1,4-diazepan-1-yl)methanone, 2-(((5-(tert-butyl)-6-chloro-1H-indazol-3-yl)amino)methyl)-4-chloro-1-((R)-1-isopropylpyrrolidin-3-yl)-N-methyl-N-((R)-pyrrolidin-3-yl)-1H-imidazole-5-carboxamide, (R)-N-(azetidin-3-yl)-2-(((5-(tert-butyl)-6-chloro-1H-indazol-3-yl)amino)methyl)-4-chloro-1-(1-isopropylpyrrolidin-3-yl)-N-methyl-1H-imidazole-5-carboxamide, N-(2-aminoethyl)-2-(((5-(tert-butyl)-6-chloro-1H-indazol-3-yl)amino)methyl)-4-chloro-N,1-dimethyl-1H-imidazole-5-carboxamide, (R)-N-(2-aminoethyl)-2-(((5-(tert-butyl)-6-chloro-1H-indazol-3-yl)amino)methyl)-4-chloro-1-(1-isopropylpyrrolidin-3-yl)-N-methyl-1H-imidazole-5-carboxamide, 2-(((5-(tert-butyl)-6-chloro-1H-indazol-3-yl)amino)methyl)-4-chloro-N-((3R,4R)-4-ethylpyrrolidin-3-yl)-N,1-dimethyl-1H-imidazole-5-carboxamide, (S)-2-(((5-(tert-butyl)-6-chloro-1H-indazol-3-yl)amino)methyl)-4-chloro-N,1-dimethyl-N-(5-azaspiro[2.4]heptan-7-yl)-1H-imidazole-5-carboxamide, 2-(((5-(tert-butyl)-6-chloro-1H-indazol-3-yl)amino)methyl)-4-chloro-N,1-dimethyl-N-(trans-(2-methylazetidin-3-yl)-1H-imidazole-5-carboxamide, 2-(((5-(tert-butyl)-6-chloro-1H-indazol-3-yl)amino)methyl)-4-chloro-N,1-dimethyl-N-((1S,2S)-2-(methylamino)cyclopropyl)-1H-imidazole-5-carboxamide, 2-(((5-(tert-butyl)-6-chloro-1H-indazol-3-yl)amino)methyl)-4-chloro-N,1-dimethyl-N-(trans-4-methylpyrrolidin-3-yl)-1H-imidazole-5-carboxamide, 2-(((5-(tert-butyl)-6-chloro-1H-indazol-3-yl)amino)methyl)-4-chloro-N,1-dimethyl-N-(cis-4-methylpyrrolidin-3-yl)-1H-imidazole-5-carboxamide, (R)-2-(((5-(tert-butyl)-4-chloro-2-hydroxyphenyl)amino)methyl)-4-chloro-N,1-dimethyl-N-(pyrrolidin-3-yl)-1H-imidazole-5-carboxamide, (S)-2-(((5-(tert-butyl)-4-chloro-2-hydroxyphenyl)amino)methyl)-4-chloro-N,1-dimethyl-N-(pyrrolidin-3-yl)-1H-imidazole-5-carboxamide, N-(azetidin-3-yl)-2-(((5-(tert-butyl)-4-chloro-2-hydroxyphenyl)amino)methyl)-4-chloro-N,1-dimethyl-1H-imidazole-5-carboxamide, 2-(((5-(tert-butyl)-4-chloro-2-hydroxyphenyl)amino)methyl)-4-chloro-1-((R)-1-isopropylpyrrolidin-3-yl)-N-methyl-N-((R)-pyrrolidin-3-yl)-1H-imidazole-5-carboxamide, 2-(((5-(tert-butyl)-4-chloro-2-hydroxyphenyl)amino)methyl)-4-chloro-1-((R)-1-isopropylpyrrolidin-3-yl)-N-methyl-N-((S)-pyrrolidin-3-yl)-1H-imidazole-5-carboxamide, (R)-N-(azetidin-3-yl)-2-(((5-(tert-butyl)-4-chloro-2-hydroxyphenyl)amino)methyl)-4-chloro-1-(1-isopropylpyrrolidin-3-yl)-N-methyl-1H-imidazole-5-carboxamide, and 2-(((5-(tert-butyl)-6-chloro-1H-indazol-3-yl)amino)methyl)-4-chloro-N,1-dimethyl-N-(pyrrolidin-3-yl)-1H-imidazole-5-carboxamide; and pharmaceutically acceptable salts thereof.

18. A pharmaceutical composition comprising the compound of claim 1, or the pharmaceutically acceptable salt thereof, and a pharmaceutically acceptable carrier.

19. The pharmaceutical composition of claim 18 for use in the treatment of cancer.

20. The pharmaceutical composition of claim 18, wherein the pharmaceutical composition is suitable for oral administration.

21. The pharmaceutical composition of claim 18, wherein the pharmaceutical composition further comprises an additional active agent.

22. The pharmaceutical composition of claim 21, wherein the additional active agent is an anti-cancer agent selected from the group consisting of a chemotherapeutic agent, an immunotherapeutic agent, a hormonal agent, an anti-hormonal agent, a targeted therapy agent, and an anti-angiogenesis agent.

23. A method of inhibiting KRAS G12D protein comprising contacting KRAS G12D protein with the compound of claim 1 or the pharmaceutically acceptable salt thereof.

24. A method of treating cancer comprising administering a therapeutically effective amount of the compound of claim 1 or the pharmaceutically acceptable salt thereof to a subject in need of such treatment.

25. The method of claim 24, further comprising administering an additional active agent to the subject.

26. The method of claim 25, wherein the additional active agent is an anti-cancer agent selected from the group consisting of a chemotherapeutic agent, an immunotherapeutic agent, a hormonal agent, an anti-hormonal agent, a targeted therapy agent, and an anti-angiogenesis agent.

* * * * *

SEQUENCE LISTING

<160> NUMBER OF SEQ ID NOS: 4

<210> SEQ ID NO 1
<211> LENGTH: 188
<212> TYPE: PRT
<213> ORGANISM: Artificial
<220> FEATURE:
<223> OTHER INFORMATION: Synthetic protein

<400> SEQUENCE: 1

```
Met Ala Ser Ser His His His His His His Ser Ser Glu Asn Leu Tyr
1               5                   10                  15

Phe Gln Gly Met Thr Glu Tyr Lys Leu Val Val Val Gly Ala Asp Gly
            20                  25                  30

Val Gly Lys Ser Ala Leu Thr Ile Gln Leu Ile Gln Asn His Phe Val
        35                  40                  45

Asp Glu Tyr Asp Pro Thr Ile Glu Asp Ser Tyr Arg Lys Gln Val Val
    50                  55                  60

Ile Asp Gly Glu Thr Cys Leu Leu Asp Ile Leu Asp Thr Ala Gly Gln
65                  70                  75                  80

Glu Glu Tyr Ser Ala Met Arg Asp Gln Tyr Met Arg Thr Gly Glu Gly
                85                  90                  95

Phe Leu Cys Val Phe Ala Ile Asn Asn Thr Lys Ser Phe Glu Asp Ile
            100                 105                 110

His His Tyr Arg Glu Gln Ile Lys Arg Val Lys Asp Ser Glu Asp Val
        115                 120                 125

Pro Met Val Leu Val Gly Asn Lys Cys Asp Leu Pro Ser Arg Thr Val
    130                 135                 140

Asp Thr Lys Gln Ala Gln Asp Leu Ala Arg Ser Tyr Gly Ile Pro Phe
145                 150                 155                 160

Ile Glu Thr Ser Ala Lys Thr Arg Gln Gly Val Asp Asp Ala Phe Tyr
                165                 170                 175

Thr Leu Val Arg Glu Ile Arg Lys His Lys Glu Lys
            180                 185
```

<210> SEQ ID NO 2
<211> LENGTH: 487
<212> TYPE: PRT
<213> ORGANISM: Artificial
<220> FEATURE:
<223> OTHER INFORMATION: Synthetic protein

<400> SEQUENCE: 2

```
Gly Glu Glu Gln Met Arg Leu Pro Ser Ala Asp Val Tyr Arg Phe Ala
```

-continued

```
1               5                   10                  15

Glu Pro Asp Ser Glu Glu Asn Ile Ile Phe Glu Glu Asn Met Gln Pro
            20                  25                  30

Lys Ala Gly Ile Pro Ile Ile Lys Ala Gly Thr Val Ile Lys Leu Ile
        35                  40                  45

Glu Arg Leu Thr Tyr His Met Tyr Ala Asp Pro Asn Phe Val Arg Thr
    50                  55                  60

Phe Leu Thr Thr Tyr Arg Ser Phe Cys Lys Pro Gln Glu Leu Leu Ser
65                  70                  75                  80

Leu Ile Ile Glu Arg Phe Glu Ile Pro Glu Pro Glu Pro Thr Glu Ala
                85                  90                  95

Asp Arg Ile Ala Ile Glu Asn Gly Asp Gln Pro Leu Ser Ala Glu Leu
            100                 105                 110

Lys Arg Phe Arg Lys Glu Tyr Ile Gln Pro Val Gln Leu Arg Val Leu
        115                 120                 125

Asn Val Cys Arg His Trp Val Glu His His Phe Tyr Asp Phe Glu Arg
    130                 135                 140

Asp Ala Tyr Leu Leu Gln Arg Met Glu Glu Phe Ile Gly Thr Val Arg
145                 150                 155                 160

Gly Lys Ala Met Lys Lys Trp Val Glu Ser Ile Thr Lys Ile Ile Gln
                165                 170                 175

Arg Lys Lys Ile Ala Arg Asp Asn Gly Pro Gly His Asn Ile Thr Phe
            180                 185                 190

Gln Ser Ser Pro Pro Thr Val Glu Trp His Ile Ser Arg Pro Gly His
        195                 200                 205

Ile Glu Thr Phe Asp Leu Leu Thr Leu His Pro Ile Glu Ile Ala Arg
    210                 215                 220

Gln Leu Thr Leu Leu Glu Ser Asp Leu Tyr Arg Ala Val Gln Pro Ser
225                 230                 235                 240

Glu Leu Val Gly Ser Val Trp Thr Lys Glu Asp Lys Glu Ile Asn Ser
                245                 250                 255

Pro Asn Leu Leu Lys Met Ile Arg His Thr Thr Asn Leu Thr Leu Trp
            260                 265                 270

Phe Glu Lys Cys Ile Val Glu Thr Glu Asn Leu Glu Glu Arg Val Ala
        275                 280                 285

Val Val Ser Arg Ile Ile Glu Ile Leu Gln Val Phe Gln Glu Leu Asn
    290                 295                 300

Asn Phe Asn Gly Val Leu Glu Val Val Ser Ala Met Asn Ser Ser Pro
305                 310                 315                 320

Val Tyr Arg Leu Asp His Thr Phe Glu Gln Ile Pro Ser Arg Gln Lys
                325                 330                 335

Lys Ile Leu Glu Glu Ala His Glu Leu Ser Glu Asp His Tyr Lys Lys
            340                 345                 350

Tyr Leu Ala Lys Leu Arg Ser Ile Asn Pro Pro Cys Val Pro Phe Phe
        355                 360                 365

Gly Ile Tyr Leu Thr Asn Ile Leu Lys Thr Glu Glu Gly Asn Pro Glu
    370                 375                 380

Val Leu Lys Arg His Gly Lys Glu Leu Ile Asn Phe Ser Lys Arg Arg
385                 390                 395                 400

Lys Val Ala Glu Ile Thr Gly Glu Ile Gln Gln Tyr Gln Asn Gln Pro
                405                 410                 415

Tyr Cys Leu Arg Val Glu Ser Asp Ile Lys Arg Phe Phe Glu Asn Leu
            420                 425                 430
```

-continued

```
Asn Pro Met Gly Asn Ser Met Glu Lys Glu Phe Thr Asp Tyr Leu Phe
        435                 440                 445

Asn Lys Ser Leu Glu Ile Glu Pro Arg Asn Pro Lys Pro Leu Pro Arg
    450                 455                 460

Phe Pro Lys Lys Tyr Ser Tyr Pro Leu Lys Ser Pro Gly Val Arg Pro
465                 470                 475                 480

Ser Asn Pro Arg Pro Gly Thr
                485
```

```
<210> SEQ ID NO 3
<211> LENGTH: 567
<212> TYPE: DNA
<213> ORGANISM: Artificial
<220> FEATURE:
<223> OTHER INFORMATION: Synthetic DNA

<400> SEQUENCE: 3

atggcaagca gccatcatca tcatcatcat agcagcgaaa acctgtattt tcagggcatg     60

accgaatata aactggttgt tgttggtgca gatggtgttg gtaaaagcgc actgaccatt    120

cagctgattc agaatcattt tgtggatgag tatgatccga ccatcgaaga tagctatcgt    180

aaacaggttg tgattgatgg tgaaacctgt ctgctggata ttctggatac cgcaggtcaa    240

gaggaatata gcgcaatgcg tgatcagtat atgcgtaccg gtgaaggttt tctgtgtgtt    300

tttgcaatca acaataccaa aagcttcgag gatatccatc attatcgcga gcagattaaa    360

cgtgtgaaag atagcgaaga tgttccgatg gttctggttg gtaataaatg tgatctgccg    420

agccgtaccg ttgataccaa acaggcacag gatctggcac gtagctatgg tattccgttt    480

attgaaacca gcgcaaaaac ccgtcagggt gttgatgatg cattttatac cctggttcgt    540

gaaatccgca aacataaaga aaaatga                                        567
```

```
<210> SEQ ID NO 4
<211> LENGTH: 1584
<212> TYPE: DNA
<213> ORGANISM: Artificial
<220> FEATURE:
<223> OTHER INFORMATION: Synthetic DNA

<400> SEQUENCE: 4

atgggcagca gccatcatca tcatcatcac agcagcggcc tggtgccgcg cggcagccat     60

atggctagca tgactggtgg acagcaaatg ggtcgcggat ccgaaaacct gtattttcag    120

ggcgaggagc agatgaggct gcctagtgct gatgtttata gatttgcaga gcctgactct    180

gaagagaata ttatatttga agagaacatg cagcccaagg ctggaattcc aattatcaaa    240

gcaggaactg ttattaaact tatagagagg cttacgtacc atatgtacgc agatcccaat    300

tttgttcgga catttcttac aacatacaga tccttttgca aacctcaaga actactgagt    360

cttataatag aaaggtttga aattccagag cctgagccaa cagaagctga tcgcatagct    420

atagagaatg gagatcaacc cttgagtgca gaactgaaaa gatttagaaa agaatatata    480

cagcctgtgc aactgcgagt attaaatgta tgtcggcact gggtagagca ccacttctat    540

gattttgaaa gagatgcata tcttttgcaa cgaatggaag aatttattgg aacagtaaga    600

ggtaaagcaa tgaaaaaatg ggttgaatcc atcactaaaa taatccaaag gaaaaaaatt    660

gcaagagaca atggaccagg tcataatatt acatttcaga gttcacctcc cacagttgag    720

tggcatataa gcagacctgg gcacatagag acttttgacc tgctcacctt acacccaata    780
```

-continued

```
gaaattgctc gacaactcac tttacttgaa tcagatctat accgagctgt acagccatca    840

gaattagttg gaagtgtgtg gacaaaagaa gacaaagaaa ttaactctcc taatcttctg    900

aaaatgattc gacataccac caacctcact ctgtggtttg agaaatgtat tgtagaaact    960

gaaaatttag aagaaagagt agctgtggtg agtcgaatta ttgagattct acaagtcttt   1020

caagagttga acaactttaa tggtgtcctt gaggttgtca gtgctatgaa ttcatcacct   1080

gtttacagac tagaccacac atttgagcaa ataccaagtc gccagaagaa aattttagaa   1140

gaagctcatg aattgagtga agatcactat aagaaatatt tggcaaaact caggtctatt   1200

aatccaccat gtgtgccttt ctttggaatt tatctcacta atatcttgaa aacagaagaa   1260

ggcaaccctg aggtcctaaa aagacatgga aaagagctta taaactttag caaaaggagg   1320

aaagtagcag aaataacagg agagatccag cagtaccaaa atcagcctta ctgtttacga   1380

gtagaatcag atatcaaaag gttctttgaa aacttgaatc cgatgggaaa tagcatggag   1440

aaggaattta cagattatct tttcaacaaa tccctagaaa tagaaccacg aaaccctaag   1500

cctctcccaa gatttccaaa aaaatatagc tatcccctaa aatctcctgg tgttcgtcca   1560

tcaaacccaa gaccaggtac ctaa                                          1584
```